(12) United States Patent
Pitts et al.

(10) Patent No.: US 7,683,171 B2
(45) Date of Patent: Mar. 23, 2010

(54) 1H-IMIDAZO[4,5-D]THIENO[3,2-B]PYRIDINE BASED TRICYCLIC COMPOUNDS AND PHARMACEUTICAL COMPOSITIONS COMPRISING SAME

(75) Inventors: William J. Pitts, Newtown, PA (US); Jagabandhu Das, Mercerville, NJ (US); Yuping Qiu, Glastonbury, CT (US); Steven H. Spergel, Warrington, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1085 days.

(21) Appl. No.: 11/346,986

(22) Filed: Feb. 3, 2006

(65) Prior Publication Data

US 2006/0178393 A1 Aug. 10, 2006

Related U.S. Application Data

(60) Provisional application No. 60/650,187, filed on Feb. 4, 2005.

(51) Int. Cl.
*A61K 31/4365* (2006.01)
*C07D 491/12* (2006.01)
(52) U.S. Cl. .................................. 546/83; 514/293
(58) Field of Classification Search ................. 546/83; 514/293
See application file for complete search history.

(56) References Cited

U.S. PATENT DOCUMENTS

| 4,753,951 | A * | 6/1988 | Takada et al. ........... 514/293 |
| 6,933,294 | B2 | 8/2005 | Belema et al. |
| 7,071,333 | B2 | 7/2006 | Combs et al. |
| 2004/0204432 | A1 | 10/2004 | Qiu et al. |
| 2005/0101626 | A1 | 5/2005 | Pitts et al. |
| 2006/0106051 | A1 | 5/2006 | Dyckman et al. |
| 2006/0128741 | A1 | 6/2006 | Das et al. |

FOREIGN PATENT DOCUMENTS

| EP | 223420 | 5/1987 |
| JP | 2004/161674 | 6/2004 |
| WO | WO93/12116 | 6/1993 |
| WO | WO00/09506 | 2/2000 |
| WO | WO01/58900 | 8/2001 |
| WO | WO02/16370 | 2/2002 |

OTHER PUBLICATIONS

Dorwald F. A. Side Reactions in Organic Synthesis, 2005, Wiley: VCH, Weinheim p. IX of Preface.*
U.S. Appl. No. 11/430,215, filed May 20, 2006, Pitts et al.

* cited by examiner

*Primary Examiner*—Rita J Desai
(74) *Attorney, Agent, or Firm*—Mary K. Van Atten

(57) ABSTRACT

The present invention provides for thiazolopyridine-based tricyclic compounds having the formula (I), wherein $R^1$, $R^2$, $R^5$, $R^6$ and $R^7$ are as described herein. The present invention further provides pharmaceutical compositions comprising such compounds, as well as the use of such compounds for treating inflammatory and immune diseases.

9 Claims, No Drawings

1H-IMIDAZO[4,5-D]THIENO[3,2-B]PYRIDINE BASED TRICYCLIC COMPOUNDS AND PHARMACEUTICAL COMPOSITIONS COMPRISING SAME

RELATED APPLICATION

This application claims a benefit of priority from U.S. Provisional Application No. 60/650,187, filed Feb. 4, 2005, the entire disclosure of which is herein incorporated by reference.

FIELD OF THE INVENTION

The present invention relates to 1H-imidazo[4,5-d]thieno[3,2-b]pyridine based tricyclic compounds, to methods of using the compounds in treating inflammatory and immune diseases, and cancer and to pharmaceutical compositions comprising same.

BACKGROUND OF THE INVENTION

Tumor necrosis factor (TNF-α) is a potent cytokine having pro-inflammatory properties that is released by many cell types when stimulated. Studies have shown a relationship between elevated levels of TNF-α and a variety of diseases such as septic shock, hematopoiesis, tumors, and inflammatory disorders of the central nervous system, including HIV encephalitis, cerebral malaria, and meningitis. Additionally, certain neurodegenerative diseases such as Alzheimer's disease, Parkinson's disease, and Creutzfeldt-Jacob disease also are reportedly associated with enhanced TNF-α levels. See, e.g., Arvin et al., "*The Role of Inflammation and Cytokines in Brain Injury,*" Neuroscience and Biobehavioral Reviews, Vol. 20, No. 3 (1996), at pp. 445-452. More recently agents which inhibit the action of TNF-α have demonstrated clinical utility in a variety of diseases such as rheumatoid arthritis, psoriasis, and inflammatory bowel disease. See, e.g. Keating, et al. "*Infliximab: An Updated Review of its use in Crohn's Disease and Rheumatoid Arthritis*" BioDrugs Vol 16, (2002) pp. 111-148, and Hanns-Martin, et al. "*Perspectives for TNF-alpha-targeting Therapies.*" Arthritis Res. Vol 4. Supp 3 (2002) pp. S17-24.

Accordingly, various classes of drugs have been researched and developed to inhibit TNF-α production at both transcriptional and translational levels, e.g., corticosteroids, rolipram (a phosphodiesterase IV inhibitor suppressing TNF-α mRNA synthesis), calphostin, and imidazole-type cytokine suppressing anti-inflammatory drugs (CSAIDs or P-38 inhibitors). These drugs are useful in treating a variety of diseases. See Dinarello, "*Role of Pro-and Anti-Inflammatory Cytokines During Inflammation: Experimental and Clinical Findings, Review*, Vol. 0393-974X (1997), at pp. 91-103.

Recently, attention has focussed on the role of Nuclear factor κB (NF-κB) in the activation pathway that leads to production of TNF-α and other inflammatory cytokines and gene products. Besides TNF-α, NF-κB is involved in the regulation of a variety of genes involved in immune function and inflammation. These include the cytokines IL-1, IL-2, IL-6, IL-2Rα, and GM-GSF, the chemokines IL-8, MCP-1 (CCR2), and RANTES, the adhesion molecules, intercellular adhesion molecule-1 (ICAM-1), vascular cellular adhesion molecule-1 (VCAM-1) and E-selectin, the proteases matrix metalloproteinase-1 (MMP-1), MMP-9 and MMP-13, and the pro-inflammatory enzymes cyclooxygenase-2 (COX-2), iNOS, and cPLA$_2$. Thus, inhibition of NF-κB and/or its activation pathway provides a means for treating various diseases including autoimmune diseases, inflammatory diseases, Alzheimer's disease, atherosclerosis, oncogenesis, and so forth by a variety of modes of action (i.e. cytokine reduction, chemokine reduction, reduction of adhesion molecule expression, decreased expression of certain proteases implicated in inflammatory and immune disease processes, and decreased production of enzymes which produce pro-inflammatory mediators) which have been implicated in a variety of disease progression. See, e.g., Baldwin, "*The NF-κB and IκB Proteins: New Discoveries and Insights,*" Annual Rev. Immunol., Vol. 14 (1996), at pp. 649-81; see also Christman et al., "*Impact of Basic Research on Tomorrow's Medicine, The Role of Nuclear Factor-κB in Pulmonary Diseases,*" Chest Vol. 117 (2000), at pp. 1482-87, and Roshak, et al., "*Small-molecule Inhibitors of NF-κB for the Treatment of Inflammatory Joint Disease.*" Current Opinion in Pharmacol. Vol. 2 (2002) pp. 316-321.

Additionally attention has focussed on inhibition of NF-κB and/or its activation pathway to provide a means for treating cancer. Genes which mediate either tumorigenesis or tumor metastasis are regulated by NF-κB. In addition NF-κB is know to be activated by carcinogens and tumor promotors. See e.g., Karin et al.; "*NF-κB in Cancer: From Innocent Bystander to Major Culprit,*" Nature Rev. Cancer., Vol. 2 (2002) at pp. 301-310; see also Bharti et al.; "*Nuclear factor-kappa B and cancer: its role in prevention and therapy*" in Biochem. Pharmocol. at pp. 883-888.

IκB is a cytoplasmic protein that controls NF-κB activity by retaining NF-κB in the cytoplasm. IκB is phosphorylated by the IκB kinase (IKK), which has two isoforms, IKK-α ("IKK-1") and IKK-β ("IKK-2"). When IKK phosphorylates IκB, NF-κB is rapidly released from the cytoplasm into the cell. Upon release into the cell, NF-κB translocates to the nucleus where it binds to the promoters of many genes and up-regulates the transcription of pro-inflammatory genes. Thus inhibitors of IKK-1 and/or IKK-2 would prevent translocation of NF-kB to the nucleus and prevent transcription of the pro-inflammatory gene products described above. For example see Burke, et al. "*BMS-345541 is a Highly Selective Inhibitor of IκB Kinase that Binds at an Allosteric Site of the Enzyme and Blocks NF-κB dependent Transcription in Mice.*" J. Biol. Chem. Vol. 278, (2003) pp. 1450-1456.

The therapeutic effects of glucocorticoids are mediated in part by their ability to inhibit NF-κB activity by two mechanisms, i.e., up-regulating IκB protein levels and inhibiting NF-κB subunits. The deleterious side effects of glucocorticoids (such as osteoporosis, hyperglycemia, fat redistribution, etc.) have been postulated to result from the interaction of glucocorticoids with the glucocorticoid receptor (GR) or the glucocorticoid response element (GRE). For example see Schacke, et al. "*Mechanisms Involved in the Side Effects of Glucocorticoids*" Pharmacol. and Therapeutics Vol 96 (2002) pp. 23-43. Thus inhibitors of IKK-1 and/or IKK-2 inhibitors should provide much of the therapeutic benefit of glucocorticoids with a greatly improved side effect profile.

As may be appreciated, those in the field of pharmaceutical research continue to seek to develop new compounds and compositions having increased effectiveness, bioavailability, and solubility, having fewer side effects, and/or providing the physician and patient with a choice of treatment options. Particularly in the area of immune response, individuals respond differently depending upon the type of treatment and chemical agent used. Mechanisms of action continue to be studied to aid in understanding the immune response and in developing compounds effective for treating inflammatory and immune-related disorders.

The present invention provides for novel tricyclic compounds useful as inhibitors of IKK.

SUMMARY OF THE INVENTION

Accordingly, the present invention provides novel inhibitors of IKK enzyme activity, or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating disorders selected from rheumatoid arthritis, asthma, inflammatory bowel disease, chronic obstructive pulmonary disease, psoriasis, and cancer, comprising administering to a host in need of such treatment a therapeutically effective amount of at least one of the compounds of the present invention or a pharmaceutically acceptable salt or prodrug form thereof.

The present invention provides a method for treating inflammatory, and/or immune diseases and cancer, comprising administering to a host in need of such treatment a therapeutically effective amount of at least one of the compounds of the present invention or a pharmaceutically acceptable salt or prodrug form thereof.

The present invention provides novel compounds for use in therapy.

The present invention provides the use of novel compounds for the manufacture of a medicament for the treatment of inflammatory diseases and cancer.

These and other features of the invention, which will become apparent during the following detailed description, have been achieved by the inventors' discovery that compounds of formula (I):

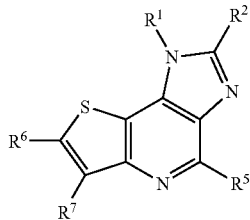

(I)

or stereoisomers or pharmaceutically acceptable salts thereof, wherein $R^1$, $R^2$, $R^5$, $R^6$, and $R^7$ are defined below, are effective modulators of chemokine activity.

DETAILED DESCRIPTION OF EMBODIMENTS OF THE INVENTION

The invention is directed to compounds of formula (I), useful in treating inflammatory or immune conditions or cancer:

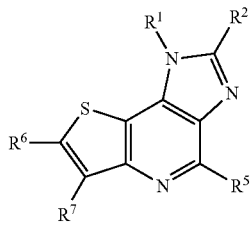

(I)

enantiomers, diastereomers, salts, and solvates thereof wherein $R^1$ is selected from hydrogen, $C_{1-3}$ alkyl, $C_{2-3}$ alkenyl, and $C_{2-3}$ alkynyl;

$R^2$ is hydrogen, alkyl, alkenyl, alkynyl, haloalkyl, $R^5$ is —$NR^3R^4$;

$R^3$ and $R^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
(c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12a}R^{13}$, or —$N(R^{12})SO_2NR^{12a}R^{13}$ or —$C(O)OR^{14}$, —$C(O)R^{11}$, —$C(O)NR^{12}R^{13}$, —$SO_2R^{14}$, —$SO_2NR^{12}R^{13}$;
(d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$R^6$ is
(a) alkyl, alkenyl, alkynyl, any of which is substituted with one or more as valence allows $Z^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(b) —$SR^{7a}$, —$SO_2R^{10}$, —$SO_2NR^{8b}R^{9b}$, $C(O)R^{7a}$, —$C(O)OR^{7a}$, or —$C(O)NR^{8a}R^{9a}$;

$R^7$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) —$SR^{7a}$, —$SO_2R^{10}$, —$SO_2NR^{8b}R^{9b}$, —$C(O)R^{7a}$, —$C(O)OR^{7a}$, or —$C(O)NR^{8a}R^{9a}$;

$R^{7a}$ is
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{8a}$, $R^{8b}$, $R^{9a}$ and $R^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;
(c) $R^{8a}$ and $R^{9a}$ together with the nitrogen atom to which they are attached combine to form a 3 to 8 membered heterocyclic ring optionally independently substituted as valence allows with one or more $Z^{1b}$, $Z^{2b}$ and $Z^{3b}$; or
(d) $R^{8b}$ and $R^{9b}$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$R^{10}$, at each occurance, is independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
  (a) hydrogen, or
  (b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
  (1) a bond
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more $V^{1-5}$; or where $V^{1-5}$ are independently
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more of groups (3)-(25) of $V^{1-5}$;
  (3) —$U^1$—O—$Y^5$,
  (4) —$U^1$—S—$Y^5$,
  (5) —$U^1$—C(O)$_t$—H, —$U^1$—C(O)$_t$—$Y^5$ where t is 1 or 2,
  (6) —$U^1$—SO$_3$—H, or —$U^1$—S(O)$_t Y^5$,
  (7) —$U^1$-halo,
  (8) —$U^1$-cyano,
  (9) —$U^1$-nitro,
  (10) —$U^1$—NY$^2 Y^3$,
  (11) —$U^1$—N($Y^4$)—C(O)—$Y^1$,
  (12) —$U^1$—N($Y^4$)—C(S)—$Y^1$,
  (13) —$U^1$—N($Y^4$)—C(O)—NY$^2 Y^3$,
  (14) —$U^1$—N($Y^4$)—C(S)—NY$^2 Y^3$,
  (15) —$U^1$—N($Y^4$)—C(O)O—$Y^5$,
  (16) —$U^1$—N($Y^4$)—S(O)$_2$—$Y^1$,
  (17) —$U^1$—N($Y^4$)—S(O)$_2$—NY$^2 Y^3$,
  (18) —$U^1$—C(O)—NY$^2 Y^3$,
  (19) —$U^1$—OC(O)—NY$^2 Y^3$
  (20) —$U^1$—S(O)$_2$—N($Y^4$)—$Y^1$,
  (21) —$U^1$—N($Y^4$)—C(=$NV^{1a}$)—NY$^2 Y^3$,
  (22) —$U^1$—N($Y^4$)—C(=$NV^{1a}$)—$Y^1$,
  (23) —$U^1$—C(=$NV^{1a}$)—NY$^2 Y^3$,
  (24) oxo;
  (25) —$U^1$—$Y^5$;

$Z^{1f}$, at each occurrence, is independently selected from
  (1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with one or more of groups (2) to (25) of $Z^{1f}$;
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^5$,
  (4) —$U^1$—S—$Y^5$,
  (5) —$U^1$—C(O)$_t$—H, —$U^1$—C(O)$_t$—$Y^5$ where t is 1 or 2,
  (6) —$U^1$—SO$_3$—H, or —$U^1$—S(O)$_t Y^5$,
  (7) —$U^1$-halo,
  (8) —$U^1$-cyano,
  (9) —$U^1$-nitro,
  (10) —$U^1$—NY$^2 Y^3$,
  (11) —$U^1$—N($Y^4$)—C(O)—$Y^1$,
  (12) —$U^1$—N($Y^4$)—C(S)—$Y^1$,
  (13) —$U^1$—N($Y^4$)—C(O)—NY$^2 Y^3$,
  (14) —$U^1$—N($Y^4$)—C(S)—NY$^2 Y^3$,
  (15) —$U^1$—N($Y^4$)—C(O)O—$Y^5$,
  (16) —$U^1$—N($Y^4$)—S(O)$_2$—$Y^1$,
  (17) —$U^1$—N($Y^4$)—S(O)$_2$—NY$^2 Y^3$,
  (18) —$U^1$—C(O)—NY$^2 Y^3$,
  (19) —$U^1$—OC(O)—NY$^2 Y^3$
  (20) —$U^1$—S(O)$_2$—N($Y^4$)—$Y^1$,
  (21) —$U^1$—N($Y^4$)—C(=$NV^{1a}$)—NY$^2 Y^3$,
  (22) —$U^1$—N($Y^4$)—C(=$NV^{1a}$)—$Y^1$,
  (23) —$U^1$—C(=$NV^{1a}$)—NY$^2 Y^3$,
  (24) oxo;
  (25) —$U^1$—$Y^5$;

$V^{1a}$ is independently hydrogen, alkyl, —CN, —C(O)$Y^1$, —S(O)$_2 Y^5$, S(O)$_2$NY$^2 Y^3$;

$Y^1$, $Y^2$, $Y^3$, $Y^4$ and $Y^5$
  (1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more $Z^4$, $Z^5$ and $Z^6$; or
  (2) $Y^2$ and $Y^3$ may together be alkylene or alkenylene, completing a 3- to 8-membered saturated or unsaturated ring together with the atoms to which they are attached, or
  (4) $Y^2$ and $Y^3$ together with the nitrogen atom to which they are attached may combine to form a group —N=$CY^6 Y^7$ where $Y^6$ and $Y^7$ are each independently H or alkyl; and $Z^4$, $Z^5$, and $Z^6$ are optional substituents at each occurrence independently selected from
  (1) H
  (2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
  (3) —$U^1$—O—$Y^{5a}$,
  (4) —$U^1$—S—$Y^{5a}$,
  (5) —$U^1$—C(O)$_t$—H, —$U^1$—C(O)$_t$—$Y^{5a}$ where t is 1 or 2,
  (6) —$U^1$—SO$_3$—H, or —$U^1$—S(O)$_t Y^{5a}$,
  (7) —$U^1$-halo,
  (8) —$U^1$-cyano,
  (9) —$U^1$-nitro,
  (10) —$U^1$—NY$^{2a} Y^{3a}$,
  (11) —$U^1$—N($Y^{4a}$)—C(O)—$Y^{1a}$,
  (12) —$U^1$—N($Y^{4a}$)—C(S)—$Y^{1a}$,
  (13) —$U^1$—N($Y^{4a}$)—C(O)—NY$^{2a} Y^{3a}$,
  (14) —$U^1$—N($Y^{4a}$)—C(S)—NY$^{2a} Y^{3a}$,
  (15) —$U^1$—N($Y^{4a}$)—C(O)O—$Y^{5a}$,
  (16) —$U^1$—N($Y^{4a}$)—S(O)$_2$—$Y^{1a}$,
  (17) —$U^1$—N($Y^{4a}$)—S(O)$_2$—NY$^{2a} Y^{3a}$,
  (18) —$U^1$—C(O)—NY$^{2a} Y^{3a}$,
  (19) —$U^1$—OC(O)—NY$^{2a} Y^{3a}$
  (20) —$U^1$—S(O)$_2$—N($Y^{4a}$)—$Y^{1a}$,
  (21) —$U^1$—N($Y^{4a}$)—C(=$NV^{1a}$)—NY$^{2a} Y^{3a}$,
  (22) —$U^1$—N($Y^{4a}$)—C(=$NV^{1a}$)—$Y^{1a}$,

(23) —U$^1$—C(=NV$^{1a}$)—NY$^{2a}$Y$^{3a}$,
(24) oxo;
(25) —U$^1$—Y$^{5a}$;

Y$^{1a}$, Y$^{2a}$, Y$^{3a}$, Y$^{4a}$ and Y$^{5a}$
(1) are each independently hydrogen, alkyl, (hydroxy) alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

U$^1$ is independently
(1) a single bond,
(2) alkylene,
(3) alkenylene, or
(4) alkynylene.

The invention is directed to compounds of formula (I), useful in treating inflammatory or immune conditions or cancer:

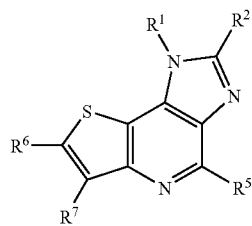

(I)

enantiomers, diastereomers, salts, and solvates thereof wherein

R$^1$ is selected from hydrogen, C$_{1-3}$ alkyl, C$_{2-3}$ alkenyl, and C$_{2-3}$ alkynyl;

R$^2$ is hydrogen, alkyl, alkenyl, alkynyl, haloalkyl,

R$^5$ is selected from
a) hydrogen and halo,
(b) alkyl, alkenyl, alkynyl, and haloalkyl, any of which may be optionally independently substituted as valence allows with one or more Z$^{1b}$, Z$^{2b}$ and Z$^{3b}$;
(c) —OR$^{11}$, —SR$^{11}$ and —NR$^3$R$^4$;

R$^3$ and R$^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1b}$, Z$^{2b}$ and Z$^{3b}$;
(c) —OR$^{11}$, —NR$^{12}$R$^{13}$, —N(R$^{12}$)C(O)R$^{14}$, —N(R$^{12}$)C(O)OR$^{14}$, —N(R$^{12}$)SO$_2$R$^{14}$, —N(R$^{12}$)C(O)NR$^{12a}$R$^{13}$, or —N(R$^{12}$)SO$_2$NR$^{12a}$R$^{13}$ or —C(O)OR$^{14}$, —C(O)R$^{11}$, —C(O)NR$^{12}$R$^{13}$, —SO$_2$R$^{14}$, —SO$_2$NR$^{12}$R$^{13}$;
(d) R$^3$ and R$^4$ together with the nitrogen atom to which they are attached combine to form a 3 to 8 membered heterocyclic ring optionally independently substituted as valence allows with one or more Z$^{1b}$, Z$^{2b}$ and Z$^{3b}$;

R$^6$ is
(a) alkyl, alkenyl, alkynyl, any of which is substituted with one or more as valence allows Z$^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more Z$^{1d}$, Z$^{2d}$ and Z$^{3d}$; or
(b) SR$^{7a}$, —SO$_2$R$^{10}$, —SO$_2$NR$^{8b}$R$^{9b}$, C(O)R$^{7a}$, —C(O)OR$^{7a}$, or —C(O)NR$^{8a}$R$^{9a}$;

R$^7$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more Z$^{1d}$, Z$^{2d}$ and Z$^{3d}$; or
(c) -, —SR$^{7a}$, —SO$_2$R$^{10}$, —SO$_2$NR$^{8b}$R$^{9b}$, —C(O)R$^{7a}$, —C(O)OR$^{7a}$, or —C(O)NR$^{8a}$R$^{9a}$;

R$^{7a}$ and R$^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1c}$, Z$^{2c}$ and Z$^{3c}$;

R$^{8a}$, R$^{8b}$, R$^{9a}$ and R$^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1d}$, Z$^{2d}$ and Z$^{3d}$;
(c) R$^{8a}$ and R$^{9a}$ together with the nitrogen atom to which they are attached combine to form a 3 to 8 membered heterocyclic ring optionally independently substituted as valence allows with one or more Z$^{1b}$, Z$^{2b}$ and Z$^{3b}$; or
(d) R$^{8b}$ and R$^{9b}$ together with the nitrogen atom to which they are attached combine to form a 3 to 8 membered heterocyclic ring optionally independently substituted as valence allows with one or more Z$^{1b}$, Z$^{2b}$ and Z$^3$; R$^{10}$, at each occurance, is independently alkyl, alkenyl, alkynyl, haloalkyl, cycloalkyl, (cycloalkyl)alkyl, aryl, (aryl) alkyl, heterocyclo, (heterocyclo)alkyl, heteroaryl, or (heteroaryl)alkyl any of which may be optionally independently substituted as valence allows with one or more Z$^{1d}$, Z$^{2d}$ and Z$^{3d}$;

R$^{11}$, R$^{12}$, R$^{12a}$ and R$^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more Z$^{1e}$, Z$^{2e}$ and Z$^{3e}$;

R$^{14}$ is alkyl, alkenyl, alkynyl, haloalkyl, cycloalkyl, (cycloalkyl)alkyl, aryl, (aryl)alkyl, heterocyclo, (heterocyclo) alkyl, heteroaryl, or (heteroaryl)alkyl any of which may be optionally independently substituted as valence allows with one or more Z$^{1e}$, Z$^{2e}$ and Z$^{3e}$;

Z$^{1a-1e}$, Z$^{2a-2e}$, and Z$^{3a-3e}$ are optional substituents at each occurrence independently selected from —W$^1$—V$^1$; —W$^2$—V$^2$; —W$^3$—V$^3$; —W$^4$—V$^4$; —W$^5$—V$^5$;

where W$^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo) alkyl, heteroaryl, or (heteroaryl)alkyl, any of which may be optionally independently substituted as valence allows with one or more V$^{1-5}$; or where V$^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo) alkyl, heteroaryl, or (heteroaryl)alkyl, any of which may be optionally independently substituted as valence allows with one or more of groups (3)-(25) of $V^{1-5}$;
(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—SO$_3$—H, or —$U^1$—S(O)$_t$$Y^5$,
(7) —$U^1$-halo,
(8) —$U^1$-cyano,
(9) —$U^1$-nitro,
(10) —$U^1$—N$Y^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—N$Y^2Y^3$,
(14) —$U^1$—N($Y^4$)—C(S)—N$Y^2Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—N$Y^2Y^3$,
(18) —$U^1$—C(O)—N$Y^2Y^3$,
(19) —$U^1$—OC(O)—N$Y^2Y^3$
(20) —$U^1$—S(O)$_2$—N($Y^4$)—$Y^1$,
(21) —$U^1$—N($Y^4$)—C(=N$V^{1a}$)—N$Y^2Y^3$,
(22) —$U^1$—N($Y^4$)—C(=N$V^{1a}$)—$Y^1$,
(23) —$U^1$—C(=N$V^{1a}$)—N$Y^2Y^3$,
(24) oxo;
(25) —$U^1$—$Y^5$;

$Z^{1f}$, at each occurrence, is independently selected from
(1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with one or more of groups (2) to (25) of $Z^{1f}$;
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—SO$_3$—H, or —$U^1$—S(O)$_t$$Y^5$,
(7) —$U^1$-halo,
(8) —$U^1$-cyano,
(9) —$U^1$-nitro,
(10) —$U^1$—N$Y^2Y^3$,
(11) —$U^1$—N($Y^4$)—C(O)—$Y^1$,
(12) —$U^1$—N($Y^4$)—C(S)—$Y^1$,
(13) —$U^1$—N($Y^4$)—C(O)—N$Y^2Y^3$,
(14) —$U^1$—N($Y^4$)—C(S)—N$Y^2Y^3$,
(15) —$U^1$—N($Y^4$)—C(O)O—$Y^5$,
(16) —$U^1$—N($Y^4$)—S(O)$_2$—$Y^1$,
(17) —$U^1$—N($Y^4$)—S(O)$_2$—N$Y^2Y^3$,
(18) —$U^1$—C(O)—N$Y^2Y^3$,
(19) —$U^1$—OC(O)—N$Y^2Y^3$
(20) —$U^1$—S(O)$_2$—N($Y^4$)—$Y^1$,
(21) —$U^1$—N($Y^4$)—C(=N$V^{1a}$)—N$Y^2Y^3$,
(22) —$U^1$—N($Y^4$)—C(=N$V^{1a}$)—$Y^1$,
(23) —$U^1$—C(=N$V^{1a}$)—N$Y^2Y^3$,
(24) oxo;
(25) —$U^1$—$Y^5$;

$V^{1a}$ is independently hydrogen, alkyl, —CN, —C(O)$Y^1$, —S(O)$_2Y^5$, S(O)$_2$N$Y^2Y^3$;

$Y^1, Y^2, Y^3, Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more $Z^4, Z^5$ and $Z^6$; or
(2) $Y^2$ and $Y^3$ may together be alkylene or alkenylene, completing a 3- to 8-membered saturated or unsaturated ring together with the atoms to which they are attached, or
(4) $Y^2$ and $Y^3$ together with the nitrogen atom to which they are attached may combine to form a group —N=C$Y^6Y^7$ where $Y^6$ and $Y^7$ are each independently H or alkyl; and $Z^4, Z^5$, and $Z^6$ are optional substituents at each occurrence independently selected from
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^{5a}$,
(4) —$U^1$—S—$Y^{5a}$,
(5) —$U^1$—C(O)$_t$—H, —$U^1$—C(O)$_t$—$Y^{5a}$ where t is 1 or 2,
(6) —$U^1$—SO$_3$—H, or —$U^1$—S(O)$_t$$Y^{5a}$,
(7) —$U^1$-halo,
(8) —$U^1$-cyano,
(9) —$U^1$-nitro,
(10) —$U^1$N$Y^{2a}Y^{3a}$,
(11) —$U^1$—N($Y^{4a}$)—C(O)—$Y^{1a}$,
(12) —$U^1$—N($Y^{4a}$)—C(S)—$Y^{1a}$,
(13) —$U^1$—N($Y^{4a}$)—C(O)—N$Y^{2a}Y^{3a}$,
(14) —$U^1$—N($Y^{4a}$)—C(S)—N$Y^{2a}Y^{3a}$,
(15) —$U^1$—N($Y^{4a}$)—C(O)O—$Y^{5a}$,
(16) —$U^1$—N($Y^{4a}$)—S(O)$_2$—$Y^{1a}$,
(17) —$U^1$—N($Y^{4a}$)—S(O)$_2$—N$Y^{2a}Y^{3a}$,
(18) —$U^1$—C(O)—N$Y^{2a}Y^{3a}$,
(19) —$U^1$—OC(O)—N$Y^{2a}Y^{3a}$
(20) —$U^1$—S(O)$_2$—N($Y^{4a}$)—$Y^{1a}$,
(21) —$U^1$—N($Y^{4a}$)—C(=N$V^{1a}$)—N$Y^{2a}Y^{3a}$,
(22) —$U^1$—N($Y^{4a}$)—C(=N$V^{1a}$)—$Y^{1a}$,
(23) —$U^1$—C(=N$V^{1a}$)—N$Y^{2a}Y^{3a}$,
(24) oxo;
(25) —$U^1$—$Y^{5a}$;

$Y^{1a}, Y^{2a}, Y^{3a}, Y^{4a}$ and $Y^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

$U^1$ is independently
(1) a single bond,
(2) alkylene,
(3) alkenylene, or
(4) alkynylene.

In another embodiment, the present invention is directed to compounds of formula (I), wherein
$R^3$ and $R^4$ are independently
(a) hydrogen,
(b) alkyl, haloalkyl, (hydroxy)alkyl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1b}, Z^{2b}$ and $Z^{3b}$;
(c) —N$R^{12}R^{13}$; or
(d) $R^3$ and $R^4$ together with the nitrogen atom to which they are attached combine to form a 3 to 8 membered heterocyclic ring optionally independently substituted as valence allows with one or more $Z^{1b}, Z^{2b}$ and $Z^{3b}$.

In another embodiment, the present invention is directed to compounds of formula (I), wherein
R⁶ is
(a) alkyl, alkenyl, alkynyl, any of which is substituted with one or more as valence allows $Z^{1f}$; aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1d}$, $Z^{2d}$ and $Z^{3d}$; or
(b) —C(O)R$^{7a}$, —C(O)OR$^{7a}$, or —C(O)NR$^{8a}$R$^{9a}$.

In another embodiment, the present invention is directed to compounds of formula (I), wherein
R$^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$.

In another embodiment, the present invention is directed to compounds of formula (I), wherein
R³ and R⁴ are independently hydrogen, alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$; —NR$^{12}$R$^{13}$; or
alternatively, R³ and R⁴ together with the nitrogen atom to which they are attached combine to form a 3 to 6 membered heterocyclic ring selected from piperidinyl, morpholinyl, pyrrolidinyl, piperazinyl, and azetidinyl; optionally independently substituted as valence allows with one or more $Z^{1b}$, $Z^{2b}$ and $Z^{3b}$;
R⁶ is
(a) alkyl, which is substituted with one or more as valence allows $Z^{1f}$; aryl, heteroaryl, cycloalkyl, (cycloalkyl)alkyl, heterocyclo, (heterocyclo)alkyl, aryl, (aryl)alkyl, heteroaryl, or (heteroaryl)alkyl any of which may be optionally independently substituted as valence allows with one or more $Z^{1d}$, $Z^{2d}$ and $Z^{3d}$; or
(b) —C(O)R$^{7a}$, or —C(O)NR$^{8a}$R$^{9a}$.

In another embodiment, the present invention is directed to compounds of formula (I), wherein
R¹ is hydrogen, methyl, ethyl, propyl, i-propyl, prop-2-enyl, prop-1-enyl; and
R² is hydrogen, methyl, trifluoromethyl, and phenyl.

The invention is directed to compounds of formula (I), useful in treating inflammatory or immune conditions or cancer:

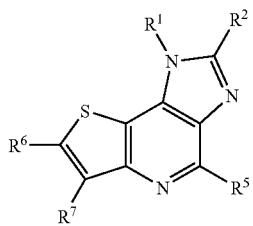

(I)

enantiomers, diastereomers, salts, and solvates thereof
wherein
R¹ is selected from hydrogen and C$_{1-3}$ alkyl;
R⁶ is
(a) alkyl, alkenyl, alkynyl, any of which is substituted with one or more as valence allows $Z^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(b) C(O)R$^{7a}$, —C(O)OR$^{7a}$, or C(O)NR$^{8a}$R$^{9a}$;
R⁷ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) -, —SR$^{7a}$, —SO$_2$R$^{10}$, —SO$_2$NR$^{8b}$R$^{9b}$, —C(O)R$^{7a}$, —C(O)OR$^{7a}$, or —C(O)NR$^{8a}$R$^{9a}$;
$Z^{1a-1e}$, $Z^{2a-2e}$, and $Z^{3a-3e}$ are optional substituents at each occurrence independently selected from —W¹—V¹; —W²—V²; —W³—V³; —W⁴—V⁴; —W⁵—V⁵;
where W$^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
where V$^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —U¹—O—Y⁵,
(4) —U¹—S—Y⁵,
(5) —U¹—C(O)$_t$—H, —U¹—C(O)$_t$—Y⁵ where t is 1 or 2,
(6) —U¹—SO$_3$—H, or —U¹—S(O)$_t$Y⁵,
(7) —U¹-halo,
(8) —U¹-cyano,
(9) —U¹-nitro,
(10) —U¹—NY²Y³,
(11) —U¹—N(Y⁴)—C(O)—Y¹,
(12) —U¹—N(Y⁴)—C(S)—Y¹,
(13) —U¹—N(Y⁴)—C(O)—NY²Y³,
(14) —U¹—N(Y⁴)—C(S)—NY²Y³,
(15) —U¹—N(Y⁴)—C(O)O—Y⁵,
(16) —U¹—N(Y⁴)—S(O)$_2$—Y¹,
(17) —U¹—N(Y⁴)—S(O)$_2$—NY²Y³,
(18) —U¹—C(O)—NY²Y³,
(19) —U¹—OC(O)—NY²Y³,
(20) —U¹—S(O)$_2$—N(Y⁴)—Y¹,
(21) —U¹—N(Y⁴)—C(=NV$^{1a}$)—NY²Y³,
(22) —U¹—N(Y⁴)—C(=NV$^{1a}$)—Y¹,
(23) —U¹—C(=NV$^{1a}$)—NY²Y³,
(24) oxo;
(25) —U¹—Y⁵;
$Z^{1f}$, at each occurrence, is independently selected from
(1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with groups (2) to (25);
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —U¹—O—Y⁵,
(4) —U¹—S—Y⁵,
(5) —U¹—C(O)$_t$—H, —U¹—C(O),—Y⁵ where t is 1 or 2,
(6) —U¹—SO$_3$—H, or —U¹—S(O)$_t$Y⁵,
(7) —U¹-halo,
(8) —U¹-cyano,
(9) —U¹-nitro,
(10) —U¹—NY²Y³,

(11) —$U^1$—$N(Y^4)$—$C(O)$—$Y^1$,
(12) —$U^1$—$N(Y^4)$—$C(S)$—$Y^1$,
(13) —$U^1$—$N(Y^4)$—$C(O)$—$NY^2Y^3$,
(14) —$U^1$—$N(Y^4)$—$C(S)$—$NY^2Y^3$,
(15) —$U^1$—$N(Y^4)$—$C(O)O$—$Y^5$,
(16) —$U^1$—$N(Y^4)$—$S(O)_2$—$Y^1$,
(17) —$U^1$—$N(Y^4)$—$S(O)_2$—$NY^2Y^3$,
(18) —$U^1$—$C(O)$—$NY^2Y^3$,
(19) —$U^1$—$OC(O)$—$NY^2Y^3$
(20) —$U^1$—$S(O)_2$—$N(Y^4)$—$Y^1$,
(21) —$U^1$—$N(Y^4)$—$C(=NV^{1a})$—$NY^2Y^3$,
(22) —$U^1$—$N(Y^4)$—$C(=NV^{1a})$—$Y^1$,
(23) —$U^1C(=NV^{1a})$—$NY^2Y^3$,
(24) oxo;
(25) —$U^1$—$Y^5$;

$V^{1a}$ is independently hydrogen, alkyl, —CN, —$C(O)Y^1$, —$S(O)_2Y^5$, $S(O)_2NY^2Y^3$;

$Y^1$, $Y^2$, $Y^3$, $Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl; or
(2) $Y^2$ and $Y^3$ may together be alkylene or alkenylene, completing a 3- to 8-membered saturated or unsaturated ring together with the atoms to which they are attached, or
(4) $Y^2$ and $Y^3$ together with the nitrogen atom to which they are attached may combine to form a group —N=$CY^6Y^7$ where $Y^6$ and $Y^7$ are each independently H or alkyl.

In another embodiment, the present invention is directed to compounds of formula (I) wherein
$R^3$ and $R^4$ are independently
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1b}$, $Z^{2b}$ and $Z^{3b}$;
(c) —$NR^{12}R^{13}$; or
(d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$.

In another embodiment, the present invention is directed to compounds of formula (I) wherein
$R^6$ is
(a) alkyl, alkenyl, alkynyl any of which is substituted with one or more as valence allows $Z^{1f}$; aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(b) —$C(O)R^{7a}$, —$C(O)OR^{7a}$, or $C(O)NR^{8a}R^{9a}$.

In another embodiment, the present invention is directed to compounds of formula (I) wherein
$R^{7a}$ is independently selected from
(a) hydrogen, or
(b) alkyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$.

In another embodiment, the present invention is directed to compounds of formula (I) wherein
$Z^{1b}$, $Z^{2b}$ and $Z^{3b}$ are optional substituents independently selected from alkyl, heteroaryl, —OH, —O—$Y^5$, —$U^1$—$NY^2Y^3$, —$C(O)_tH$, —$C(O)_tY^5$;
$Z^{1c}$ is
(a) —OH, —O—$Y^5$ or
(b) aryl optionally substituted with —OH or —$OY^5$;
$Z^{1d}$, $Z^{2d}$ and $Z^{3d}$ are optional substituents independently selected from
(a) cyano, halo, —OH, —O—$Y^5$, —$U^1$—$NY^2Y^3$, —$C(O)_tH$, —$C(O)_tY$, —$S(O)_tY^5$;
(b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$-heteroaryl.

In another embodiment, the present invention is directed to compounds of formula (I) wherein
$R^3$ is hydrogen;
$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$;
alternatively, $R^3$ and $R^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1b}$, $Z^{2b}$ and $Z^{3b}$;
$R^6$ is
(a) alkynyl optionally substituted with $Z^{1d}$ where $Z^{1d}$ is aryl which may be further optionally independently substituted with one or more cyano, halo, —OH, —OY, —$U^1$—$NY^2Y^3$, —$C(O)_tH$, —$C(O)_tY$, or, —$S(O)_tY$; or
(b) aryl optionally independently substituted as valence allows with one or more $Z^{1d}$, $Z^{2d}$ and $Z^{3d}$;
where
$U^1$ is a bond or alkylene;
$Z^{1c}$ is
(a) —OY where Y is aryl, or
(b) aryl optionally substituted with —OH or —OY where Y is alkyl;
$Z^{1d}$, $Z^{2d}$ and $Z^{3d}$ are optional substituents independently selected from
(a) cyano, halo, —OH, —OY, —$C(O)_tH$, —$C(O)_tY$, —$S(O)_tY$, or
(b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—$C(O)$—$Y^1$, —$U^1$—$N(Y^4)$—$C(O)$—$Y^1$, or —$U^1$—$N(Y^4)$—$S(O)_2$—$Y^1$,
where
$U^1$ is a bond or alkylene.

In another embodiment, the present invention is directed to compounds of formula (I) wherein
$R^1$ is alkyl; and
$R^2$ is hydrogen.

In another embodiment, the present invention is directed to compounds of formula (I) wherein
$R^5$ is selected from
a) hydrogen, or
(b) alkyl, alkenyl, alkynyl, and haloalkyl, any of which may be optionally independently substituted as valence allows with one or more $Z^{1b}$, $Z^{2b}$ and $Z^{3b}$;

R⁶ is

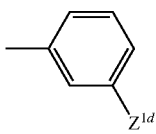

which may be further substituted with with one or more $Z^{1d}$, $Z^{2d}$ and $Z^{3d}$.

In another embodiment, the present invention is directed to compounds of formula (I) wherein

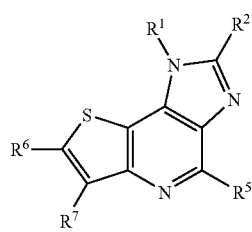

(I)

enantiomers, diastereomers, salts, and solvates thereof wherein $R^1$ is selected from hydrogen, $C_{1-3}$ alkyl, $C_{2-3}$ alkenyl, and $C_{2-3}$ alkynyl;

$R^2$ is hydrogen, alkyl, alkenyl, alkynyl, haloalkyl, $R^5$ is selected from
a) hydrogen and halo,
(b) alkyl, alkenyl, alkynyl, and haloalkyl, any of which may be optionally independently substituted as valence allows with one or more $Z^{1b}$, $Z^{2b}$ and $Z^{3b}$;
(c) —$OR^{11}$, —$SR^{11}$ and —$NR^3R^4$;

$R^3$ and $R^4$ are independently selected from
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1b}$, $Z^{2b}$ and $Z^{3b}$;
(c) —$OR^{11}$, —$NR^{12}R^{13}$, —$N(R^{12})C(O)R^{14}$, —$N(R^{12})C(O)OR^{14}$, —$N(R^{12})SO_2R^{14}$, —$N(R^{12})C(O)NR^{12a}R^{13}$, or —$N(R^{12})SO_2NR^{12a}R^{13}$ or —$C(O)OR^{14}$, —$C(O)R^{11}$, —$C(O)NR^{12}R^{13}$, —$SO_2R^{14}$, —$SO_2NR^{12}R^{13}$;
(d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;

$R^6$ is
(a) alkyl, alkenyl, alkynyl, any of which is substituted with one or more as valence allows $Z^{1f}$; cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(b) —$SR^{7a}$, —$SO_2R^{10}$, —$SO_2NR^{8b}R^{9b}$, $C(O)R^{7a}$, —$C(O)OR^{7a}$, or —$C(O)NR^{8a}R^{9a}$;

$R^7$ is
(a) hydrogen, hydroxy, halo, or cyano,
(b) alkyl, alkenyl, alkynyl, haloalkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(c) -, —$SR^{7a}$, —$SO_2R^{10}$, —$SO_2NR^{8b}R^{9b}$, —$C(O)R^{7a}$, —$C(O)OR^{7a}$, or —$C(O)NR^{8a}R^{9a}$;

$R^{7a}$ and $R^{7b}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1c}$, $Z^{2c}$ and $Z^{3c}$;

$R^{8a}$, $R^{8b}$, $R^{9a}$ and $R^{9b}$ are independently
(a) hydrogen,
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;
(c) $R^{8a}$ and $R^{9a}$ together with the nitrogen atom to which they are attached combine to form a 3 to 8 membered heterocyclic ring optionally independently substituted as valence allows with one or more $Z^{1b}$, $Z^{2b}$ and $Z^{3b}$; or
(d) $R^{8b}$ and $R^{9b}$ together with the nitrogen atom to which they are attached combine to form a 3 to 8 membered heterocyclic ring optionally independently substituted as valence allows with one or more $Z^{1b}$, $Z^{2b}$ and $Z^3$;

$R^{10}$, at each occurance, is independently alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1d}$, $Z^{2d}$ and $Z^{3d}$;

$R^{11}$, $R^{12}$, $R^{12a}$ and $R^{13}$ are independently
(a) hydrogen, or
(b) alkyl, alkenyl, alkynyl, haloalkyl, cycloalkyl, (cycloalkyl)alkyl, aryl, (aryl)alkyl, heterocyclo, (heterocyclo)alkyl, heteroaryl, or (heteroaryl)alkyl any of which may be optionally independently substituted as valence allows with one or more $Z^{1e}$, $Z^{2e}$ and $Z^{3e}$;

$R^{14}$ is alkyl, alkenyl, alkynyl, haloalkyl, cycloalkyl, (cycloalkyl)alkyl, aryl, (aryl)alkyl, heterocyclo, (heterocyclo) alkyl, heteroaryl, or (heteroaryl)alkyl any of which may be optionally independently substituted as valence allows with one or more $Z^{1e}$, $Z^{2e}$ and $Z^{3e}$;

$Z^{1a-1e}$, $Z^{2a-2e}$, and $Z^{3a-3e}$ are optional substituents at each occurrence independently selected from —$W^1$—$V^1$; —$W^2$—$V^2$; —$W^3$—$V^3$; —$W^4$—$V^4$; —$W^5$—$V^5$;

where $W^{1-5}$ are independently
(1) a bond
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo) alkyl, heteroaryl, or (heteroaryl)alkyl, any of which may be optionally independently substituted as valence allows with one or more $V^{1-5}$; or where $V^{1-5}$ are independently
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo) alkyl, heteroaryl, or (heteroaryl)alkyl, any of which may be optionally independently substituted as valence allows with one or more of groups (3)-(25) of $V^{1-5}$;
(3) —$U^1$—O—$Y^5$,
(4) —$U^1$—S—$Y^5$,
(5) —$U^1$—C(O)$_t$—H, —$U^1$—C(O)$_t$—$Y^5$ where t is 1 or 2,
(6) —$U^1$—SO$_3$—H, or —$U^1$—S(O)$_t Y^5$, (7) —$U^1$-halo,
(8) —$U^1$-cyano,
(9) —$U^1$-nitro,
(10) —$U^1$—$NY^2Y^3$,
(11) —$U^1$—$N(Y^4)$—$C(O)$—$Y^1$,
(12) —$U^1$—$N(Y^4)$—$C(S)$—$Y^1$,
(13) —$U^1$—$N(Y^4)$—$C(O)$—$NY^2Y^3$,
(14) —$U^1$—$N(Y^4)$—$C(S)$—$NY^2Y^3$,
(15) —$U^1$—$N(Y^4)$—$C(O)O$—$Y^5$,
(16) —$U^1$—$N(Y^4)$—$S(O)_2$—$Y^1$,
(17) —$U^1$—$N(Y^4)$—$S(O)_2$—$NY^2Y^3$,
(18) —$U^1$—$C(O)$—$NY^2Y^3$,
(19) —$U^1$—$OC(O)$—$NY^2Y^3$
(20) —$U^1$—$S(O)_2$—$N(Y^4)$—$Y^1$,
(21) —$U^1$—$N(Y^4)$—$C(=NV^{1a})$—$NY^2Y^3$,
(22) —$U^1$—$N(Y^4)$—$C(=NV^{1a})$—$Y^1$,
(23) —$U^1$—$C(=NV^{1a})$—$NY^2Y^3$,
(24) oxo;
(25) —$U^1$—$Y^5$;

$Z^{1f}$, at each occurrence, is independently selected from
(1) cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, optionally substituted as valence allows with one or more of groups (2) to (25) of $Z^{1f}$;
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^5$,
(4) —$U^1$—S—$Y^5$,
(5) —$U^1$—$C(O)_t$—H, —$U^1$—$C(O)_t$—$Y^5$ where t is 1 or 2,
(6) —$U^1$—$SO_3$—H, or —$U^1$—$S(O)_tY^5$,
(7) —$U^1$-halo,
(8) —$U^1$-cyano,
(9) —$U^1$-nitro,
(10) —$U^1$—$NY^2Y^3$,
(11) —$U^1$—$N(Y^4)$—$C(O)$—$Y^1$,
(12) —$U^1$—$N(Y^4)$—$C(S)$—$Y^1$,
(13) —$U^1$—$N(Y^4)$—$C(O)$—$NY^2Y^3$,
(14) —$U^1$—$N(Y^4)$—$C(S)$—$NY^2Y^3$,
(15) —$U^1$—$N(Y^4)$—$C(O)O$—$Y^5$,
(16) —$U^1$—$N(Y^4)$—$S(O)_2$—$Y^1$,
(17) —$U^1$—$N(Y^4)$—$S(O)_2$—$NY^2Y^3$,
(18) —$U^1$—$C(O)$—$NY^2Y^3$,
(19) —$U^1$—$OC(O)$—$NY^2Y^3$
(20) —$U^1$—$S(O)_2$—$N(Y^4)$—$Y^1$,
(21) —$U^1$—$N(Y^4)$—$C(=NV^{1a})$—$NY^2Y^3$,
(22) —$U^1$—$N(Y^4)$—$C(=NV^{1a})$—$Y^1$,
(23) —$U^1$—$C(=NV^{1a})$—$NY^2Y^3$,
(24) oxo;
(25) —$U^1$—$Y^5$;

$V^{1a}$ is independently hydrogen, alkyl, —CN, —$C(O)Y^1$, —$S(O)_2Y^5$, $S(O)_2NY^2Y^3$;

$Y^1, Y^2, Y^3, Y^4$ and $Y^5$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl, any of which may be optionally independently substituted as valence allows with one or more $Z^4, Z^5$ and $Z^6$; or
(2) $Y^2$ and $Y^3$ may together be alkylene or alkenylene, completing a 3- to 8-membered saturated or unsaturated ring together with the atoms to which they are attached, or (4) $Y^2$ and $Y^3$ together with the nitrogen atom to which they are attached may combine to form a group —N=$CY^6Y^7$ where $Y^6$ and $Y^7$ are each independently H or alkyl; and $Z^4, Z^5$, and $Z^6$ are optional substituents at each occurrence independently selected from
(1) H
(2) alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;
(3) —$U^1$—O—$Y^{5a}$,
(4) —$U^1$—S—$Y^{5a}$,
(5) —$U^1$—$C(O)_t$—H, —$U^1$—$C(O)_t$—$Y^{5a}$ where t is 1 or 2,
(6) —$U^1$—$SO_3$—H, or —$U^1$—$S(O)_tY^{5a}$,
(7) —$U^1$-halo,
(8) —$U^1$-cyano,
(9) —$U^1$-nitro,
(10) —$U^1$—$NY^{2a}Y^{3a}$,
(11) —$U^1$—$N(Y^{4a})$—$C(O)$—$Y^{1a}$,
(12) —$U^1$—$N(Y^{4a})$—$C(S)$—$Y^{1a}$,
(13) —$U^1$—$N(Y^{4a})$—$C(O)$—$NY^{2a}Y^{3a}$,
(14) —$U^1$—$N(Y^{4a})$—$C(S)$—$NY^{2a}Y^{3a}$,
(15) —$U^1$—$N(Y^{4a})$—$C(O)O$—$Y^{5a}$,
(16) —$U^1$—$N(Y^{4a})$—$S(O)_2Y^{1a}$,
(17) —$U^1$—$N(Y^{4a})$—$S(O)_2$—$NY^{2a}Y^{3a}$,
(18) —$U^1C(O)$—$NY^{2a}Y^{3a}$,
(19) —$U^1$—$OC(O)$—$NY^{2a}Y^{3a}$
(20) —$U^1$—$S(O)_2$—$N(Y^{4a})$—$Y^{1a}$,
(21) —$U^1$—$N(Y^{4a})$—$C(=NV^{1a})$—$NY^{2a}Y^{3a}$,
(22) —$U^1$—$N(Y^{4a})$—$C(=NV^{1a})$—$Y^{1a}$,
(23) —$U^1$—$C(=NV^{1a})$—$NY^{2a}Y^{3a}$,
(24) oxo;
(25) —$U^1$—$Y^{5a}$;

$Y^{1a}, Y^{2a}, Y^{3a}, Y^{4a}$ and $Y^{5a}$
(1) are each independently hydrogen, alkyl, (hydroxy)alkyl, (alkoxy)alkyl, alkenyl, alkynyl, cycloalkyl, (cycloalkyl)alkyl, cycloalkenyl, (cycloalkenyl)alkyl, aryl, (aryl)alkyl, heterocyclo, (heterocyclo)alkyl, heteroaryl, or (heteroaryl)alkyl;

$U^1$ is independently
(1) a single bond,
(2) alkylene,
(3) alkenylene, or
(4) alkynylene.

In another embodiment, the present invention is directed to compounds of formula (I), wherein
$R^6$ is
(a) alkynyl optionally substituted with $Z^{1d}$ where $Z^{1d}$ is aryl which may be further optionally independently substituted with one or more cyano, halo, —OH, —OY, —$U^1$—$NY^2Y^3$, —$C(O)_tH$, —$C(O)_tY$, or, —$S(O)_tY$; or
(b) aryl optionally independently substituted as valence allows with one or more $Z^{1d}, Z^{2d}$ and $Z^{3d}$.

In another embodiment, the present invention is directed to compounds of formula (I), wherein
$R^6$ is phenyl optionally independently substituted as valence allows with one or more $Z^{1d}, Z^{2d}$ and $Z^{3d}$.

In another embodiment, the present invention is directed to compounds of formula (I), wherein
$R^1$ is hydrogen, methyl, ethyl, propyl, i-propyl, prop-2-enyl, prop-1-enyl; and
$R^2$ is hydrogen, methyl, and trifluoromethyl.

In another embodiment, the present invention is directed to compounds of formula (I), wherein
$R^7$ is hydrogen, hydroxy, halo, or alkyl;
$R^3$ and $R^4$ are independently selected from
(a) alkyl which may be optionally independently substituted as valence allows with one or more $Z^{1b}$, $Z^{2b}$ and $Z^{3b}$; or
(b) —C(O)OR$^{14}$, —C(O)R$^{11}$, —C(O)NR$^{12}$R$^{13}$, —SO$_2$R$^{14}$, —SO$_2$NR$^{12}$R$^{13}$.

In another embodiment, the present invention is directed to compounds of formula (I), wherein
$Z^{1d}$, $Z^{2d}$ and $Z^{3d}$ are optional substituents independently selected from
(a) cyano, halo, —OH, —OY, —C(O)$_t$H, —C(O)$_t$Y, —S(O)$_t$Y, or
(b) alkyl or alkoxy optionally substituted with one or more cyano, halo, —OH, —OY, —U$^1$—NY$^2$Y$^3$, —C(O)$_t$H, —C(O)$_t$Y, —S(O)$_t$Y, —U$^1$—N(Y$^4$)—C(O)—Y$^1$, —U$^1$—N(Y$^4$)—C(O)O—Y$^1$, or —U$^1$—N(Y$^4$)—S(O)$_2$—Y$^1$,
where U$^1$ is a bond or alkylene.

In another embodiment, the present invention is directed to compounds of formula (I), wherein
$R^6$ is

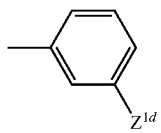

which may be further substituted with with one or more $Z^{1d}$, $Z^{2d}$ and $Z^{3d}$.

In another embodiment, the present invention is directed to compounds of formula (I) wherein the compounds are selected from the compounds of the Examples.

The invention also relates to pharmaceutical compositions containing at least one compound of formula (I) and a pharmaceutically-acceptable carrier or diluent, for use in treating inflammatory and immune diseases or cancer. Also included within the invention are methods of treating such diseases comprising administering to a mammal in need of such treatment an effective amount of at least one compound of formula (I).

In another embodiment, $R^6$ is phenyl substituted with 0-3 $Z^{1d}$, $Z^{2d}$ and $Z^{3d}$.

In another embodiment, $R^6$ is —SR$^{7a}$, —SO$_2$R$^{10}$, —SO$_2$NR$^{8b}$R$^{9b}$, C(O)R$^{7a}$, —C(O)OR$^{7a}$, or —C(O)NR$^{8a}$R$^{9a}$.

In another embodiment, $R^1$ is hydrogen, methyl, or ethyl.
In another embodiment, $R^2$ is hydrogen.
In another embodiment, $R^1$ is selected from hydrogen, $C_{1-3}$ alkyl, and $C_{2-3}$ alkenyl; and $R^2$ is hydrogen, alkyl, haloalkyl, or aryl.

In another embodiment, $R^3$ and $R^4$ are independently selected from
(a) hydrogen,
(b) alkyl, haloalkyl, (hydroxy)alkyl, cycloalkyl, (cycloalkyl)alkyl, (heterocyclo)alkyl, (aryl)alkyl or (heteroaryl)alkyl any of which may be optionally independently substituted as valence allows with one or more $Z^{1b}$, $Z^{2b}$ and $Z^{3b}$;
(c) —NR$^{12}$R$^{13}$; or
(d) $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$.

In another embodiment, $R^3$ and $R^4$ are independently selected from
(a) alkyl which may be optionally independently substituted as valence allows with one or more $Z^{1b}$, $Z^{2b}$ and $Z^{3b}$; or
(b) —C(O)OR$^{14}$, —C(O)R$^{11}$, —C(O)NR$^{12}$R$^{13}$, —SO$_2$R$^{14}$, —SO$_2$NR$^{12}$R$^{13}$.

In another embodiment, $R^3$ and $R^4$ are independently selected from
(a) alkyl which may be optionally independently substituted as valence allows with one or more $Z^{1b}$, $Z^{2b}$ and $Z^{3b}$; or
wherein $Z^{1b}$, $Z^{2b}$ and $Z^{3b}$ is H, heterocyclo, heteroaryl, any of which may be optionally independently substituted as valence allows with one or more $Z^4$, $Z^5$ and $Z^6$; or —U$^1$—NY$^2$Y$^3$,
(b) —C(O)OR$^{14}$, —C(O)R$^{11}$, —C(O)NR$^{12}$R$^{13}$, —SO$_2$R$^{14}$, —SO$_2$NR$^{12}$R$^{13}$.

In another embodiment, $R^3$ and $R^4$ are independently selected from hydrogen, alkyl, (hydroxy)alkyl, or (heteroaryl)alkyl any of which may be optionally independently substituted as valence allows with 1-2 $Z^{1b}$, $Z^{2b}$ and $Z^{3b}$; —NR$^{12}$R$^{13}$; or $R^3$ and $R^4$ together with the nitrogen atom to which they are attached combine to form a 3 to 8 membered heterocyclic ring optionally independently substituted as valence allows with one or more $Z^{1b}$, $Z^{2b}$ and $Z^{3b}$;
$Z^{1b}$, $Z^{2b}$ and $Z^{3b}$ are selected from hydrogen, alkyl, —U$^1$—O—Y$^5$, —U$^1$, —NY$^2$Y$^3$, and
U$^1$ is a single bond or alkylene,
In another embodiment $R^5$ is selected from —NR$^3$R$^4$.

In another embodiment,
$R^5$ is selected from
a) hydrogen, or
(b) alkyl, alkenyl, alkynyl, and haloalkyl, any of which may be optionally independently substituted as valence allows with one or more $Z^{1b}$, $Z^{2b}$ and $Z^{3b}$;
$R^6$ is

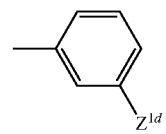

which may be further substituted with with one or more $Z^{1d}$, $Z^{2d}$ and $Z^{3d}$.

In another embodiment, $Y^5$ is H or alkyl, wherein the alkyl is selected from methyl, ethyl, propyl, i-propyl, butyl, i-butyl, t-butyl, pentyl, and hexyl;
$Y^2$ and $Y^3$ are independently selected from alkyl wherein the alkyl is selected from methyl, ethyl, propyl, i-propyl, butyl, i-butyl, t-butyl, pentyl, and hexyl.

In another embodiment, $R^3$ and $R^4$ are independently selected from hydrogen, alkyl, wherein the alkyl is selected from methyl, ethyl, propyl, i-propyl, butyl, i-butyl, t-butyl, pentyl, and hexyl; (hydroxy)alkyl, or (heteroaryl)alkyl, wherein (heteroaryl)alkyl is (tetrazolyl)methyl; any of which may be optionally independently substituted with 1 $Z^{1b}$; —NR$^{12}$R$^{13}$; or $R^3$ and $R^4$ together with the nitrogen atom to which they are attached combine to form a 3 to 8 membered heterocyclic ring, wherein the ring is selected from piperidinyl, and morpholinyl, optionally independently substituted with 1 $Z^{1b}$.

In another embodiment, $R^3$ is hydrogen;

$R^4$ is alkyl, haloalkyl, (hydroxy)alkyl, cycloalkyl, (cycloalkyl)alkyl, (heterocyclo)alkyl, (aryl)alkyl or (heteroaryl)alkyl and of which may be optionally independently substituted as valence allows with one or more $Z^{1b}$, $Z^{2b}$ and $Z^{3b}$;

alternatively, $R^3$ and $R^4$ together with the nitrogen atom to which they are attached combine to form a 3 to 6 membered heterocyclic ring selected from piperidinyl, morpholinyl, pyrrolidinyl, and azetidinyl; optionally independently substituted as valence allows with one or more $Z^{1b}$, $Z^{2b}$ and $Z^{3b}$.

In another embodiment, $R^6$ is
(a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(b) —$SR^{7a}$, —$SO_2R^{10}$, —$SO_2NR^{8b}R^{9b}$, $C(O)R^{7a}$, —$C(O)OR^{7a}$, or —$C(O)NR^{8a}R^{9a}$.

In another embodiment, $R^6$ is
(a) alkyl, cycloalkyl, heterocyclo, aryl, heteroaryl, (cycloalkyl)alkyl, (heterocyclo)alkyl, (aryl)alkyl, or (heteroaryl)alkyl any of which may be optionally independently substituted as valence allows with one or more $Z^{1d}$, $Z^{2d}$ and $Z^{3d}$; or
(b) —$SR^{7a}$, —$SO_2R^{10}$, —$SO_2NR^{8b}R^{9b}$, $C(O)R^{7a}$, —$C(O)OR^{7a}$, or —$C(O)NR^{8a}R^{9a}$;

wherein $Z^{1d}$, $Z^{2d}$ and $Z^{3d}$ is —$W^4$—$V^4$; where $W^4$ is
(1) a bond
(2) alkyl, (hydroxy)alkyl, alkenyl, haloalkyl, heteroaryl, or (heteroaryl)alkyl; and where $V^4$ is
(1) H
(2) aryl, (aryl)alkyl, heterocyclo, (heterocyclo)alkyl, heteroaryl, or (heteroaryl)alkyl;
(3) —$U^1$—O—$Y^5$,
(4) —$U^1$—$C(O)_t$—H, —$U^1$—$C(O)_t$—$Y^5$ where t is 1 or 2,
(5) —$U^1$—$SO_3$—H, or —$U^1$—$S(O)_tY^5$,
(6) —$U^1$-halo,
(7) —$U^1$—$NY^2Y^3$,
(8) —$U^1$—$N(Y^4)$—$C(O)$—$Y^1$,
(8) —$U^1$—$N(Y^4)$—$C(O)$—$NY^2Y^3$,
(10) —$U^1$—$N(Y^4)$—$C(O)O$—$Y^5$,
(11) —$U^1$—$N(Y^4)$—$S(O)_2$—$Y^1$,
(12) —$U^1$—$N(Y^4)$—$S(O)_2$—$NY^2Y^3$,
(13) —$U^1$—$C(O)$—$NY^2Y^3$,
(14) —$U^1$—$OC(O)$—$NY^2Y^3$
(15) —$U^1$—$S(O)_2$—$N(Y^4)$—$Y^1$; and $U^1$ is a bond.

In another embodiment, the present invention is directed to compounds of formula (I) wherein
$R^6$ is

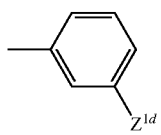

which may be further substituted with with one or more $Z^{1d}$, $Z^{2d}$ and $Z^{3d}$.

In another embodiment, $R^6$ is
(a) alkynyl optionally substituted with $Z^{1d}$ where $Z^{1d}$ is aryl which may be further optionally independently substituted with one or more cyano, halo, —OH, —OY, —$U^1$—$NY^2Y^3$, —$C(O)_tH$, —$C(O)_tY$, or, —$S(O)_tY$;
(b) aryl optionally independently substituted as valence allows with one or more $Z^{1d}$, $Z^{2d}$ and $Z^{3d}$; or
(c) —$SR^{7a}$, —$SO_2R^{10}$ or —$SO_2NR^{8b}R^{9b}$;
$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$U^1$—$N(Y^4)$—$C(O)$—$Y^1$, or —$U^1$—$N(Y^4)$—$C(O)O$—$Y^5$.

In another embodiment
$R^6$ is
(a) alkynyl optionally substituted with $Z^{1d}$ where $Z^{1d}$ is aryl which may be further optionally independently substituted with one or more cyano, halo, —OH, —OY, —$U^1$—$NY^2Y^3$, —$C(O)_tH$, —$C(O)_tY$, or, —$S(O)_tY$;
(b) aryl optionally independently substituted as valence allows with one or more $Z^{1d}$, $Z^{2d}$ and $Z^{3d}$; or
(c) —$SR^{7a}$, —$SO_2R^{10}$, or —$SO_2NR^{8b}R^{9b}$;
$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$U^1$—$N(Y^4)$—$C(O)$—$Y^1$, or —$U^1$—$N(Y^4)$—$C(O)O$—$Y^5$, where
$U^1$ is a bond or alkylene;
$Z^{1c}$ is
(a) —OY where Y is aryl, or
(b) aryl optionally substituted with —OH or —OY where Y is alkyl;
$Z^{1d}$, $Z^{2d}$ and $Z^{3d}$ are optional substituents independently selected from
(a) cyano, halo, —OH, —OY, —$C(O)_tH$, —$C(O)_tY$, —$S(O)_tY$, or
(b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—$C(O)$—$Y^1$, —$U^1$—$N(Y^4)$—$C(O)$—$Y^1$, or —$U^1$—$N(Y^4)$—$S(O)_2$—$Y^1$, where $U^1$ is a bond or alkylene.

In another embodiment
$R^6$ is
(a) alkynyl optionally substituted with $Z^{1d}$ where $Z^{1d}$ is phenyl which may be further optionally independently substituted with 0-1 cyano, halo, —OH, —OY, —$U^1$—$NY^2Y^3$, —$C(O)_tH$, —$C(O)_tY$, or, —$S(O)_tY$;
(b) phenyl optionally independently substituted as valence allows with one or more $Z^{1d}$, $Z^{2d}$ and $Z^{3d}$; or
(c) —$SR^{7a}$;
$Z^{1b}$, $Z^{2b}$ and $Z^{3b}$ are optional substituents independently selected from —OH, —OY, —$U^1$—$NY^2Y^3$, —$C(O)_tH$, —$C(O)_tY$, —$U^1$—$N(Y^4)$—$C(O)$—$Y^1$, or —$U^1$—$N(Y^4)$—$C(O)O$—$Y^5$, where
$U^1$ is a bond or alkylene, wherein alkylene is selected from methylene, ethylene, propylene, and butylene;
$Z^{1c}$ is
(a) —OY where Y is phenyl, or
(b) phenyl optionally substituted with 0-1 —OH or —OY where Y is alkyl selected from methyl, ethyl, propyl, i-propyl, butyl, i-butyl, t-butyl, pentyl, hexyl;
$Z^{1d}$, $Z^{2d}$ and $Z^{3d}$ are optional substituents independently selected from
(a) cyano, halo, —OH, —OY, —$C(O)_tH$, —$C(O)_tY$, —$S(O)_tY$, or
(b) alkyl or alkoxy optionally substituted with one or more cyano, halo, —OH, —OY, —$U^1$—$NY^2Y^3$, —$C(O)_tH$, —$C(O)_tY$, —$S(O)_tY$, —$U^1$—$N(Y^4)$—$C(O)$—$Y^1$, —$U^1$—$N(Y^4)$—$C(O)$—$Y^1$ or —$U^1$—$N(Y^4)$—$S(O)_2$—$Y^1$, where $U^1$ is a bond or alkylene, wherein alkylene is selected from methylene, ethylene, propylene, and butylene.

In another embodiment, $Y^1$, $Y^2$, $Y^3$, and $Y^4$ are independently selected from hydrogen, alkyl, wherein alkyl is selected from alkyl is selected from methyl, ethyl, propyl, i-propyl, butyl, i-butyl, t-butyl, pentyl, and hexyl; aryl wherein aryl is phenyl, (aryl)alkyl.

In another embodiment, the present invention is directed to a compound of Formula (I), wherein the compound is selected from the compounds of the Examples or of Tables.

In another embodiment, the present invention is directed to a pharmaceutical composition, comprising a pharmaceutically acceptable carrier and a therapeutically effective amount of a compound of Formula (I).

In another embodiment, the present invention is directed to a method of treating an inflammatory or immune disease or disorder comprising administering to a mammal in need thereof a therapeutically-effective amount of at least one compound of formula (I).

In another embodiment, the present invention is directed to a method of treating cancer comprising administering to a mammal in need thereof a therapeutically-effective amount of at least one compound of formula (I)

In another embodiment, the present invention is directed to a method of treating an inflammatory or immune disease or disorder selected from, rheumatoid arthritis, asthma, inflammatory bowel disease, chronic obstructive pulmonary disease, and psoriasis.

In another embodiment, the present invention is directed the use of a compound of Formula (I) in the preparation of a medicament for the treatment of an inflammatory or immune disease.

In another embodiment, the present invention is directed the use of a compound of Formula (I) in the preparation of a medicament for the treatment of cancer.

In another embodiment, the present invention is directed to the use of a compound of Formula (I) in the preparation of a medicament for the treatment of an inflammatory or immune disease.

In another embodiment, the present invention is directed to the use of a compound of Formula (I) in the preparation of a medicament for the treatment of cancer.

In another embodiment, the present invention is directed to the use of a compound of Formula (I) in the preparation of a medicament for the treatment of an inflammatory or immune disease, wherein the disease is selected from, rheumatoid arthritis, asthma, inflammatory bowel disease, chronic obstructive pulmonary disease, and psoriasis.

In another embodiment, the present invention is directed to the use of a compound of Formula (I) for use in therapy.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment are meant to be combined with any and all other elements from any of the embodiments to describe additional embodiments.

DEFINITIONS

The following are definitions of terms used in this specification. The initial definition provided for a group or term herein applies to that group or term throughout the present specification, individually or as part of another group, unless otherwise indicated.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substitent is keto (i.e., =O), then 2 hydrogens on the atom are replaced. The term "optionally independently substituted as valence allows", as used herein, means that the any one or more hydrogens on the designated variable is independently replaced with a selection from the indicated group, provided that the designated variable's normal valency is not exceeded, and that the substitution results in a stable compound.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "alkyl" as used herein by itself or as part of another group refers to straight and branched chain hydrocarbons, containing 1 to 20 carbons, alternatively, 1 to 10 carbons, or 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like. Lower alkyl groups, that is, alkyl groups of 1 to 4 carbon atoms, are an alternative embodiment.

"Halo" or "halogen" as used herein refers to fluoro, chloro, bromo, and iodo; and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

The term "alkenyl" as used herein by itself or as part of another group refers to straight or branched chain radicals of 2 to 20 carbons, alternatively, 2 to 12 carbons, or 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

The term "alkynyl" as used herein by itself or as part of another group refers to straight or branched chain hydrocarbon groups having 2 to 12 carbon atoms, alternatively, 2 to 4 carbon atoms, and at least one triple carbon to carbon bond, such as ethynyl, 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like.

When the term "alkyl" is used together with another group, such as in "(aryl)alkyl", this conjunction is meant to refer to a substituted alkyl group wherein at least one of the substituents is the specifically named group in the conjunction. For example, "(aryl)alkyl" refers to a substituted alkyl group as defined above wherein at least one of the substituents is an aryl, such as benzyl.

Where alkyl groups as defined above have single bonds for attachment to two other groups, they are termed "alkylene" groups. Similarly, where alkenyl groups as defined above and alkynyl groups as defined above, respectively, have single bonds for attachment to two other groups, they are termed "alkenylene groups" and "alkynylene groups" respectively. Examples of alkylene, alkenylene and alkynylene groups include:

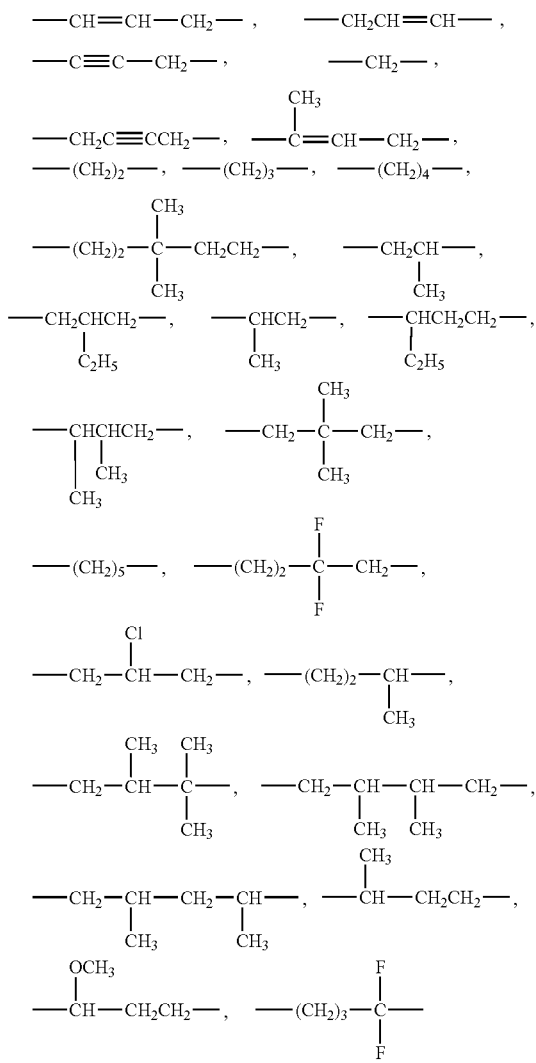

and the like. Alkylene groups may be optionally independently substituted as valence allows with one or more groups provided in the definition of $Z^1$.

The term "cycloalkyl" as used herein by itself or as part of another group refers to saturated and partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, alternatively, 3 to 7 carbons, forming the ring. The rings of multi-ring cycloalkyls may be either fused, bridged and/or joined through one or more spiro union to 1 or 2 aromatic, cycloalkyl or heterocyclo rings. Exemplary cycloalkyl groups include cyclopropyl, cyclobutyl, cyclopentyl, cyclohexyl, cycloheptyl, cyclooctyl, cyclodecyl, cyclododecyl, cyclopentenyl, cyclohexenyl, cycloheptenyl, cyclooctenyl, cyclohexadienyl, cycloheptadienyl,

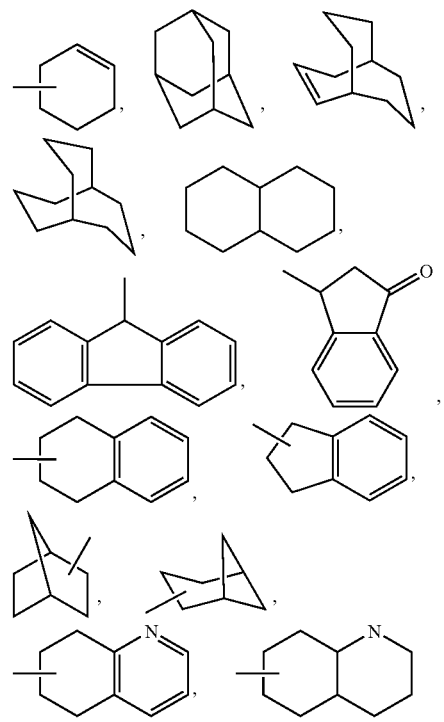

and the like.

The term "cycloalkylene" as employed herein refers to a "cycloalkyl" group which includes free bonds and thus is a linking group such as

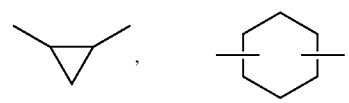

and the like.

One skilled in the field will understand that, when the designation "$CO_2$" is used herein, this is intended to refer to the group

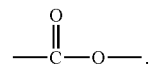

The term "alkoxy" refers to an alkyl or substituted alkyl group as defined above bonded through an oxygen atom (—O—), i.e., the groups —$OR_d$, wherein $R_d$ is alkyl or substituted alkyl.

The term "alkylthio" refers to an alkyl or substituted alkyl group as defined above bonded through a sulfur atom (—S—), i.e., the groups —SR$_d$, wherein R$_d$ is alkyl or substituted alkyl.

The term "acyl" refers to a carbonyl group linked to an organic radical, more particularly, the group C(=O)R$_g$, wherein R$_g$ can be selected from alkyl, alkenyl, substituted alkyl, or substituted alkenyl, as defined herein.

The term "alkoxycarbonyl" refers to a carboxy group

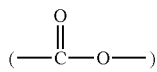

linked to an organic radical (CO$_2$R$_g$), wherein R$_g$ is as defined above for acyl.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes OCF$_3$.

The terms "ar" or "aryl" as used herein by itself or as part of another group refer to aromatic homocyclic (i.e., hydrocarbon) monocyclic, bicyclic or tricyclic aromatic groups containing 6 to 14 carbons in the ring portion (such as phenyl, biphenyl, naphthyl (including 1-naphthyl and 2-naphthyl) and antracenyl) and may optionally include one to three additional rings (either cycloalkyl, heterocyclo or heteroaryl) fused thereto. Examples include:

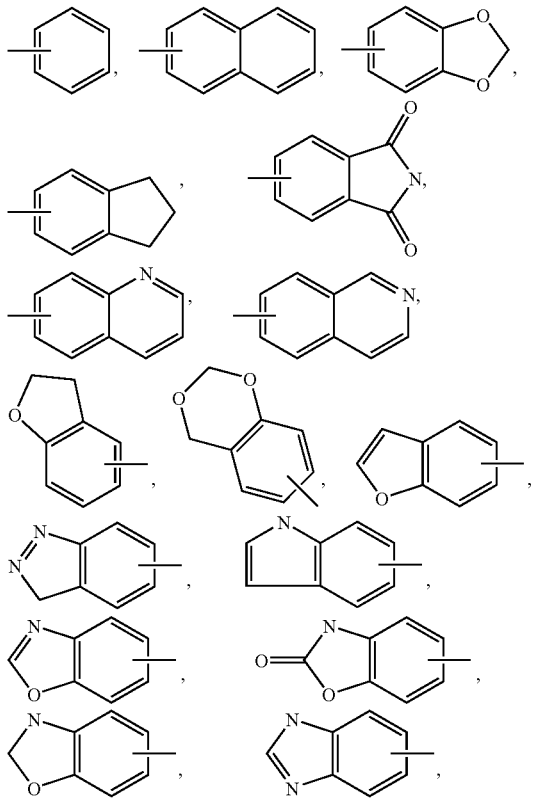

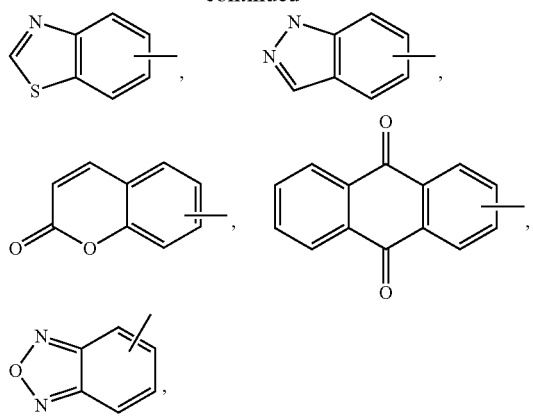

and the like.

The term "heteroaryl" as used herein by itself or as part of another group refers to monocyclic and bicyclic aromatic rings containing from 5 to 10 atoms, which includes 1 to 4 hetero atoms such as nitrogen, oxygen or sulfur, and such rings fused to an aryl, cycloalkyl, heteroaryl or heterocyclo ring, where the nitrogen and sulfur heteroatoms may optionally be oxidized and the nitrogen heteroatoms may optionally be quaternized. Examples of heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, carbazolyl, benzidolyl, phenanthrollinyl, acridinyl, phenanthridinyl, xanthenyl

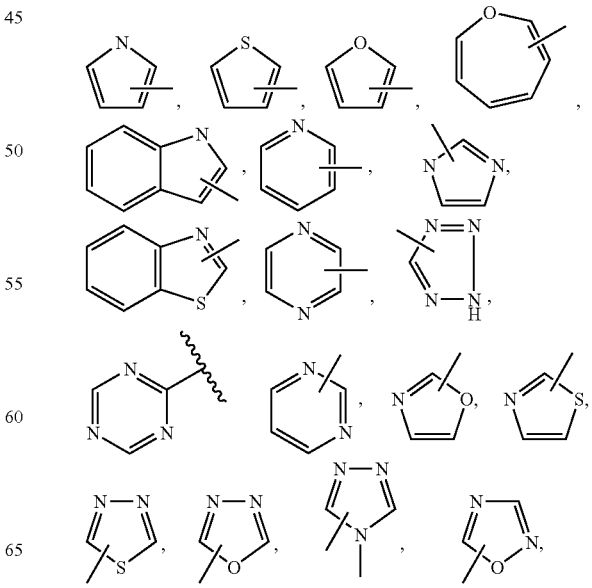

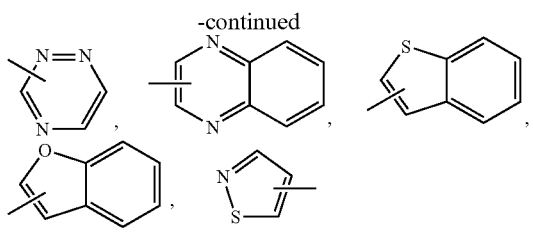

and the like.

In compounds of formula (I), heteroaryl groups include

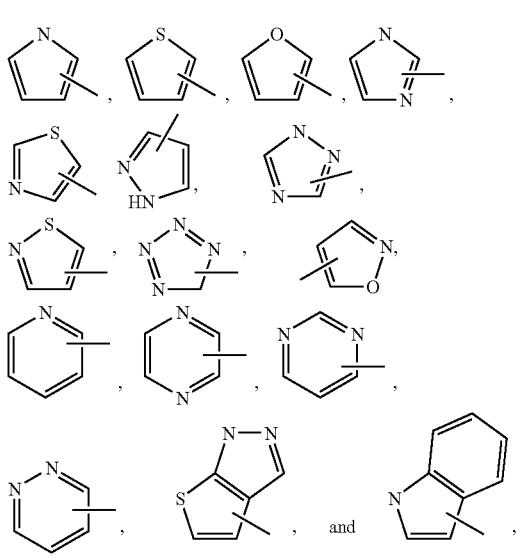

and the like, which optionally may be substituted at any available carbon or nitrogen atom.

The terms "heterocyclic" or "heterocyclo" as used herein by itself or as part of another group refer to optionally substituted, fully saturated or partially unsaturated cyclic groups (for example, 3 to 13 member monocyclic, 7 to 17 member bicyclic, or 10 to 20 member tricyclic ring systems, alternatively, containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valance allows. The rings of multi-ring heterocycles may be either fused, bridged and/or joined through one or more spiro unions. Exemplary heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl,

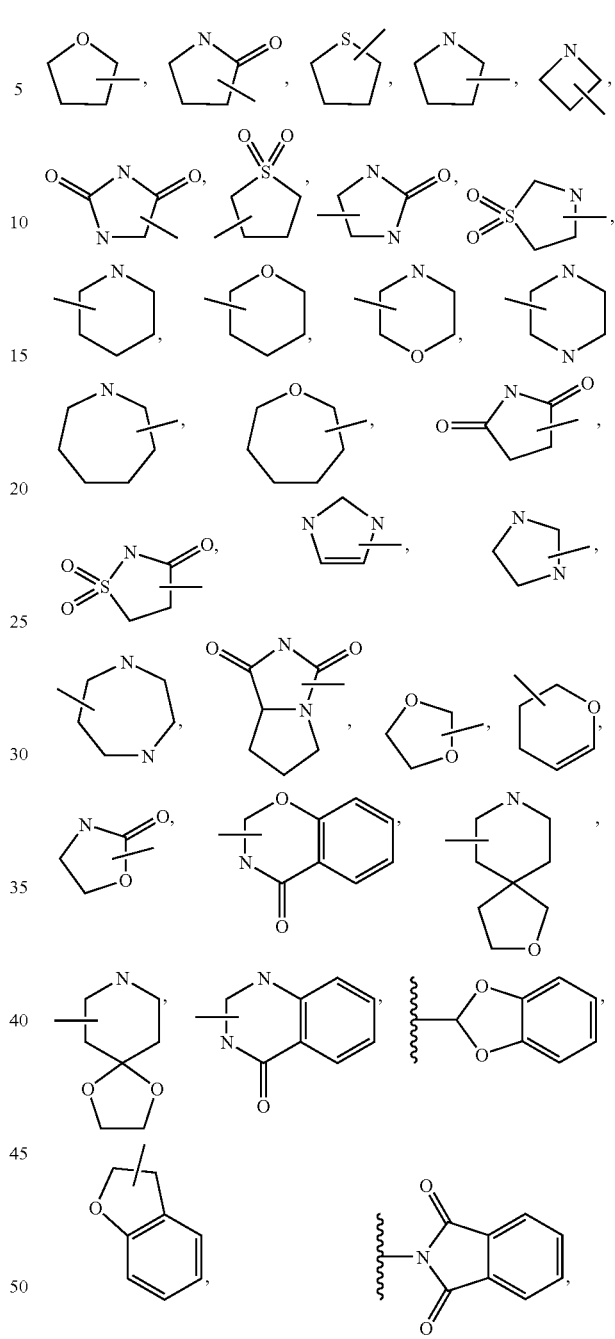

and the like.

Heterocyclo groups in compounds of formula (I) include

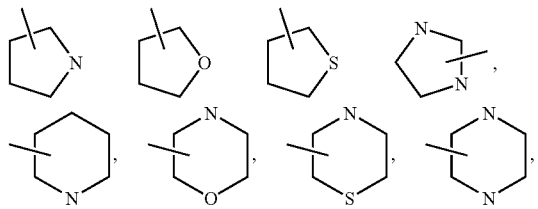

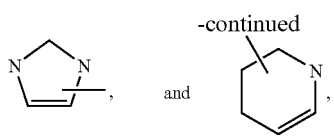

which optionally may be substituted.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl).

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, alternatively, 0 to 2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound of the formula I with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydroabietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g. benzyl and phenethyl bromides), and others.

Compounds of the formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, compounds of formula I may have prodrug forms. Any compound that will be converted in vivo to provide the bioactive agent (i.e., a compound of formula I) is a prodrug within the scope and spirit of the invention.

For example, pro-drug compounds of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:

a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);

b) *A Textbook of Drug Design and Development*, edited by Krosgaard-Larsen and H. Bundgaard, Chapter 5, *"Design and Application of Prodrugs,"* by H. Bundgaard, at pp. 113-191 (1991);

c) H. Bundgaard, *Advanced Drug Delivery Reviews*, Vol. 8, p. 1-38 (1992);

d) H. Bundgaard, et al., *Journal of Pharmaceutical Sciences*, Vol. 77, p. 285 (1988); and e) N. Kakeya, et. al., *Chem Phar Bull*, Vol. 32, p. 692 (1984).

It should further be understood that solvates (e.g., hydrates) of the compounds of formula I are also with the scope of the present invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to inhibit IKK or effective to treat or prevent inflammatory disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Methods of Preparation

Compounds of Formula I may be prepared by reference to the methods illustrated in the following Schemes I-III. As shown therein the end product is a compound having the same structural formula as Formula I. It will be understood that any compound of Formula I may be produced by Scheme I-III by the suitable selection of reagents with appropriate substitution. Solvents, temperatures, pressures, and other reaction conditions may readily be selected by one of ordinary skill in the art. All documents cited are incorporated herein by reference in their entirety. Starting materials are commercially available or readily prepared by one of ordinary skill in the art. Constituents of compounds are as defined herein or elsewhere in the specification.

The sequence described in Scheme I will produce compounds of Formula I. Nitration of 4-hydroxy pyridine, I-1 to provide the known compound I-2. followed by conversion to the corresponding known chloro-pyridine I-3. Subsequent addition of an amine such as methylamine provides compound I-4. Reduction of both nitro groups and simultaneous chlorination of the intermediate triaminopyridine occurs on treatment of I-4 with tin(II) chloride to produce I-5. This important intermediate can be reacted with triethyl orthoformate to provide fused imidazole I-6. Oxidation of the amine can be accomplished with a variety of reagents including aqueous hydrogen peroxide to produce nitro compound I-7. Regioselective displacement with an amine for example methylamine will produce I-8. The primary amine may be protected by reaction with ditert-butyl dicarbonate to produce I-9. Reaction of I-9 with an acetylene, such as phenylacetylene in the presence of a suitable palladium catalyst such as dichloropalladium bis-triphenylphosphine or tetrakis-triphenylphosphine palladium (0) will produce I-10. Reduction of the nitro group with tin chloride or zinc powder will provide I-11. The amine can be diazotized with isoamylnitrite and reacted with dimethyldisulfide to produce I-12. Cyclization to the tricyclic structure I-13 can be accomplished by treating I-12 with iodine. The Boc group is readily removed by treatment of I-13 with trifluoroacetic acid to produce I-14 which is a compound of Formula I. Reaction of I-14 with n-butyl lithium followed by quenching with aqueous ammonium chloride or reaction of I-14 with $H_2$ in the presence of a suitable catalyst such as palladium on carbon, or platinum oxide will produce I-15 which is also a compound of Formula I.

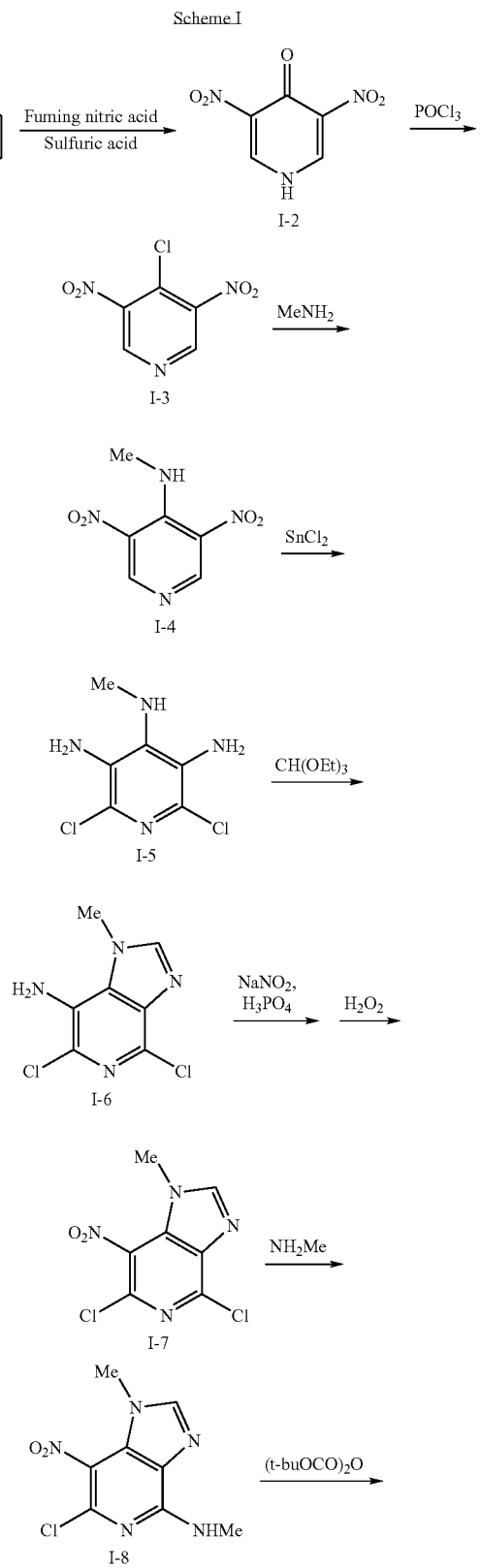

Scheme I

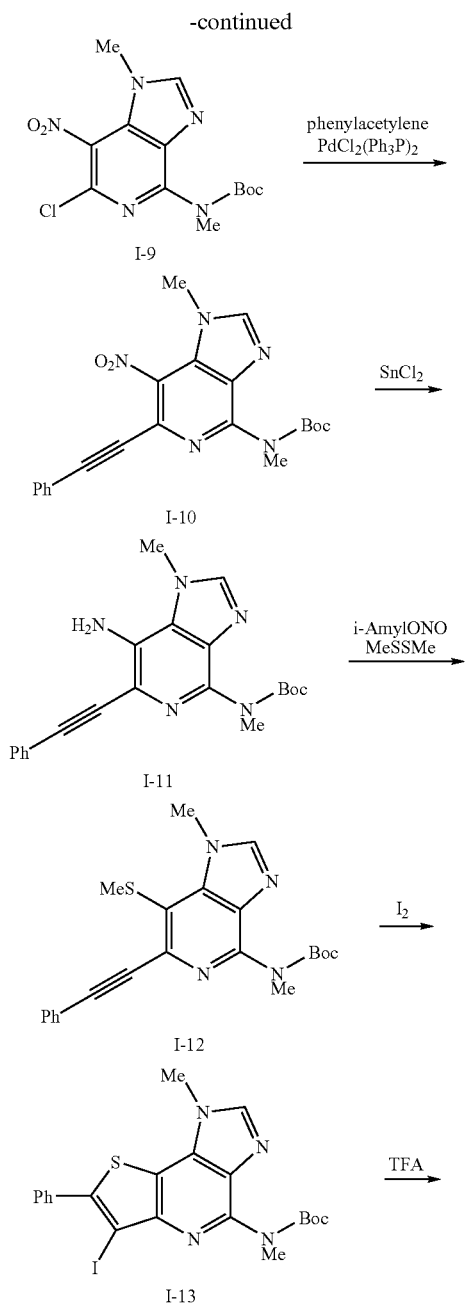

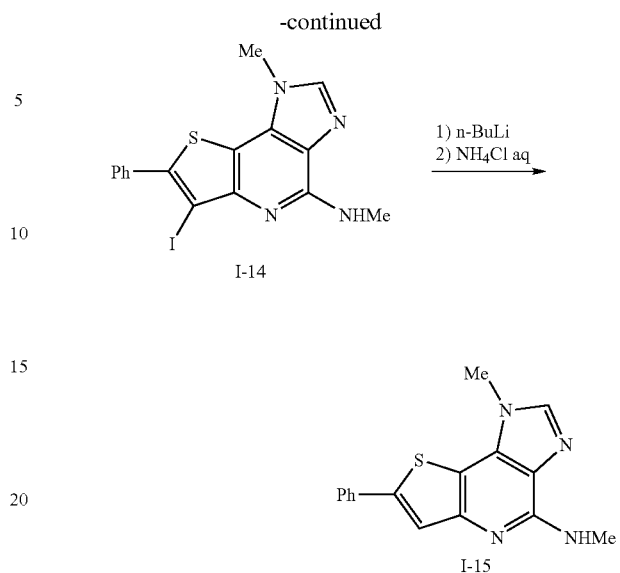

A more general synthesis of this system may be accomplished as described in Scheme II. In this instance I-9 is reacted with trimethylsilylacetylene in the presence of a suitable palladium catalyst such as dichloropalladium bis-triphenylphosphine to provide II-1. Reduction of the nitro group, followed by diazotization of the amino group and trapping with dimethyldisulfide will produce II-3. Cyclization with iodine will produce the versatile iodo intermediate II-4, which can be functionalized to produce a number of substituents at this position. For example hydrogenation of II-4 in the presence of a suitable catalyst such as palladium on carbon will produce II-5a. Alternatively II-4 can be reacted with palladium acetate and trapped with reagents such as zinc cyanide or acid chlorides to produce II-5b and II-5c respectively. In another variation II-4 can be reacted with $FSO_2CF_2CO_2Me$ or similar reagents in the presence of copper or copper salts (such as copper iodide) to provide II-5d. Treatment of II-5a-II-5d with tetra-n-butyl ammonium fluoride, cesium fluoride or similar reagents will produce II-6. Bromination of II-6 will proceed to produce II-7. Reaction of II-7 with a variety of boronic acids or heteraryl tin reagents will provide II-8 which are compounds of Formula I.

Scheme II

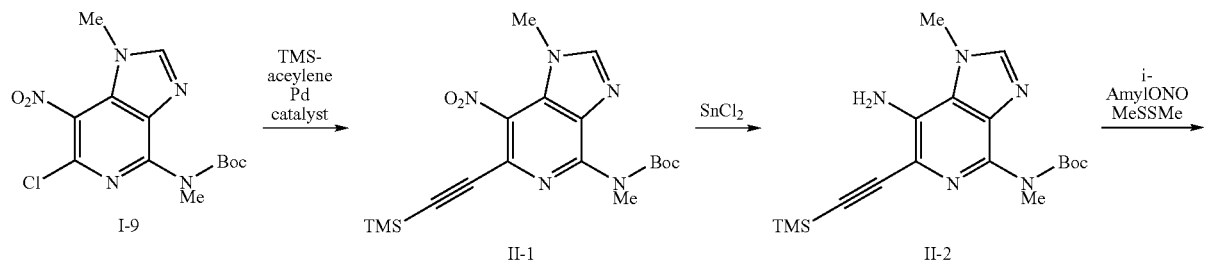

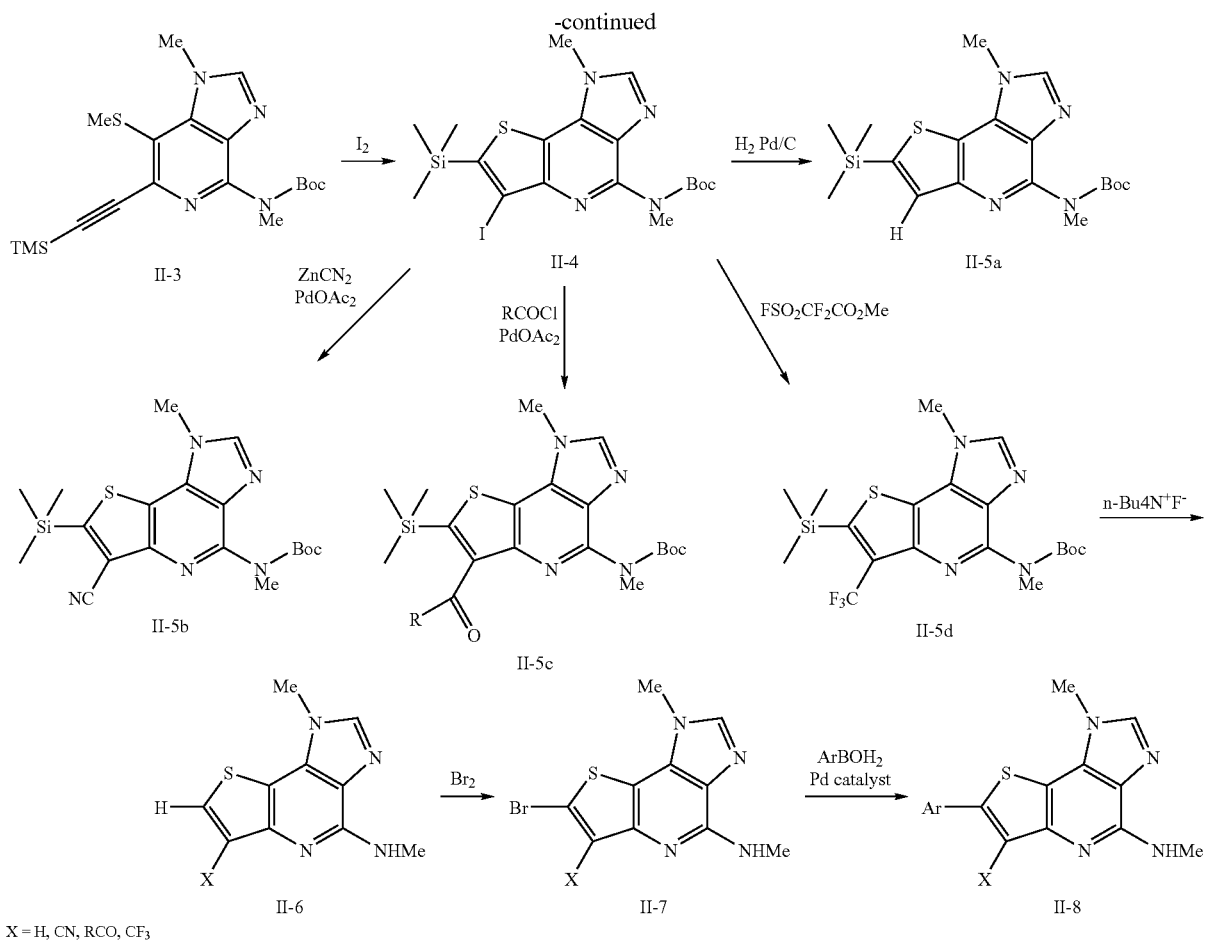

Additionally compounds of Formula I can be produced as described in Scheme III. Commercially available 7-hydroxythieno[3,2-b]pyridine (III-1) can be nitrated with fuming nitric acid to provide III-2. Pyridones such as III-2 can be reacted with phosphorus oxychloride alone or with a suitable base, for example N,N-dimethylaniline to provide III-3. Displacement of the chloride with a primary amine such as methylamine will provide III-4. Reduction of the nitro group can be accomplished by a variety of methods including catalytic hydrogenation over palladium on carbon, or platinum oxide. Alternatively nitro groups can be reduced with iron in acetic acid or formic acid, or other metals such as tin chloride to produce III-5. Cyclization of the diamine to an imidazole ring can be accomplished either by reaction with formic acid and a suitable acid catalyst such as p-toluenesulfonic acid, camphorsulfonic acid, and the like, using a Dean-Stark apparatus, or alternatively by reaction with an orthoformate such as triethylorthoformate with or without an acid catalyst to produce III-6. Oxidation of the pyridine nitrogen can be effected by a variety of reagents such as meta chloroperbenzoic acid, or hydrogen peroxide in the presence of trifluoroacetic acid to produce III-7. Pyridine N-oxides on treatment with phosphorus oxychloride can rearrange to produce III-8. Bromination of the aryl ring can be accomplished with reagents such as N-bromosuccinimide, or bromine in acetic acid to produce III-9. (Alternatively iodination can be effected in the same position by reaction with iodine in the presence of a suitable catalyst such as silver triflate).

Regiochemical aryl coupling reactions can be effected at the 7-position as a result of the greater reactivity of aryl bromides and aryl iodides to such reactions compared to aryl chlorides as is well precidented in the chemical literature. Thus reaction with an aryl or heteroaryl boronic acid, or aryl or heteoaryl tin reagent in the presence of a suitable catalyst such as palladium acetate, tetrakistriphenylphosphine palladium chloride, and the like will produce III-10, which is a compound of Formula I. Finally reaction with an amine at elevated temperature will effect displacement of the chlorine atom to provide III-11, which is also a compound of Formula I.

Alternatively, III-6 can be brominated to provide III-12. This intermediate can be reacted with aryl or heteroaryl boronic acids as described above to provide III-13, which is also a compound of Formula I.

Scheme III

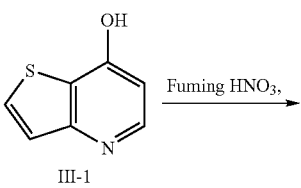

-continued
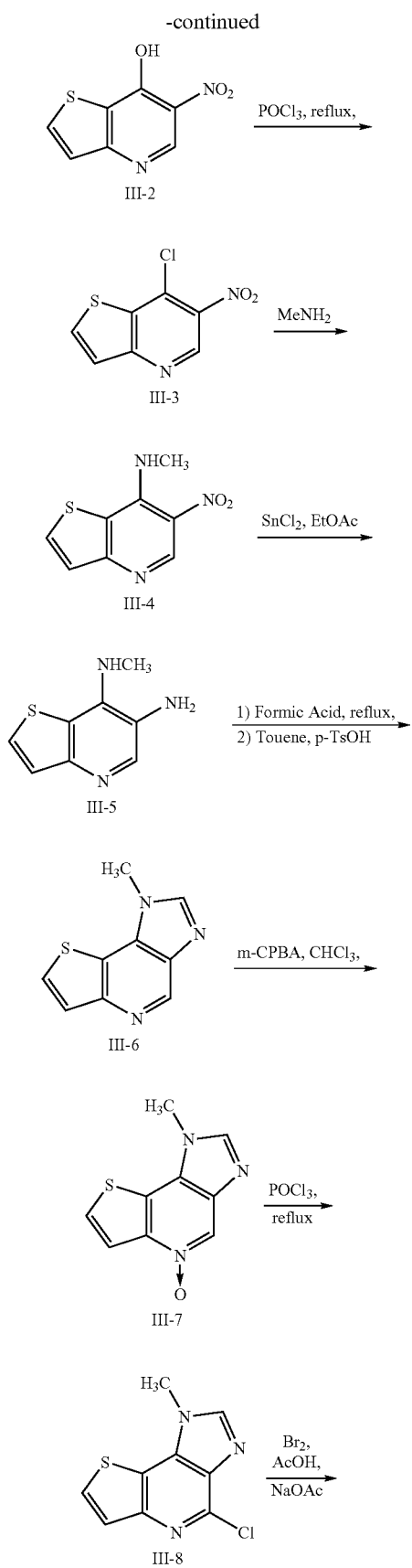
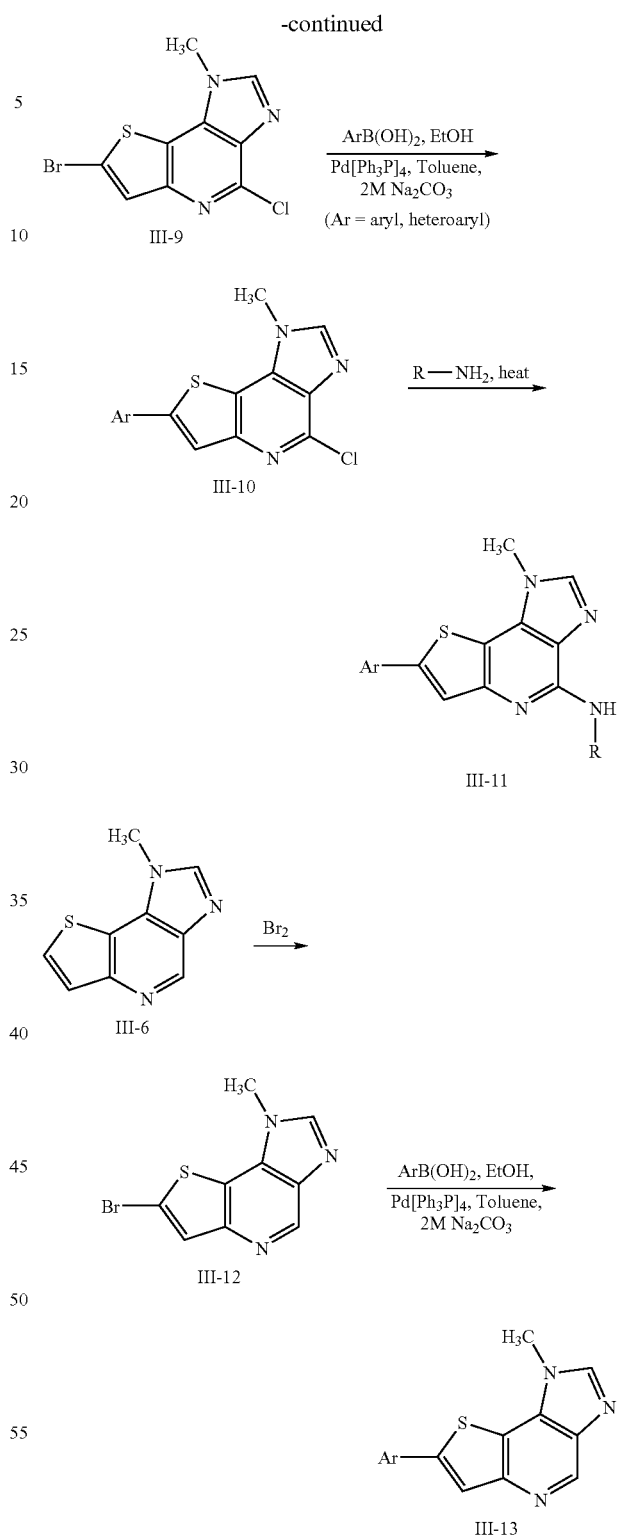
EXAMPLES
The following examples illustrate preferred embodiments of the present invention and do not limit the scope of the present invention which is defined in the claims. Abbreviations employed in the Examples are defined below. Compounds of the Examples are identified by the example and step in which they are prepared (e.g., "A1.1" denotes the title compound of step 1 of Example A1), or by the example only where the compound is the title compound of the example (for example, "A2" denotes the title compound of Example A2).

| Abbreviations | |
|---|---|
| Ac | Acetyl |
| AcOH | Acetic acid |
| aq. | Aqueous |
| CDI | Carbonyldiimidazole |
| Bn | Benzyl |
| Bu | Butyl |
| Boc | tert-butoxycarbonyl |
| DMAP | Dimethylaminopyridine |
| DMA | N,N-Dimethylacetamide |
| DMF | dimethylformamide |
| DMSO | Dimethylsulfoxide |
| EDC | 1-(3-Dimethylaminopropyl)-3-ethylcarbodiimide hydrochloride |
| EtOAc | Ethyl acetate |
| Et | Ethyl |
| EtOH | Ethanol |
| H | Hydrogen |
| h | Hours |
| i | iso |
| HPLC | High pressure liquid chromatography |
| HOAc | Acetic acid |
| Lawesson's Reagent | [2,4-bis(4-methoxyphenyl)-1,3-dithia-2,4-diphosphetane-2-4-disufide |
| LC | liquid chromatography |
| Me | Methyl |
| MeOH | Methanol |
| min. | Minutes |
| $M^+$ | $(M + H)^+$ |
| $M^{+1}$ | $(M + H)^+$ |
| MS | Mass spectrometry |
| n | normal |
| Pd/C | Palladium on carbon |
| Ph | Phenyl |
| Pr | Propyl |
| PSI | Pounds per square inch |
| Ret Time | Retention time |
| rt or RT | Room temperature |
| sat. | Saturated |
| S-Tol-BINAP | (S)-(−)-2,2'-Bis(di-p-tolylphosphino)-1,1'-binapthyl |
| t | tert |
| TFA | Trifluoroacetic acid |
| THF | Tetrahydrofuran |
| Phenominex | Phenominex, , Macclesfield, Cheshire, UK |
| YMC | YMC, Inc, Wilmington, NC 20403 |

HPLC conditions used to determine retention times; A: 2 min gradient 0-100% B in A (A; 0.1% TFA in 90/10 water/methanol; B; 0.1% TFA in 10/90 water/methanol) using a Phenominex 4.6×30 mm S-5 ODS column at with a detection wavelength of 254 nanometers or B: 4 min gradient 0-100% B in A (A; 0.1% TFA in 90/10 water/methanol; B; 0.1% TFA in 10/90 water/methanol) using a YMC Turbopack column at with a detection wavelength of 254 nanometers or 220 nanometers.

Those experiments which specify they were performed in a microwave were conducted in a SmithSynthesizer™ manufactured by Personal Chemistry. This microwave oven generates a temperature which can be selected between 60-250° C. The microwave automatically monitors the pressure which is between 0-290 PSI. Reaction times and temperatures are reported.

Example A1

N,1-Dimethyl-iodo-7-phenyl-1H-imidazo[4,5-d]thieno[3,2-b]pyridin-4-amine

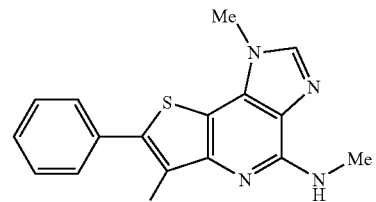

A1

A1.1: 3,5-Dinitro-1H-pyridin-4-one

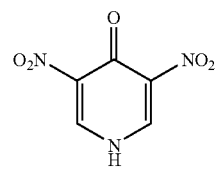

A1.1

4-Hydroxypyridine (40.0 g, 0.42 mol) was added portionwise to fuming nitric acid (140 ml) and sulfuric acid (500 ml). The resulting mixture was heated to 140° C. for 12 hours. The reaction mixture was cooled in an ice-bath and cautiously poured onto ice (500 ml). The yellow solid which precipitated was collected by filtration and dried under vacuum to yield A1.1 (70.0 g, 90%). $^1$H-NMR (DMSO-$d_6$) δ: 4.06 (2H, s). HPLC: 98.9%, ret. time=0.173 min., LC/MS (M−H)$^+$=184.

A1.2: (3,5-Dinitro-pyridin-4-yl)-methyl-amine

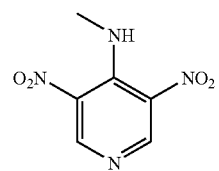

A1.2

A1.1 (10.0 g, 0.051 mol) was added portionwise to a mixture of phosphorus oxychloride (25 ml) and PCl$_5$ (17.0 g, 0.082 mol). The reaction mixture was heated to reflux under a nitrogen atmosphere for 12 hours. The reaction mixture was allowed to cool to room temperature and the phosphorus oxychloride removed in vacuo. The residue was suspended in dry THF (50 ml) and cooled to 0° C. Methylamine (32 ml, 2.0M in THF, 0.064 mol) was added dropwise over 20 minutes under a nitrogen atmosphere and the resulting solution was allowed to warm to room temperature over 1 hour. The reaction mixture was evaporated in vacuo and the residue suspended in ethyl acetate (200 ml) which was then filtered and the filtrate evaporated in vacuo to leave the crude product. The crude product was recrystallised from methanol (100 ml) to give A1.2 as a tan solid (7.2 g, 71% for two steps). HPLC: 98%, ret. time=1.58 min., LC/MS (M+H)$^+$=199.

A1.3: 2,6-Dichloro-N'-methyl-pyridine-3,4,5-triamine

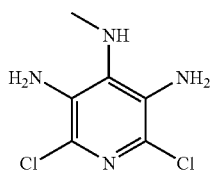

A1.3

A solution of A1.2 (60.0 g, 0.30 mol) in concentrated hydrochloric acid (300 ml) was heated to 90° C. Tin (II) chloride (85.0 g, 0.45 mol) was added portionwise over 1 hour with vigorous effervesence noted for the first equivalent of tin chloride added. The reaction mixture was heated for a further hour before the additon of more tin chloride (28.0 g, 0.15 mol) and continued heating for 2 more hours. The reaction mixture was cooled to 0° C. and cautiously basified with concentrated ammonium hydroxide (200 ml). The precipitated solid was filtered off and the filtrate extracted with ethyl acetate (5×200 ml). The combined organics were dried (MgSO4) and evaporated in vacuo to leave A1.3 as a brown solid (28.0 g, 46%). HPLC: 98%, ret. time=1.58 min., LC/MS (M+H)$^+$=208.

A1.4: 4,6-Dichloro-1-methyl-1H-imidazo[4,5-c]pyridin-7-ylamine

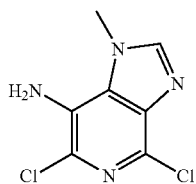

A1.4

Triethylorthoformate (25.0 ml, 0.15 mol) was added in one portion to a suspension of A1.3 (28 g, 0.14 mol) in dry acetonitrile (400 ml). The reaction mixture was heated to reflux for 4 hours and then cooled to room temperature. The reaction mixture was evaporated in vacuo to leave A1.4 as a brown powder. $^1$H-NMR (DMSO-d$_6$) δ: 8.20 (1H, s), 5.49 (−2H, br. s), 4.07 (3H, s). HPLC: 98%, ret. time=0.78 min., LC/MS (M+H)$^+$=218.

A1.5: 4,6-Dichloro-1-methyl-7-nitro-1H-imidazo[4,5-c]pyridine

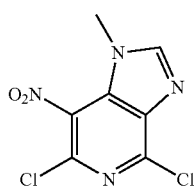

A1.5

A1.4 (5.0 g, 9.3 mmol) in concentrated sulfuric acid (40 ml) was added portionwise to a cooled mixture of hydrogen peroxide (50% aq. Solution, 40 ml) and concentrated sulfuric acid (30 ml). After stirring at 0° C. for 3 hrs, ice was added to the reaction mixture before cautiously basifying to pH7 with ammonium hydroxide solution (90 ml). The resulting precipitate was filtered to give A1.5 (3.08 g, 77%) as a yellow powder. HPLC: 98%, ret. time=1.33 min., LC/MS (M+H)$^+$=247.

A1.6: (6-Chloro-1-methyl-7-nitro-1H-imidazo[4,5-c]pyridin-4-yl)-methyl-amine

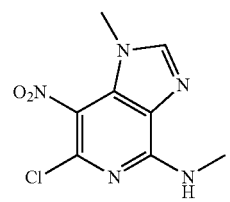

A1.6

Methylamine hydrochloride (1.62 g, 24.1 mmol) was added in one portion to a stirred solution of A1.5 (6.59 g, 26.8 mmol) and N,N-diisopropylethylamine (12.41 ml, 67.0 mmol) in NMP (40 ml) at room temperature under a nitrogen atmosphere. The reaction mixture was heated to 45° C. for 3 hrs before cooling to room temperature, and quenching by the addition of water (150 ml). The precipitated solid was filtered with suction to give A1.6 (5.62 g, 87%) as an orange solid. HPLC: 98%, ret. time=1.36 min., LC/MS (M+H)$^+$=242.

A1.7: (6-Chloro-1-methyl-7-nitro-1H-imidazo[4,5-c]pyridin-4-yl)-methyl-carbamic acid tert-butyl ester

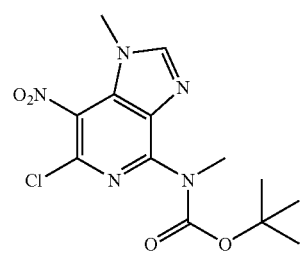

A1.7

Boc-anhydride (5.62 g, 25.7 mmol) and DMAP (0.72 g, 5.8 mmol) were each added in one portion to a solution of A1.6 (5.62 g, 23.3 mmol) in CH$_3$CN (200 ml) at room temperature under a nitrogen atmosphere. The reaction mixture was heated to reflux for 1 hr, before cooling to room temperature and evaporating in vacuo. The residue was purified by column chromatography using ethyl acetate as eluent to give A1.7 (2.74 g, 34%) as a yellow solid. HPLC: 98%, ret. time=1.71 min., LC/MS (M+H−Boc)$^+$=242.

A1.8: Methyl-(1-methyl-7-nitro-6-phenylethynyl-1H-imidazo[4,5-c]pyridin-4-yl)-carbamic acid tert-butyl ester

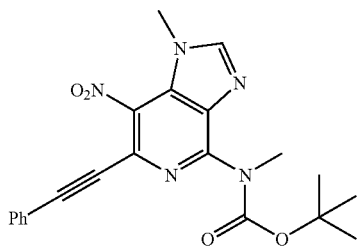

CuI (19 mg, 0.096 mmol) and dichlorobis(triphenylphosphine)palladium (169 mg, 0.24 mmol) were each added in one portion to a mixture of A1.7 (1.64 g, 4.81 mmol) and phenylacetylene (0.59 g, 5.77 mmol) in triethylamine (15 ml) at room temperature under a nitrogen atmosphere. The reaction mixture was heated to 60° C. for 4 hrs before cooling to room temperature and evaporating in vacuo. The residue was suspended in triethylamine (5 ml) and the salt filtered with suction. The filtrate was evaporated in vacuo and purified by column chromatography using ethyl acetate as eluent to give A1.8 (1.58 g, 81%) as a yellow solid. $^1$H-NMR (MeOH-$d_4$) δ: 8.4 (1H, s), 7.63-7.60 (2H, m), 7.49-7.46 (3H, m), 4.91 (3H, s), 3.90 (3H, s), 1.44 (9H, s). HPLC: 98%, ret. time=1.93 min., LC/MS (M+H)$^+$=408.

A1.9: (7-Amino-1-methyl-6-phenylethynyl-1H-imidazo[4,5-c]pyridin-4-yl)-methyl-carbamic acid tert-butyl ester

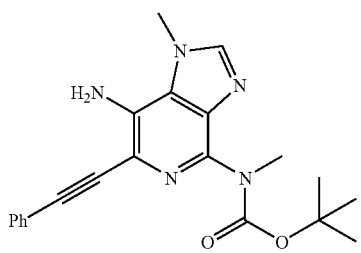

Tin (II) chloride hydrate (900 mg, 3.97 mmol) was added in one portion to a solution of A1.8 (320 mg, 0.79 mmol) in ethyl acetate (10 ml). The reaction mixture was heated at 40° C. for 1 hour before cooling to 0° C. and basifying with 2M sodium hydroxide (40 ml). The aqueous layer was extracted with ethyl acetate (2×80 ml), the combined organic layers were dried (MgSO$_4$) and evaporated in vacuo to leave the crude product A1.9 which was used immediately in the next reaction. HPLC: 98%, ret. time=1.55 min., LC/MS (M+H)$^+$=378.

A1.10 (7-Methylthio-1-methyl-6-phenylethynyl-1H-imidazo[4,5-c]pyridin-4-yl)-methyl-carbamic acid tert-butyl ester

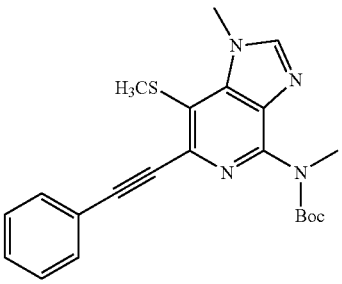

i-Amylnitrite (0.6 ml; 4 mmol) was added to a solution of A1.9 (300 mg; 0.8 mmol) in dimethyldisulfide (1.2 ml) at 80° C. Gas evolution was observed and after 20 minutes at 80° C., the volatiles were removed in vacuo. The residue was chromatographed on a 2.5×20 cm silica gel column, eluted with a gradient of ethyl acetate:hexane, 1:1 to ethyl acetate:hexane, 2:1. Concentration of the pure fractions afforded 95 mg (29%) of A1.10 as a tan amorphous solid. $^1$H-NMR (CDCl$_3$) δ: 7.87 (1H, s), 7.64 (2H, m), 7.39 (3H, m), 4.24 (3H, s), 3.46 (3H, s), 2.59 (3H, s) 1.42 (9H, s). HPLC (A): 98%, ret. time=1.85 min., LC/MS (M−H)$^+$=409.18 (309.20− minus Boc group).

A1.11 N,1-Dimethyl-N-tert-butyloxycarbonyl-6-iodo-7-phenyl-1H-imidazo[4,5-d]thieno[3,2-b]pyridin-4-amine

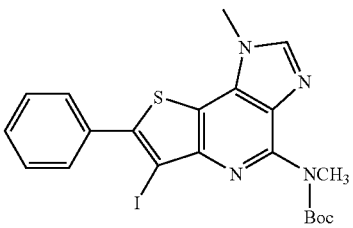

A solution of iodine (115 mg; 0.45 mmol) in dichloromethane (5 ml) was added over 5 minutes to a solution of A1.10 (92 mg; 0.22 mmol) in dichloromethane (5 ml) at rt. After stirring 30 minutes, the reaction mixture was partitioned between ethyl acetate (50 ml) and 5% sodium bisulfite solution (50 ml). The organic layer was dried (MgSO4) and concentrated to afford 114 mg (99%) of A1.11 as an amber oil. $^1$H-NMR (CDCl$_3$) δ: 7.95 (1H, s), 7.76 (2H, m), 7.51 (3H, m), 4.10 (3H, s), 3.59 (3H, s), 1.44 (9H, (A): 96%, ret. time=1.99 min., LC/MS (M+H)$^+$=520.98 (421.02− minus Boc group).

Step A1.12: N,1-Dimethyl-iodo-7-phenyl-1H-imidazo[4,5-d]thieno[3,2-b]pyridin-4-amine

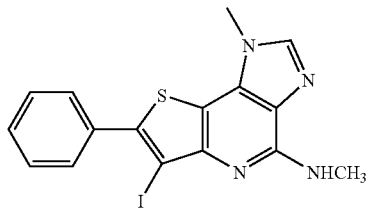

A1

A solution of A1.11 (20 mg; 0.038 mmol) in trifluroacetic acid (0.5 ml) was allowed to stand for 1 hr at rt. The volatiles were removed in vacuo and the residue was co-evaporated from ethyl acetate/heptane and ethanol/heptane. The light yellow powder was re-crystallized from ethanol to afford 9 mg (56%) of A1 as an amber crystalline solid. $^1$H-NMR (CDCl$_3$) δ: 7.79 (1H, s), 7.73 (2H, m), 7.47 (3H, m), 4.04 (3H, (3H, brs). HPLC (A): 99%, ret. time=1.48 min., LC/MS (M+H)$^+$=421.00.

Example A2

N,1-Dimethyl-7-phenyl-1H-imidazo[4,5-d]thieno[3,2-b]pyridin-4-amine

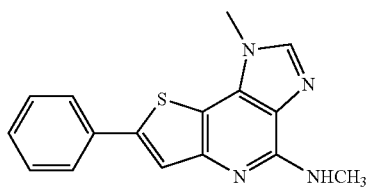

A2

A 2.5M solution of n-butyllithium (0.12 ml; 03 mmol) was added over 1 minute to a solution of A1 (29 mg; 0.054 mmol) in THF (2 ml) at −78° C. After stirring 10 minutes at −78° C., saturated ammonium chloride solution (4 ml) was added and the mixture was allowed to warm to rt. The reaction mixture was partitioned between ethyl acetate (20 ml) and water (20 ml). Drying (MgSO4) and concentration of the organic layer afforded a residue that was loaded on to a preparative silica thin layer chromatography plate. Elution with ethyl acetate and extraction of the desired band of silica afforded 7 mg (44%) of A2 as a light yellow solid. $^1$H-NMR (CDCl$_3$) δ: 7.74 (1H, s), 7.73 (2H, m), 7.71 (1H, s), 7.43 (2H, t, J=7.5 Hz) 7.33 (1H, m), 5.55 (1H, brs), 4.06 (3H s), 3.24 (3H, brs). HPLC (A): 99%, ret. time=1.35 min., LC/MS (M+H)$^+$=295.16.

Alternate Synthetic Route to N,1-Dimethyl-7-phenyl-1H-imidazo[4,5-d]thieno[3,2-b]pyridin-4-amine

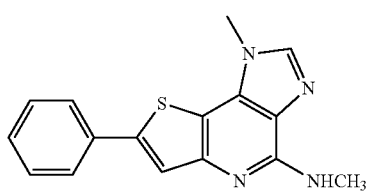

A2

A2.1: 6-Nitro-7-hydroxythieno[3,2-b]pyridine

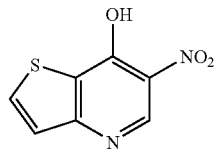

A2.1

Commercially available 7-hydroxythieno[3,2-b]pyridine (9.9 g, 65.5 mmol) was dissolved in propionic acid (200 mL) and heated to 110° C., behind a bomb shield. 4.85 mL of fuming nitric acid (90%) was added over 2 minutes, during which time a copius precipitate formed. The thick suspension was brought to reflux (oil bath temperature ~150° C.) for 1 h during which time an orange gas evolved (Caution: procedure should only be performed in a well ventilated hood). The reaction mixture was allowed to cool to room temperature and 200 mL of diethyl ether was added. The product was collected by filtration, washed with ~400 mL of water, 300 mL of 1:1 diethyl ether/methanol, and dried to yield 9.5 g, (74%) of A2.1 as a tan powder. M.S. 197 (M+H)$^+$ 100%.

A2.2: 6-Nitro-7-chlorothieno[3,2-b]pyridine

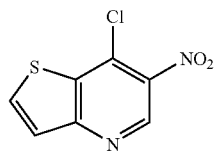

A2.2

A2.1 (9.5 g, 48.5 mmol) was suspended in phosphorus oxychloride (100 ml) and refluxed for 1 h (dissolution was apparent after ~45 min). The solvent was removed under reduced pressure. Toluene (50 mL) was added to the residue and the volitiles were removed under reduced pressure. This procedure was repeated a second time to provide a dark colored semi-solid. Dichloromethane (400 mL) and saturated aqueous socium bicarbonate (400 mL) was added (Caution: gas evolution), and the layeres separated. The aqueous layer was washed with additional dichloromethane (100 mL). The combined organic layer was washed with water (200 mL) and dried over anhydrous sodium sulfate, decolorized by the addition of activated charcoal, and filtered through celite. The organic layer was concentrated to afford 9.7 g (93%) of A2.2. M.S. 214 (M+H)$^+$ 100%, 216, (M+H)$^+$ 35%.

A2.2B: N-Methyl-6-nitrothieno[3,2-b]pyridin-7-amine

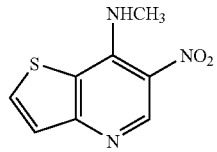

A2.3

A mixture of A2.2 (9.65 g; 44.3 mmol), methylamine hydrochloride (4.6 g; 68 mmol) and diisopropylethylamine (24.5 ml; 133 mmol) in 150 ml of N-methylpyrrolidinone was stirred for 18 hr at rt. After adding 600 ml of water, the resulting thick yellow suspension was stirred for 1.5 hr. Filtration, rinsing the filter cake with water and drying afforded 9.23 g (99%) of A2.3 as a canary yellow solid. $^1$H-NMR (CDCl$_3$) δ: 9.27 (2H, s), 7.89 (1H, d, J=5.5 Hz), 7.51 (1H, d, J=5.5 Hz), 3.61 (3H, J=5.5 Hz). HPLC (A): 99%, ret. time 0.61 min., LC/MS (M+H)$^+$=210.07.

A2.4: N$^7$-Methylthieno[3,2-b]pyridine-6,7-diamine

A2.4

A mixture of A2.3 (2.1 g; 10 mmol) and tin(II)chloride dehydrate (10.1 g; 45 mmol) in 100 ml of ethyl acetate was heated to reflux for 1 hr. After cooling, the reaction mixture was partitioned between of ethyl acetate (300 ml) and 2N NaOH (300 ml). The organic layer was washed with 2N NaOH (200 ml) and brine (100 ml). The combined aqueous layers were back extracted with chloroform (100 ml). The chloroform layer was washed with 2N NaOH (100 ml) and brine (100 ml). The combined organic layers were dried (Na$_2$SO$_4$) and concentrated to afford 1.33 g (74%) of A2.4 as a yellow solid. $^1$H-NMR (DMSO-d$^6$) δ: 8.39 (1H, s), 7.94 (1H, d, J=5.5 Hz), 7.61 (1H, d, J=5.5 Hz), 5.52 (1H, m), 4.63 (2H, m), 3.29 (3H, d, J=5 Hz). HPLC (A): 97%, ret. time 0.59 min., LC/MS (M+H)$^+$=180.06.

A2.5: 1-Methyl-1H-imidazo[4,5-d]thieno[3,2-b]pyridine

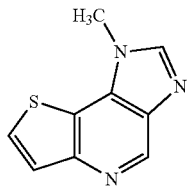

A2.5

A mixture of A2.4 (1.3 g; 7.25 mmol) and formic acid (20 ml) was gently refluxed for 1 hr. After removing the volatiles in vacuo, the residue was dissolved in toluene (50 ml) and ~10 mg of p-toluenesulphonic acid monohydrate was added. After refluxing this mixture for 1 hr with a Dean-Starke water separator, the reaction mixture was cooled and diluted with 100 ml of ethyl acetate. Saturated sodium bicarbonate solution (50 ml) was added and the biphasic mixture was stirred briskly for 10 minutes. After separating the layers, the aqueous layer was extracted with chloroform (3×50 ml). After allowing the combined organic layers to stand over Na$_2$SO$_4$ for 18 hrs, the volatiles were removed in vacuo to afford 1.24 g (91%) of A2.5 as a light yellow solid.

$^1$H-NMR (DMSO-d$^6$) δ: 9.07 (1H, s), 8.47 (1H, s), 8.13 (1H, d, J=5.5 Hz), 7.77 (1H, d J=5.5 Hz), 4.17 (3H, s). HPLC (A): 99%, ret. time 0.44 min., LC/MS (M+H)$^+$=190.09.

A2.6: 1-Methyl-1H-imidazo[4,5-d]thieno[3,2-b]pyridine-5-oxide

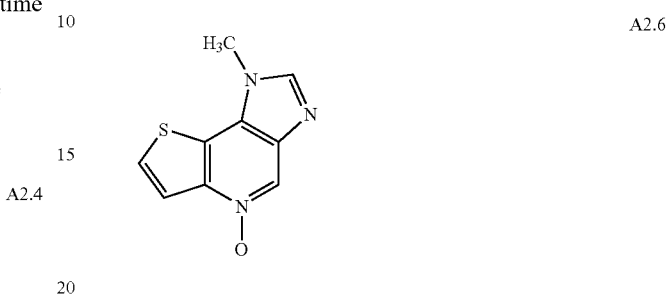

A2.6 m-Chloroperbenzoic acid, 77% (1.53 g; 6.8 mmol) was added to a solution of A2.5 (1.23 g; 6.5 mmol) in 60 ml of chloroform at rt. After stirring 1 hr at rt, additional m-chloroperbenzoic acid, 77% (75 mg; 0.3 mmol) was added and the reaction mixture was stirred 2 hrs. Following one more addition of m-chloroperbenzoic acid, 77% (40 mg; 0.18 mmol) and one hr of stirring, the reaction mixture was concentrated to a salmon colored solid. Trituration with ethyl ether and filtration afforded 1.5 g (>100%; contaminated with 3-chlorobenzoic acid) of A2.6 as a salmon colored solid.

$^1$H-NMR (CDCl$_3$) δ: 8.94 (1H, s), 8.09 (1H, d, J=5.5 Hz), 7.99 (1H, s), 7.68 (1H, d, J=5.5 Hz), 4.13 (3H, s). HPLC (A): 99%, ret. time 0.51 min., LC/MS (M+H)$^+$=206.06.

A2.7: 4-Chloro-1-Methyl-1H-imidazo[4,5-d]thieno[3,2-b]pyridine

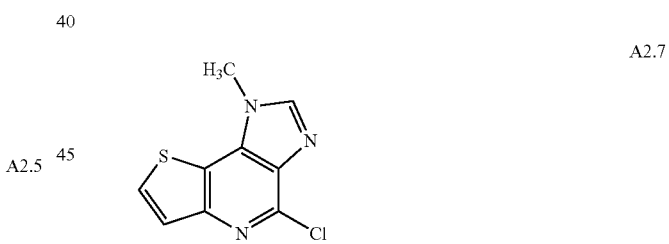

A2.7

A suspension of A2.6 (1.5 g; 6.5 mmol) in phosphorous oxychloride (20 ml) was heated to reflux for 1 hr. After cooling to rt, the volatiles were removed in vacuo and the residue was co-evaporated from toluene. The residue was suspended in ethyl acetate:THF, 1:1 (100 ml) and saturated sodium bicarbonate solution (40 ml) was added. After stirring briskly for 5 minutes, the layers were separated and the aqueous layer was extracted with ethyl acetate:THF, 1:1 (40 ml). The combined organic layers were washed with brine (25 ml) and dried over Na$_2$SO$_4$. The organic layer was filtered through a 1×5 cm plug of silica gel and the plug was rinsed thoroughly with ethyl acetate and THF. The filtrate was concentrated and the residue was triturated with ethyl ether to afford 1.14 g (79%; over 2 steps) of A2.7 as a pale yellow solid. $^1$H-NMR (CDCl$_3$) δ: 7.98 (1H, s), 7.70 (1H, d, J=5.5 Hz), 7.66 (1H, d, J=5.5 Hz), 4.14 (3H, s). HPLC (A): 98%, ret. time 1.06 min., LC/MS (M+H)$^+$=224.09 (226.04).

A2.8: 7-Bromo-4-chloro-1-methyl-1H-imidazo[4,5-d]thieno[3,2-b]pyridine

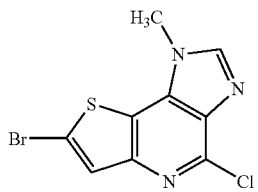

A2.8

Bromine (0.05 ml; 1 mmol) was added to a solution of A2.7 (134 mg; 0.6 mmol) and sodium acetate (246 mg; 3 mmol) in 2 ml of acetic acid at rt. After stirring 8 hr at rt, additional bromine (0.015 ml; 0.3 mmol) was added. After stirring 18 hr at rt, additional bromine (0.010 ml; 0.2 mmol) was added and stirring was continued for 24 hr. One more addition of bromine (0.005 ml; 0.1 mmol) was made and after 5 hr, a solution of sodium bisulfite (156 mg) in 1 ml of water was added. The mixture was concentrated to ~1 ml and 20 ml of water was added. The resulting suspension was sonicated for 5 minutes and filtered. The filter cake was washed with water and dried to afford 155 mg (86%) of A2.8 as a tan powder. $^1$H-NMR (CDCl$_3$) δ: 7.98 (1H, s), 7.65 (1H, s), 4.08 (3H, s). HPLC (A): 71% (Product contains ~14% of a di-brominated contaminant by 1H NMR), ret. time 1.56 min., LC/MS (M+H)$^+$=304.01 (302.03, 306.00).

A2.9: 4-Chloro-1-methyl-7-phenyl-1H-imidazo[4,5-d]thieno[3,2-b]pyridine

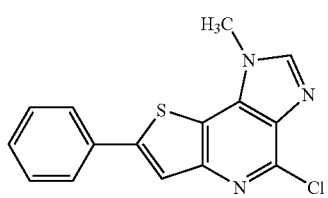

A2.9

A mixture of A2.8 (45 mg; 0.14 mmol), phenylboronic acid (30 mg; 0.23 mmol), tetrakis(triphenylphosphine)palladium (0) (5 mg; 0.004 m-mol), 2M Na$_2$CO$_3$ (0.25 ml), ethanol (0.3 ml) and toluene (0.5 ml) was vigorously stirred at 90° C. for 1.5 hr. After cooling to rt, the reaction mixture was diluted with ethyl acetate (15 ml), dried (MgSO$_4$) and concentrated. The residue, combined with a residue from a reaction of the same scale, was chromatographed on a 2.5×15 cm silica gel column using a stepwise gradient from 100% chloroform to 5% methanol in chloroform. The purest fractions were concentrated and triturated with ethyl ether to afford 40 mg (48%) of A2.9 as a tan powder. $^1$H-NMR (CDCl$_3$) δ: 7.95 (1H, s), 7.81 (1H, s), 7.71 (2H, d=7 Hz), 7.47 (2H, m), 7.41 (1H, m), 4.13 (3H, s). HPLC (A): 89% ret. time 1.84 min., LC/MS (M+H)$^+$=300.12 (302.13).

A2 (from A2.9): N,1-Dimethyl-7-phenyl-1H-imidazo[4,5-d]thieno[3,2-b]pyridin-4-amine A mixture of A2.9 (5 mg; 0.017 mmol) and 8M methylamine in ethanol (0.5 ml; 4 mmol) was heated in a microwave reactor to 140° C. for 0.5 hr, 150° C. for 1 hr and 160° C. for 1 hr. After cooling to rt, 1 ml of water was added and the reaction mixture was placed under a slow stream of nitrogen for 2 hr. Water (0.5 ml) was added and the resulting suspension was filtered to afford 4 mg (85%) of A2 as a white powder. This material is identical to A2 prepared by the first method by HPLC, LC/MS and 1HNMR.

Example A3

N-Ethyl-1-methyl-7-phenyl-1H-imidazo[4,5-d]thieno[3,2-b]pyridin-4-amine trifluoroacetate salt

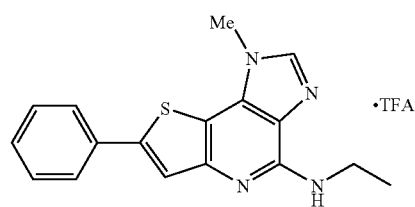

A3

A mixture of A2.9 (15 mg; 0.05 mmol), 70% aqueous ethylamine (0.75 ml) and n-butanol (0.25 ml) was heated in a microwave reactor to 170° C. 1.5 hr. The reaction mixture was concentrated and purified by preparative HPLC to afford 14 mg of A3 as a white solid. $^1$H-NMR (CF$_3$COOD) δ: 8.20 (1H, s), 6.65 (1H, s), 6.58 (2H, m), 6.37 (3H, m), 3.30 (3H, brs), 2.68 (2H, m), 0.43 (3H, m). HPLC (A): 99% ret. time 1.51 min., LC/MS (M+H)$^+$=309.24.

Example A4

1-methyl-7-phenyl-1H-imidazo[4,5-d]thieno[3,2-b]pyridin-4-amine trifluoroacetate salt

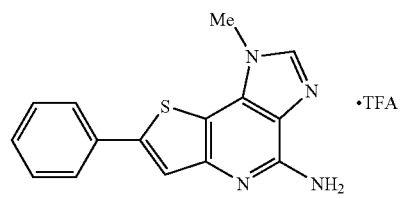

A4

A mixture of A2.9 (15 mg; 0.05 mmol) and p-methoxybenzylamine (0.2 ml) was heated to 180° C. for 2 hr. After cooling to rt, water (1 ml) was added and the mixture was stirred rapidly for 1 minute. The water was decanted off and the procedure was repeated once more to afford an oily residue. Methanol (1 ml) was added and the resulting mixture was stirred under a slow stream of nitrogen until a solid precipitant formed. Filtration and drying afforded a cream colored powder that was subsequently dissolved in trifluoroacetic acid (0.25 ml). The solution was allowed to stand at rt for 2 hr and 45° C. for 1 hr. The volatiles were removed in vacuo and the residue was co-evaporated from ethyl acetate/heptane (3×4 ml). Trituration with ethyl ether and drying afforded 11 mg of A4 as a white powder. $^1$H-NMR (CF$_3$COOD) δ: 8.27 (1H, s), 6.59 (2H, m), 6.56 (1H, s), 6.36 (3H, m), 3.30 (3H, s). HPLC (A): 97% ret. time 1.42 min., LC/MS (M+H)$^+$=281.17.

Example A5

7-(3-Fluorophenyl)-1-methyl-1H-imidazo[4,5-d]thieno[3,2-b]pyridin-4-amine hydrochloride salt

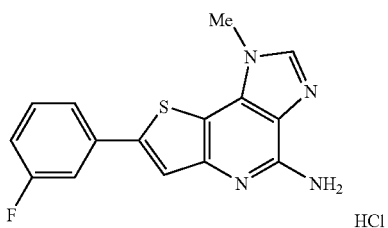

(Caution: This material was subjected to Ames testing and found to be positive in T98 with S9 activation. Suitable precautions should be taken in handling this material)

A5.1: N-[4-Methoxyphenylmethyl]-1-Methyl-1H-imidazo[4,5-d]thieno[3,2-b]pyridin-4-amine

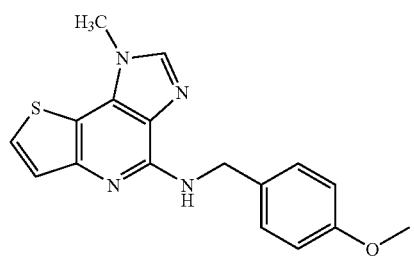

A mixture of A2.7 (447 mg; 2.0 mmol) and p-methoxybenzylamine (1.1 ml) was heated to 150-165° C. for 4 hr. After cooling to rt and standing for 3 days additional p-methoxybenzylamine (0.5 ml) was added and the reaction was heated to 165° C. for 2 hrs. After cooling to ~40° C., water (10 ml) was added and the mixture was stirred rapidly for 5 minutes. The water was decanted off and the procedure was repeated once more to afford an oily residue. Methanol (10 ml) was added and the resulting mixture was stirred for 15 minutes, during which time a tan suspension formed. Filtration and drying afforded 465 mg (72%) of A5.1 as a light tan powder. $^1$H-NMR (DMSO-d$^6$) δ: 8.13 (1H, s), 7.74 (1H, d, J=5.5 Hz), 7.32 (3H, m), 7.16 (1H, t, J=6.5 Hz), 6.84 (2H, d, J=8.5 Hz), 4.67 (2H, d, J=6.5 Hz), 4.00 (3H, s), 3.70 (3H, s). HPLC (A): 99%, ret. time 1.26 min., LC/MS (M+H)$^+$=325.27.

A5.2: N-[4-Methoxyphenylmethyl]-N-t-butyloxycarbonyl-1-methyl-1H-imidazo[4,5-d]thieno[3,2-b]pyridin-4-amine

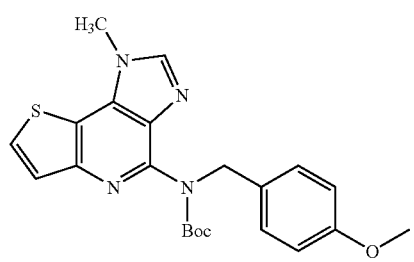

A mixture of A5.1 (460 mg; 1.4 mmol), di-t-butyldicarbonate (660 mg; 3 mmol) and 4-dimethylaminopyridine (49 mg; 0.4 mmol) in 10 ml of acetonitrile was heated to 55-60° C. for 1 hr. At this time, additional di-t-butyldicarbonate (330 mg; 1.5 mmol) was added as a solution in 1 ml of THF and heating was continued for 45 minutes. After stirring 18 hrs at rt, additional di-t-butyldicarbonate (660 mg; 3 mmol) and 4-dimethylaminopyridine (49 mg; 0.4 mmol) were added and the reaction was heated to 50° C. for 1.5 hrs. Additional di-t-butyldicarbonate (1 g; 4.4 mmol) was added and heating was continued for 30 minutes. After cooling to rt, the reaction mixture was concentrated and the residue was chromatographed on a 2.5×15 cm silica gel column, eluting with a gradient from hexane to 80% ethyl acetate in hexane. Concentration of pure fractions afforded 530 mg (89%) of A5.2 as a light yellow powder. $^1$H-NMR (DMSO-d$^6$) δ: 8.37 (1H, s), 8.03 (1H, d, J=5.5 Hz), 7.61 (1H, d, J=5.5 Hz), 7.29 (2H, d, J=8.5 Hz), 6.76 (2H, d, J=8.5 Hz), 5.07 (2H, s), 4.07 (3H, s), 3.65 (3H, s), 1.31 (9H, s). HPLC (A): 99%, ret. time 1.69 min., LC/MS (M+H)$^+$=425.24.

A5.3: 1-Methyl-1H-imidazol-[4,5-d]thieno[3,2-b]pyridin-4-amine trifluoroacetate salt

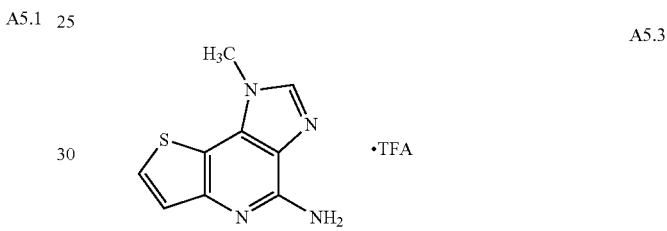

A mixture of A5.2 (420 mg; 1 mmol) and TFA (5 ml) was stirred for 3 hr at rt and 2 hr at 60° C. After allowing to cool overnight, the volatiles were removed in vacuo and the residue was co-evaporated from ethyl acetate/heptane. The residual solid was triturated with ethyl ether to afford 285 mg (90%) of A5.3 as a white solid. $^1$H-NMR (DMSO-d$^6$) δ: 8.13 (1H, s), 7.76 (1H, d, J=5 Hz), 7.28 (1H, d, J=5 Hz), 6.25 (2H, s) 4.00 (3H, s). HPLC (A): 99%, ret. time 0.74 min., LC/MS (M+H)$^+$=205.16.

A5.4: N,N-Di(t-butyloxycarbonyl)-1-Methyl-1H-imidazo[4,5-d]thieno[3,2-b]pyridin-4-amine

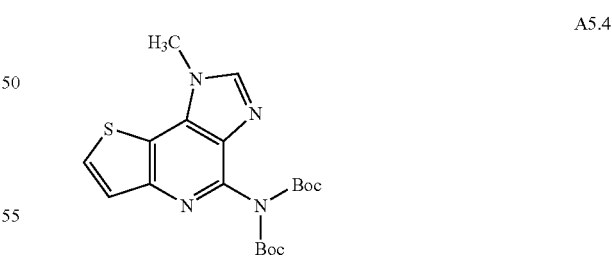

A mixture of A5.3 (283 mg; 0.9 mmol), di-t-butyldicarbonate (675 mg; 3.1 mmol), diisopropylethylamine (0.55 ml; 3 mmol) and 4-dimethylaminopyridine (28 mg; 0.25 mmol) in 6 ml of acetonitrile was heated to 60° C. After 1 hr at 60° C., additional di-t-butyldicarbonate (1 g; 4.4 mmol) was added as a solution in 2 ml of THF and heating was continued for 1 hr. After cooling to rt, the volatiles were removed in vacuo and the residue was dissolved in EtOH (10 ml). After cooling to 0° C., 1N NaOH (2 ml) was added and the reaction mixture was stirred 30 minutes at 0° C. and 1 hr at rt. The reaction mixture was concentrated and the residue was partitioned between ethyl acetate (50 ml) and water (50 ml). After washing with brine (50 ml), the organic layer was dried (MgSO$_4$), decolorized, filtered through Celite® and concentrated to afford a residue that was triturated with ethyl ether. After allowing the suspension to stand overnight, one volume of heptane was added and the resulting mixture was filtered. The filter cake was rinsed with heptane:ethyl acetate, 3:1 and dried to afford 285 mg (79%) of A5.4 as a light yellow solid. $^1$H-NMR (DMSO-d$^6$) δ: 8.40 (1H, s), 8.10 (1H, d, J=5.5 Hz), 7.67 (1H, d, J=5.5 Hz), 4.12 (3H, s), 1.35 (18H, s). HPLC (A): 96.6%, ret. time 1.55 min., LC/MS (M+H)$^+$=405.28

A5.5: 7-Bromo-N,N-di(t-butyloxycarbonyl)-1-Methyl-1H-imidazo[4,5-d]thieno[3,2-b]pyridin-4-amine

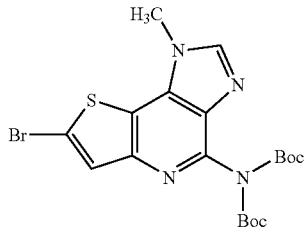

A5.5

A mixture of A5.4 (280 mg; 0.69 mmol), bromine (0.052 ml; 1 mmol) and sodium acetate (290 mg; 3.5 mmol) in 4 ml of AcOH was stirred at rt for 3 days. At this time, additional bromine (0.025 ml; 0.5 mmol) was added and stirring at rt was continued. After 2 days, additional bromine (0.01 ml; 0.2 mmol) and sodium acetate (100 mg; 1.2 mmol) were added and stirring was continued for 4 hr at rt. The volatiles were removed in vacuo and the residue was co-evaporated from heptane (4×10 ml). The residue was partitioned between ethyl acetate (50 ml) and water (20 ml). The ph of the water layer was adjusted to 9 by the careful addition of solid sodium bicarbonate to the biphasic mixture. After separating the layers, the organic layer was washed with 5% sodium bisulfite solution (40 ml) and brine (40 ml). Drying (MgSO$_4$) and concentration afforded a residue that was chromatographed on a 2.5×15 cm silica gel column, using a gradient from 50% ethyl acetate/hexane to ethyl acetate. Product containing fractions were concentrated to afford 165 mg (50%) of A5.5 as a white solid. $^1$H-NMR (DMSO-d$^6$) δ: 8.41 (1H, s), 7.91 (1H, s), 7.67 (1H, d, J=5.5 Hz), 4.08 (3H, s), 1.34 (18H, s). HPLC (A): 68%, ret. time 1.84 min., LC/MS (M+H)$^+$=483.16/485.16.

A5.6: 7-(3-Fluorophenyl)-N,N-di(t-butyloxycarbonyl)-1-Methyl-1H-imidazo[4,5-d]thieno[3,2-b]pyridin-4-amine

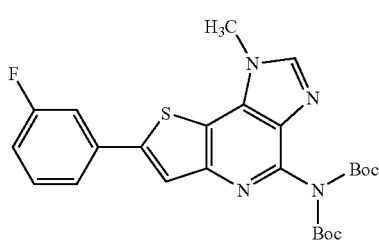

A5.6

A mixture of A5.5 (162 mg; 0.33 mmol), 3-fluorophenylboronic acid (70 mg; 0.5 mmol), tetrakis(triphenylphosphine)palladium(0) (10 mg; 0.008 mmol), 2M Na$_2$CO$_3$ (1 ml), ethanol (1.5 ml) and toluene (2.5 ml) was vigorously stirred at 95° C. for 1 hr. The reaction mixture was partitioned between ethyl acetate (50 ml) and water (20 ml). After washing with brine (20 ml), the organic layer was dried (MgSO$_4$) and concentrated. The residue that was chromatographed on a 2.5×15 cm silica gel column, using a gradient from 30% ethyl acetate/hexane to 65% ethyl acetate/hexane. The product containing fractions were concentrated to afford 150 mg (91%) of A5.6 as a white powder. $^1$H-NMR (DMSO-d$^6$) δ: 8.43 (1H, s), 8.25 (1H, s), 7.90-7.55 (3H, m), 7.28 (1H, m), 4.15 (3H, s), 1.36 (18H, s). HPLC (A): 74%, ret. time 1.98 min., LC/MS (M+H)$^+$=499.29.

A5.7: 7-(3-Fluorophenyl)-1-methyl-1H-imidazo[4,5-d]thieno[3,2-b]pyridin-4-amine hydrochloride salt A5.6 (50 mg; 0.1 mmol) was dissolved in 1 ml of TFA at rt. After standing 1 hr at rt, the volatiles were removed in vacuo and the residue was co-evaporated from ethyl acetate/heptane (3×5 ml). Triturated residue with methanol and filtered white solid. After suspending the solid in ethanol (8 ml), 1N HCl (2 ml) was added and the mixture was refluxed until complete dissolution was observed. After allowing to cool to rt, the volatiles were removed in vacuo and the residue was triturated with methanol. Filtration and drying afforded 8 mg (24%) of A5 as a white powder.

$^1$H-NMR (DMSO-d$^6$) δ: 8.53 (2H, brs), 8.47 (1H, s), 7.93 (1H, s), 7.76 (1H, td, J=2, 10 Hz), 7.67 (1H, d, J=8 Hz), 7.58 (1H, dd, J=8, 14 Hz), 7.31 (1H, dt, J=2.5, 8.5 Hz) 4.10 (3H, s). HPLC (A): 97%, ret. time 1.42 min., LC/MS (M+H)$^+$=299.22.

Example A6

6-Bromo-7-(3-fluorophenyl)-N,1-dimethyl-1H-imidazo[4,5-d]thieno[3,2-b]pyridin-4-amine

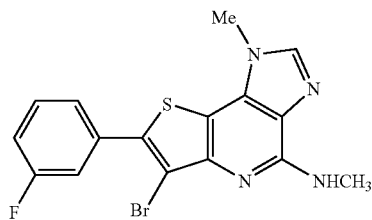

A6

A6.1: 4-Chloro-6,7-dibromo-1-methyl-1H-imidazo[4,5-d]thieno[3,2-b]pyridine

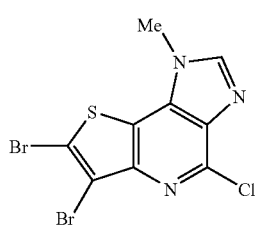

A6.1

A2.7 (560 mg, 2.5 mmol) was dissolved in a mixture of acetic acid (25 mL) and sodium acetate (4.1 g, 50 mmol). Bromine (0.65 mL, 12.5 mmol) was added dropwise and the reaction mixture stirred for 24 h at room temperature. Additional bromine (0.40 mL, 7.7 mmol) was added and the reaction mixture stirred for an additional 42 h. Sodium bisulfite 5.2 g, 50 mmol) was suspended in water (10 mL) and added to the reaction mixture. After 10 min. the solvent was removed under reduced pressure with the aid of 1:1 ethyl acetate/ heptane. The residue was suspended in 100 mL of water and the pH adjusted to pH 5-6 (pH paper) by the cautious addition of solid sodium bicarbonate. The solid was filtered, rinsed with additional water, and dried to yield A6.1 as a tan solid. LCMS; MW obs. 379 (40%), 381.91 (100%), 383.93 (80%), 385.90 (20%). RT=1.87 min.

A6.2: 4-Chloro-6-bromo-7-[3-fluorophenyl]-1-methyl-1H-imidazo[4,5-d]thieno[3,2-b]pyridine

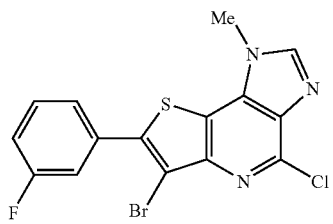

A6.2

A6.1 (135 mg, 0.35 mmol), 3-fluorobenzene boronic acid (50 mg, 0.35 mmol), and tetrakistriphenylphosphine palladium (0) (10 mg, 0.0086 mmol) were dissolved in a solvent mixture containing toluene (2.5 mL), ethanol (1.5 mL) and 2 M aqueous sodium carbonate (1 mL) and heated at 95° C. for 2 h then at 110° C. for 6 h. The reaction mixture was allowed to cool to room temperature and diluted with ethyl acetate (30 mL) and water (20 mL) and separated. The aqueous layer was extracted with chloroform (30 mL) and 10% methanol/chloroform (2×30 mL). The combined organic layers were dried over magnesium sulfate and decolorized with charcoal, filtered through celite. The solvent was removed under reduced pressure to yield a the crude product as a light yellow solid (115 mg). The solid was triturated with diethyl ether to provide A6.2 (55 mg, 40%) as a white powder. LCMS RT=3.73 min, 93%. MS: 396.03 (70%), 398.03 (100%), 400; 0.03 (30%).

A6.3: 6-Bromo-7-(3-fluorophenyl)-N,1-dimethyl-1H-imidazo[4,5-d]thieno[3,2-b]pyridin-4-amine A6.2 (55 mg, 0.14 mmol) was suspended in 8M methyl amine in ethanol (1 mL). The reaction mixture was heated to 120° C. by microwave, followed by an additional 1 h at 130° C. The reaction mixture was allowed to cool to room temperature and the crude product (~40 mg) filtered, rinsed with ethanol and recrystalized from ethanol to provide A6 (17 mg) as light yellow crystals. LC analysis detected an impurity in the product. The solid was combined with the filtrated and the solvent removed and the residue purified by flash column chromatography to provide A6 (25 mg, 46%, 98.2% pure by analytical HPLC). LCMS ret time=3.21 min. MS=391 (95%), 393.08 (100%).

Example A7

7-(3-fluorophenyl)-N,1-dimethyl-1H-imidazo[4,5-d]thieno[3,2-b]pyridin-4-amine

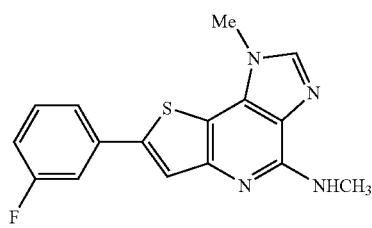

A7

A7.1: 4-Chloro-7-(3-fluorophenyl)-1-methyl-1H-imidazo[4,5-d]thieno[3,2-b]pyridine

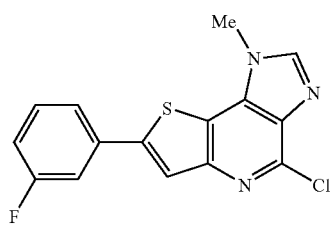

A7.1

A2.8 (400 mg, 1.3 mmol), 3-fluorobenzene boronic acid (231 mg, 1.65 mmol), and tetrakistriphenylphosphine palladium (0) (40 mg, 0.035 mmol) were dissolved in a solvent mixture containing toluene (8 mL), ethanol (5 mL) and 2 M aqueous sodium carbonate (3 mL) and heated at 95° C. for 1 h. The reaction mixture was partitioned between ethyl acetate (75 mL) and water (50 mL). The organic layer was washed with brine separated, dried over magnesium sulfate, decolorized by the addition of charcoal, filtered through celite and the filtrated was concentrated under reduced pressure. The crude product (467 mg) was triturated with ether and filtered to yield A7.1 (182 mg, 43%) as an off-white powder. A second crop of product (56 mg) was obtained by the addition of hexane to the filtrate. LCMS ret time 1.87 min (98% purity) MS: 318.16 (100%), 320.16 (30%).

A7.2: 7-(3-fluorophenyl)-N,1-dimethyl-1H-imidazo[4,5-d]thieno[3,2-b]pyridin-4-amine A7.1 (50 mf, 0.16 mmol) was suspended in 8M methylamine in ethanol (1 mL) and heated in a microwave at 120° C. for 1.5 h, and at 125° C. for 1 h. The reaction mixture was partitioned between chloroform (30 mL) and water (20 mL). The aqueous layer was extracted with additional chloroform (20 mL) and the combined organic layer was drived over magnesium sulfate, filtered and the solvent removed under reduced pressure to yield the crude product as a yellow solid.

The product was purified by flash column chromatography (chloroform→3% methanol/chloroform) to provide A7 (30 mg, 61%) as a pale yellow powder. LCMS: ret tim=1.51 min (100%), MS=313.23 (100%). NMR (DMSO-d$^6$) 400 mhz δ: 8.14 (s, 1H), 7.96 (s, 1H), 7.74-7.60 (m, 2H), 7.20 (apparent triplet, 1H), 6.95-6.85 (br s, 1H), 4.03 (s, 3H), 2.98 (d, 3H).

Example A8

7-(3,5-difluorophenyl)-N,1-dimethyl-1H-imidazo[4,5-d]thieno[3,2-b]pyridin-4-amine

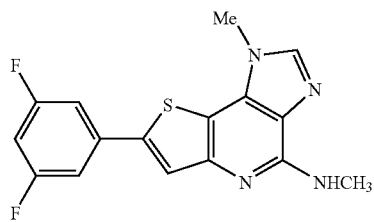

A8

A8.1: 4-Chloro-7-(3,5-difluorophenyl)-1-methyl-1H-imidazo[4,5-d]thieno[3,2-b]pyridine

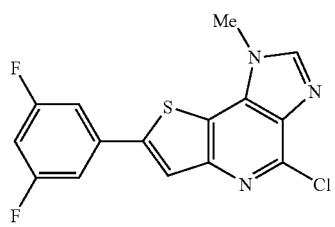

A8.1

A2.8 (62 mg, 0.2 mmol), 3,5-difluorobenzene boronic acid (43 mg, 0.26 mmol), and tetrakistriphenylphosphine palladium (0) (6 mg, 0.005 mmol) were dissolved in a solvent mixture containing toluene (0.8 mL), ethanol (0.5 mL) and 2 M aqueous sodium carbonate (0.4 mL) and heated at 100° C. for 4 h. The reaction mixture was partitioned between chloroform (30 mL) and water (10 mL). The aqueous layer was extracted with additional chloroform (25 mL). The combined organic layer was dried over sodium sulfate overnight, filtered and evaporated to provide the crude product. The solid was triturated with diethyl ether and dried to provide A8.1 (43 mg, 62%) as a light yellow powder. LCMS: ret time 2.03 min, 93% purity MS: 336.12 (100%), 338.13 (30%). $^1$H-NMR (DMSO-d$^6$) 400 mhz δ: 8.51 (s, 1H) 8.32 (s, 1H), 7.58 (d, J=7 Hz, 2H), 7.35 (t, J=7 Hz, 1H) 4.12 (s, 3H).

A8.2: 7-(3,5-difluorophenyl)-N,1-dimethyl-1H-imidazo[4,5-d]thieno[3,2-b]pyridin-4-amine A8.1 (35 mg, 0.1 mmol) was suspended in 8M methylamine in ethanol (1 mL) and heated to 130° C. in a microwave for 1 h. The reaction mixture was allowed to cool to room temperature and stand over the weekend. The reaction mixture was concentrated and purified by preparatory reverse phase HPLC to provide A8 as a solid (32 mg, 73%). LCMS: ret time=1.67 min, 96% purity; MS: 331.22 (100%). NMR (DMSO-d$^6$) 400 mhz δ: 8.54 (s, 1H) 8.00 (s, 1H), 7.54 (d, J=7 Hz, 2H), 7.38 (t, J=7 Hz, 1H) 4.12 (s, 3H), 3.12 (s, 3H).

Example A9

7-[3-(aminomethyl)phenyl]-1-methyl-1H-imidazo[4,5-d]thieno[3,2-b]pyridin-4-amine trifluoroacetate salt

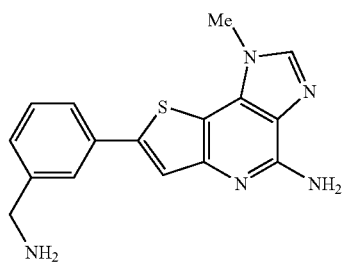

A9

A9.1: 4-Chloro-7-[3-(t-butyloxycarbonylaminomethyl)phenyl]-1-methyl-1H-imidazo[4,5-d]thieno[3,2-b]pyridine

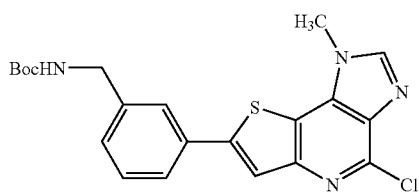

A9.1

A mixture of A2.8 (620 mg; 2.05 mmol), 3-(N-Bocaminomethyl)phenylboronic acid, [purchased from Frontier Scientific] (652 mg; 2.60 mmol), tetrakis(triphenylphosphine) palladium(0) (60 mg; 0.048 mmol), 2M Na$_2$CO$_3$ (4 ml), ethanol (5 ml) and toluene (8 ml) was vigorously stirred at 95° C. for 0.5 hr. After cooling to rt, the reaction mixture was partitioned between ethyl acetate (100 ml) and water (25 ml). After drying (MgSO$_4$), the organic layer was concentrated to afford a yellow oil, that was chromatographed on a 5×15 cm silica gel column using a stepwise gradient from 100% dichloromethane to 3% methanol in dichloromethane. The purest fractions were concentrated to afford 729 mg (83%) of A9.1 as a light yellow foam.

$^1$H-NMR (CDCl$_3$) δ: 7.97 (1H, s), 7.82 (1H, s), 7.63 (2H, m), 7.44 (2H, t, J=7.5 Hz), 7.33 (1H, d, J=7.5 Hz), 4.95 (1H, m), 4.40 (2H, d, J=5.5 Hz), 4.16 (3H, s), 1.48 (9H, s) HPLC (A): 99%, ret. time 1.86 min., LC/MS (M+H)$^+$=429.12 (431.12).

A9.2: 4-Chloro-7-[3-(aminomethyl)phenyl]-1-methyl-1H-imidazo[4,5-d]thieno[3,2-b]pyridine dihydrochloride salt

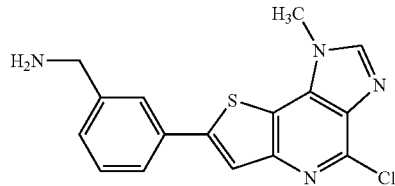

A9.2

A slurry of A9.1 (720 mg; 1.60 mmol) and 4N HCl in dioxane (4 ml; 16 mmol) in 5 ml of dioxane was stirred at rt for 2 hrs. After concentrating to dryness, the residue was triturated with ethyl ether to afford 640 mg (99%) of A9.2 as a light yellow solid.

$^1$H-NMR (MeOD) δ: 8.48 (1H, s), 7.95 (1H, brs), 7.90 (1H, s), 7.87 (1H, m), 7.60 (2H, m), 4.25 (2H, s), 4.21 (3H, s). HPLC (A): 93%, ret. time 1.24 min., LC/MS (M+H)$^+$=329.14 (331.15).

A9.3: 7-[3-(aminomethyl)phenyl]-N-[4-methoxyphenylmethyl]-1-methyl-1H-imidazo[4,5-d]thieno[3,2-b]pyridin-4-amine

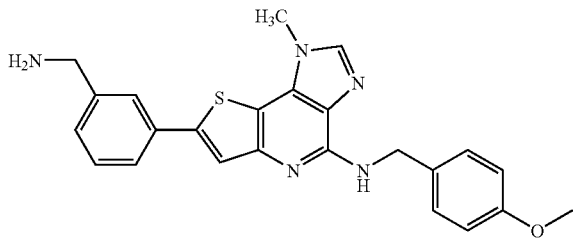

A9.3

A mixture of A9.2 (500 mg; 1.25 mmol) and 4 ml of 4-methoxybenzylamine were heated to 160-165° C. for 2 hrs. After cooling to rt, the reaction mixture was diluted with 25 ml of ethyl acetate and absorbed on Celite®. This mixture was loaded onto a 5×12 silica gel column, that was eluted with a gradient of dichloromethane to dichloromethane:methanol:concentrated ammonia, 90:9:1. The product containing fractions were concentrated and the residue was dissolved in 50 ml of dichloromethane. Heptane (200 ml) was added and the dichloromethane was removed in vacuo. The resulting suspension was allowed to stand overnight. Filtration and drying afforded 400 mg (75%) of A9.3 as a white powder. $^1$H-NMR (MeOD) δ: 8.15 (1H, s), 7.80 (1H, s), δ 7.79 (1H, s), 7.65 (1H, d, J=7.5 Hz), 7.40-7.24 (5H, m), 6.85 (2H, d, J=8.5 Hz), 4.67 (2H, d, J=6 Hz), 4.14 (3H, s), 3.78 (2H, s), 3.70 (3H, s). HPLC (A): 85%, ret. time 1.26 min., LC/MS (M+H)$^+$=430.28.

A9.4: 7-[3-(aminomethyl)phenyl]-1-methyl-1H-imidazo[4,5-d]thieno[3,2-b]pyridin-4-amine A solution of A9.3 (21 mg; 0.05 mmol) in 0.5 ml of TFA was allow to stand at rt for 18 hrs. and 50° C. for 2 hrs. After removing the volatiles in vacuo, the residue was purified by preparative HPLC to afford 5 mg (24%) of A9 as a white solid. HPLC (A): 99%, ret. time 1.00 min., LC/MS (M+H)$^+$=310.21.

Example A10

N-[[3-(4-amino-1-methyl-1H-imidazo[4,5-d]thieno[3,2-b]pyridin-7-yl)phenyl]methyl]-1-methyl-4-piperidinecarboxamide

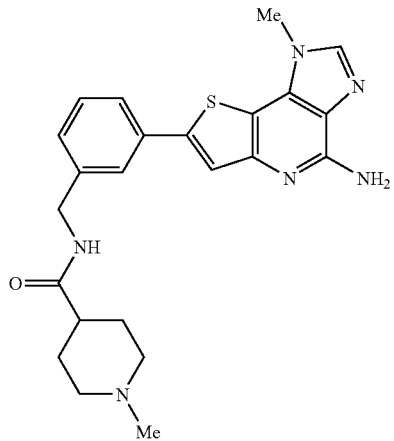

A10

A mixture of A9.3 (13 mg; 0.03 mmol), 1-methylpiperidine-4-carboxylic acid hydrochloride salt (8 mg; 0.04 mmol), EDC (12 mg; 0.06 mmol), 1-hydroxybenztriazole (6 mg; 0.04 mmol) and diisopropylethylamine (0.028 ml; 0.15 mmol) in MDF (0.5 ml) was heated to 60° C. for 0.5 hrs. After the volatiles were removed in vacuo, the residue was dissolved in a small volume of TFA and heated to 60° C. for 2 hrs. After removing the volatiles in vacuo, the residue was purified by preparative HPLC to afford 15 mg (94%) of A10 as a light yellow solid. $^1$H-NMR (DMSO-d$^6$) δ: 8.74 (2H, brs), 8.64 (1H, t, J=5.5 Hz), 8.48 (1H, s), 7.77 (1H, s), 7.73 (1H, d, J=8 Hz), 7.68 (1H, s), 7.50 (1H, t, J=7.5 Hz), 7.33 (1H, d, J=8 Hz), 4.37 (2H, d, J=5.5 Hz), 4.04 (1H, s), 3.47 (2H, m) 2.97 (2H, m), 2.78 (4H, m), 1.95 (2H, m), 1.80 (2H, m). HPLC (A): 99%, ret. time 1.10 min., LC/MS (M+H)$^+$=435.32.

Caution—although the compounds in the table below have not been tested in the Ames assay it would be prudent to handle these compounds as if they were Ames positive.

Examples A11-31

Examples A11-A 31 described in Table A.1 were prepared starting with amine A9 using the following procedure. To an individual well of a 48-position MiniBlock® XT reactor was added 150 µL of a 0.25 M solution of carboxylic acids (0.038 mmol, 1.25 eq, diversity reagent) in DMF (dimethylformamide), followed by the addition of 100 µL of a 0.375 M solution of 1-hydroxybenzotriazol in DMF (0.038 mmol, 1.25 equiv) and 150 µL of a 0.25 M solution of N-(3-dimethylaminopropyl)-N'-ethylcarbodiimide hydrochloride (0.038 mmol, 1.25 equiv). The reactor was agitated for 10 minutes at room temperature. 150 µL of a 0.20 M solution of the amine (A9) in dimethylformamide (DMF) (0.030 mmol, 1.00 equiv) and N-Ethyldiisopropylamine (0.150 mmol, 5.0 equiv) was dispensed into each well. The reactor was agitated overnight at room temperature. The crude product was diluted with methanol to a total volume of 1 mL, then purified by standard preparative HPLC-MS (H$_2$0/MeOH/0.1% TFA, gradient 35-90% MeOH)) utilizing mass-directed fractionation. The purified sample was reconstituted in 1:1/MeOH:DCE, transferred to a tared 2.5 mL plastic microtube, dried via centrifugal evaporation and weighed. The final product was analyzed by HPLC-MS (H$_2$0/MeOH/0.1% TFA). The compounds were isolated as their TFA salt.

TABLE A1

| Ex. | R | Name | HPLC Retention (min) | MS Reported |
|---|---|---|---|---|
| A11 | CH₃— | N-[[3-(4-amino-1-methyl-1H-imidazo[4,5-d]thieno[3,2-b]pyridin-7-yl)phenyl]methyl]acetamide | 2.06 | 352.11 |
| A12 | Me, NH₂ (chiral) | 2-amino-N-[[3-(4-amino-1-methyl-1H-imidazo[4,5-d]thieno[3,2-b]pyridin-7-yl)phenyl]methyl]-, (2S)-propanamide | 1.86 | 381.13 |
| A13 | pyrrolidinyl (2S) | N-[[3-(4-amino-1-methyl-1H-imidazo[4,5-d]thieno[3,2-b]pyridin-7-yl)phenyl]methyl]-, (2S)- 2-pyrrolidinecarboxamide | 1.84 | 407.14 |
| A14 | H₂N, Ph (alphaR) | alpha-amino-N-[[3-(4-amino-1-methyl-1H-imidazo[4,5-d]thieno[3,2-b]pyridin-7-yl)phenyl]methyl]-, (alphaR)-benzenepropanamide | 2.23 | 457.12 |
| A15 | 1,2,3-thiadiazol-4-yl | N-[[3-(4-amino-1-methyl-1H-imidazo[4,5-d]thieno[3,2-b]pyridin-7-yl)phenyl]methyl]-1,2,3-thiadiazole-4-carboxamide | 2.34 | 422.05 |
| A16 | Me, Me, Me (t-Bu) | N-[[3-(4-amino-1-methyl-1H-imidazo[4,5-d]thieno[3,2-b]pyridin-7-yl)phenyl]methyl]-2,2-dimethylpropanamide | 2.48 | 394.13 |
| A17 | cyclopropyl | N-[[3-(4-amino-1-methyl-1H-imidazo[4,5-d]thieno[3,2-b]pyridin-7-yl)phenyl]methyl] cyclopropanecarboxamide, | 2.28 | 378.11 |
| A18 | 3-pyridyl | N-[[3-(4-amino-1-methyl-1H-imidazo[4,5-d]thieno[3,2-b]pyridin-7-yl)phenyl]methyl]-3-pyridinecarboxamide | 2.05 | 415.10 |
| A19 | 4-pyridyl | N-[[3-(4-amino-1-methyl-1H-imidazo[4,5-d]thieno[3,2-b]pyridin-7-yl)phenyl]methyl]-4-pyridinecarboxamide | 1.99 | 415.09 |

TABLE A1-continued

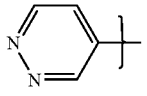

| Ex. | R | Name | HPLC Retention (min) | MS Reported |
|---|---|---|---|---|
| A20 | 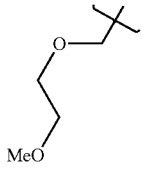 | N-[[3-(4-amino-1-methyl-1H-imidazo[4,5-d]thieno[3,2-b]pyridin-7-yl)phenyl]methyl]-4-pyridazinecarboxamide | 2.17 | 416.07 |
| A21 | 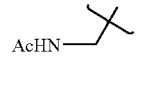 | N-[[3-(4-amino-1-methyl-1H-imidazo[4,5-d]thieno[3,2-b]pyridin-7-yl)phenyl]methyl]-2-(2-methoxyethoxy)acetamide | 2.25 | 426.09 |
| A22 | 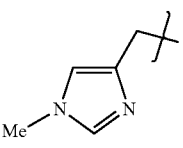 | 2-(acetylamino)-N-[[3-(4-amino-1-methyl-1H-imidazo[4,5-d]thieno[3,2-b]pyridin-7-yl)phenyl]methyl]acetamide | 1.95 | 409.1 |
| A23 | 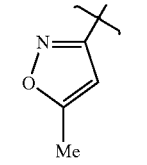 | N-[[3-(4-amino-1-methyl-1H-imidazo[4,5-d]thieno[3,2-b]pyridin-7-yl)phenyl]methyl]-1-methyl-1H-imidazole-4-acetamide | 1.82 | 432.14 |
| A24 | 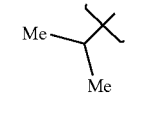 | N-[[3-(4-amino-1-methyl-1H-imidazo[4,5-d]thieno[3,2-b]pyridin-7-yl)phenyl]methyl]-5-methyl-3-isoxazolecarboxamide | 2.46 | 419.07 |
| A25 | 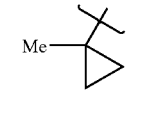 | N-[[3-(4-amino-1-methyl-1H-imidazo[4,5-d]thieno[3,2-b]pyridin-7-yl)phenyl]methyl]-2-methyl propanamide | 2.32 | 380.12 |
| A26 | 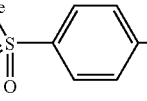 | N-[[3-(4-amino-1-methyl-1H-imidazo[4,5-d]thieno[3,2-b]pyridin-7-yl)phenyl]methyl]-1-methyl-cyclopropanecarboxamide | 2.41 | 392.13 |
| A27 |  | N-[[3-(4-amino-1-methyl-1H-imidazo[4,5-d]thieno[3,2-b]pyridin-7-yl)phenyl]methyl]-4-(methylsulfonyl) benzamide | 2.35 | 492.07 |

TABLE A1-continued

| Ex. | R | Name | HPLC Retention (min) | MS Reported |
|---|---|---|---|---|
| A28 | 3-(methylsulfonyl)phenyl | N-[[3-(4-amino-1-methyl-1H-imidazo[4,5-d]thieno[3,2-b]pyridin-7-yl)phenyl]methyl]-3-(methylsulfonyl) benzamide | 2.38 | 492.03 |
| A29 | 2-(methylsulfonyl)phenyl | N-[[3-(4-amino-1-methyl-1H-imidazo[4,5-d]thieno[3,2-b]pyridin-7-yl)phenyl]methyl]-2-(methylsulfonyl)benzamide | 2.30 | 492.10 |
| A30 | CH₂NH₂ | 2-amino-N-[[3-(4-amino-1-methyl-1H-imidazo[4,5-d]thieno[3,2-b]pyridin-7-yl)phenyl]methyl]acetamide | 1.73 | 367.12 |
| A31 | (R)-CH(Me)NH₂ | 2-amino-N-[[3-(4-amino-1-methyl-1H-imidazo[4,5-d]thieno[3,2-b]pyridin-7-yl)phenyl]methyl]-(2R)-propanamide | 1.80 | 381.13 |

Example A32

7-[3-(Aminomethyl)phenyl]-N,1-dimethyl-1H-imidazo[4,5-d]thieno[3,2-b]pyridin-4-amine

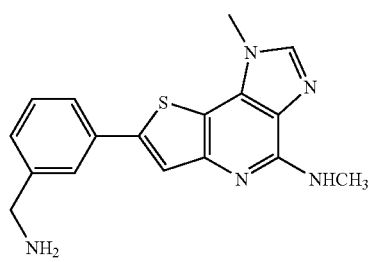

A32

A9.2 (575 mg, 1.3 mmol) was suspended in 8M methylamine in ethanol (10 mL) and heated at 135° C. in a microwave for 1 h. The reaction mixture was cooled to room temperature and the solvent removed under reduced pressure. The crude product was suspended in water and filtered. The filter cake was rinsed with a 1:1 mixture of ether and hexane and dried to yield A32 (385 mg, 92%). LCMS ret time=1.03 min, 97% purity MS: 324.23. NMR (DMSO-d$^6$) 400 mhz δ: 8.17 (s, 1H) 7.83 (s, 1H), 7.84-7.60 (m, 2H) 7.44-7.24 (m, 2H) 6.90-6.80 (m, 1H), 4.03 (s, 3H), 3.78 (s, 2H), 2.96 (d, 3H)

Examples A33-59

Examples A33-A 59 described in Table A2 were prepared starting with amine A32 using the procedure outlined for the preparation of the compounds in Table A1. The compounds were isolated as their trifluoroacetate salts.

TABLE A2

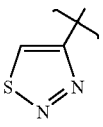

| Ex. | R | Name | HPLC Retention (min) | MS Reported |
|---|---|---|---|---|
| A33 | CH₃— | N-[[3-[1-methyl-4-(methylamino)-1H-imidazo[4,5-d]thieno[3,2-b]pyridin-7-yl]phenyl]methyl] acetamide | 2.18 | 366.46 |
| A34 | 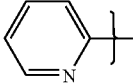 | N-[[3-[1-methyl-4-(methylamino)-1H-imidazo[4,5-d]thieno[3,2-b]pyridin-7-yl]phenyl]methyl]-1,2,3-thiadiazole-4-carboxamide | 2.44 | 436.36 |
| A35 |  | N-[[3-[1-methyl-4-(methylamino)-1H-imidazo[4,5-d]thieno[3,2-b]pyridin-7-yl]phenyl]methyl]-2-pyridinecarboxamide | 2.60 | 429.42 |
| A36 |  | N-[[3-[1-methyl-4-(methylamino)-1H-imidazo[4,5-d]thieno[3,2-b]pyridin-7-yl]phenyl]methyl]-2,2-dimethylpropanamide | 2.56 | 408.48 |
| A37 | 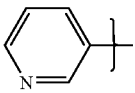 | N-[[3-[1-methyl-4-(methylamino)-1H-imidazo[4,5-d]thieno[3,2-b]pyridin-7-yl]phenyl]methyl]-cyclopropanecarboxamide | 2.37 | 392.47 |
| A38 | 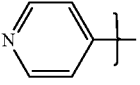 | N-[[3-[1-methyl-4-(methylamino)-1H-imidazo[4,5-d]thieno[3,2-b]pyridin-7-yl]phenyl]methyl]-3-pyridinecarboxamide | 2.15 | 429.43 |
| A39 | 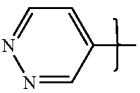 | N-[[3-[1-methyl-4-(methylamino)-1H-imidazo[4,5-d]thieno[3,2-b]pyridin-7-yl]phenyl]methyl]-4-pyridinecarboxamide | 2.11 | 429.41 |
| A40 | | N-[[3-[1-methyl-4-(methylamino)-1H-imidazo[4,5-d]thieno[3,2-b]pyridin-7-yl]phenyl]methyl]-4-pyridazinecarboxamide | 2.27 | 430.41 |

TABLE A2-continued

| Ex. | R | Name | HPLC Retention (min) | MS Reported |
|---|---|---|---|---|
| A41 | pyrazin-2-yl | N-[[3-[1-methyl-4-(methylamino)-1H-imidazo[4,5-d]thieno[3,2-b]pyridin-7-yl]phenyl]methyl]-2-pyrazinecarboxamide | 2.43 | 430.41 |
| A42 | NC-C(CH3)2- | 2-cyano-N-[[3-[1-methyl-4-(methylamino)-1H-imidazo[4,5-d]thieno[3,2-b]pyridin-7-yl]phenyl]methyl]acetamide | 2.17 | 391.46 |
| A43 | MeOCH2CH2OC(CH3)2- | N-[[3-[1-methyl-4-(methylamino)-1H-imidazo[4,5-d]thieno[3,2-b]pyridin-7-yl]phenyl]methyl]-2-(2-methoxyethoxy)acetamide, | 2.35 | 440.41 |
| A44 | AcNH-CH2-C(CH3)2- | N-[[3-[1-methyl-4-(methylamino)-1H-imidazo[4,5-d]thieno[3,2-b]pyridin-7-yl]phenyl]methyl]-2-(acetylamino) acetamide, | 2.07 | 423.41 |
| A45 | 1-methylimidazol-4-yl-CH2- | 1-methyl-N-[[3-[1-methyl-4-(methylamino)-1H-imidazo[4,5-d]thieno[3,2-b]pyridin-7-yl]phenyl]methyl]-1H-imidazole-4-acetamide | 1.95 | 446.42 |
| A46 | 5-methylisoxazol-3-yl | N-[[3-[1-methyl-4-(methylamino)-1H-imidazo[4,5-d]thieno[3,2-b]pyridin-7-yl]phenyl]methyl]-5-methyl-3-isoxazolecarboxamide | 2.54 | 433.41 |
| A47 | 5-methylisoxazol-4-yl | N-[[3-[1-methyl-4-(methylamino)-1H-imidazo[4,5-d]thieno[3,2-b]pyridin-7-yl]phenyl]methyl]-5-methyl-4-isoxazolecarboxamide | 2.87 | 433.41 |
| A48 | (CH3)2CH- | N-[[3-[1-methyl-4-(methylamino)-1H-imidazo[4,5-d]thieno[3,2-b]pyridin-7-yl]phenyl]methyl]-2-methyl-propanamide | 2.40 | 394.48 |

TABLE A2-continued

| Ex. | R | Name | HPLC Retention (min) | MS Reported |
|---|---|---|---|---|
| A49 | Me-cyclopropyl | N-[[3-[1-methyl-4-(methylamino)-1H-imidazo[4,5-d]thieno[3,2-b]pyridin-7-yl]phenyl]methyl]-1-methyl cyclopropanecarboxamide | 2.51 | 406.48 |
| A50 | PhC(Me)(Me)- | N-[[3-[1-methyl-4-(methylamino)-1H-imidazo[4,5-d]thieno[3,2-b]pyridin-7-yl]phenyl]methyl]-alpha,alpha-dimethyl benzeneacetamide | 2.93 | 470.42 |
| A51 | 4-(MeSO2)C6H4- | N-[[3-[1-methyl-4-(methylamino)-1H-imidazo[4,5-d]thieno[3,2-b]pyridin-7-yl]phenyl]methyl]-4-(methylsulfonyl) benzamide | 2.43 | 506.30 |
| A52 | 3-(MeSO2)C6H4- | N-[[3-[1-methyl-4-(methylamino)-1H-imidazo[4,5-d]thieno[3,2-b]pyridin-7-yl]phenyl]methyl]-3-(methylsulfonyl) benzamide | 2.45 | 506.34 |
| A53 | 2-(MeSO2)C6H4- | N-[[3-[1-methyl-4-(methylamino)-1H-imidazo[4,5-d]thieno[3,2-b]pyridin-7-yl]phenyl]methyl]-2-(methylsulfonyl) benzamide | 2.37 | 506.32 |
| A54 | 1-methylpiperidin-4-yl | 1-methyl-N-[[3-[1-methyl-4-(methylamino)-1H-imidazo[4,5-d]thieno[3,2-b]pyridin-7-yl]phenyl]methyl]-4-piperidinecarboxamide | 1.96 | 449.41 |
| A55 | (S)-CH(Me)(NH2) | N-[[3-[1-methyl-4-(methylamino)-1H-imidazo[4,5-d]thieno[3,2-b]pyridin-7-yl]phenyl]methyl]-(2S)-2-aminopropanamide | 2.66 | 495.42 |

TABLE A2-continued

| Ex. | R | Name | HPLC Retention (min) | MS Reported |
|---|---|---|---|---|
| A56 | Me—C(Me)(NH2)— (2R) | 2-amino-N-[[3-[1-methyl-4-(methylamino)-1H-imidazo[4,5-d]thieno[3,2-b]pyridin-7-yl]phenyl]methyl]-(2R)-propanamide | 2.66 | 495.41 |
| A57 | (2S)-pyrrolidinyl | N-[[3-[1-methyl-4-(methylamino)-1H-imidazo[4,5-d]thieno[3,2-b]pyridin-7-yl]phenyl]methyl]-(2S)-2-pyrrolidinecarboxamide | 2.74 | 521.43 |
| A58 | H2N-CH(CH2Ph)- | N-[[3-[1-methyl-4-(methylamino)-1H-imidazo[4,5-d]thieno[3,2-b]pyridin-7-yl]phenyl]methyl]-alpha-amino-(alphaR)benzenepropanamide | 3.11 | 571.43 |
| A59 | H2N-CH2- | N-[[3-[1-methyl-4-(methylamino)-1H-imidazo[4,5-d]thieno[3,2-b]pyridin-7-yl]phenyl]methyl]-2-amino-acetamide | 2.60 | 481.41 |

Utility

The compounds of the invention are inhibitors of IKK. Accordingly, compounds of formula (I) have utility in treating conditions were a decrease in NF-κB activity would be beneficial. Such conditions include diseases or disorders in which cytokine levels are modulated as a consequence of intracellular signaling via IKK, and in particular, diseases that are associated with an overproduction of cytokines IL-1, IL-4, IL-8, and TNF-α. As used herein, the terms "treating" or "treatment" encompass responsive and/or prophylaxis measures addressed to the disease state and/or its symptoms, e.g., measures designed to inhibit or delay the onset of the disease or disorder, achieve a full or partial reduction of the symptoms or disease state, and/or alleviate, lessen, or cure the disease and/or its symptoms. When reference is made herein to inhibition of "IKK," this means that either or both IKK-2 and IKK-1 are inhibited.

In view of their activity as inhibitors of IKK, compounds of Formula (I) are useful in treating inflammatory diseases, autoimmune diseases, destructive bone disorders, proliferative disorders, angiogenic disorders, infectious diseases, neurodegenerative diseases, viral diseases, and ischemia reperfusion conditions.

More particularly, the inventive compounds may be used to treat inflammatory diseases including, but not limited to, arthritis (e.g., rheumatoid arthritis, lyme disease arthritis, osteoarthritis, traumatic arthritis, rubella arthritis, psoriatic arthritis, gouty arthritis, and other arthritic conditions); glomerulonephritis, pancreatitis (acute or chronic), diabetes, diabetic retinopathy, macular degeneration, conjunctivitis, aplastic anemia, thrombocytopenia, gastritis, chronic thyroiditis, chronic active hepatitis, multiple sclerosis, inflammatory bowel disease, ulcerative colitis, Crohn's disease, cachexia (including cachexia secondary to infection, cancer, or heart disease), periodontal disease, Alzheimer's disease, Parkinson's disease, keloid formation, pulmonary sarcoidosis, myasthenia gravis, inflammatory reaction induced by endotoxin, Reiter's syndrome, gout, acute synovitis, diseases characterized by massive neutrophil infiltration, ankylosing spondylitis, influenze, cerebral malaria, silicosis, bone resorption disease, fever, myalgias due to infection, osteoporosis, multiple myeloma-related bone disorder, neurodegenerative disease caused by traumatic injury, and traumatic brain injury.

The inventive compounds may also be used to treat acute or chronic graft vs host reactions (e.g., pancreatic islet allograft), acute or chronic transplant rejection (e.g., kidney, liver, heart, lung, pancreas, bone marrow, cornea, small bowel, skin allografts, skin homografts, heterografts, and/or cells derived from such organs), and skin conditions including, but not limited to scar tissue formation, eczema, atopic dermatitis, contact dermatitis, urticaria, schleroderma, scleraclerma, and psoriasis. The inventive compounds also may be used to treat allergies and respiratory conditions, including asthma, acute respiratory distress syndrome, hayfever, allergic rhinitis, and any chronic pulmonary inflammatory disease such as chronic obstructive pulmonary disease. The compounds further may be used to treat steroid resistance in asthma and allergies.

Additionally, the inventive compounds may be used to treat inflammation associated with autoimmune diseases including, but not limited to, systemic lupus erythematosis, Addison's disease, autoimmune polyglandular disease (also known as autoimmune polyglandular syndrome), and Grave's disease. The inventive compounds may be used to infectious diseases such as sepsis, septic shock, Shigellosis, and *Heliobacter Pylori*.

The compounds may be used to treat viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS/ARC or malignancy, and herpes.

The inventive compounds also may be used to treat angiogenic disorders including solid tumors, ocular neovascularization, and infantile haemangiomas.

In addition, IKK inhibitors of this invention inhibit the expression of inducible pro-inflammatory proteins such as prostaglandin endoperoxide synthase-2 (PGHS-2), also referred to as cyclooxygenase-2 (COX-2). Accordingly, additional conditions that may be treated with the inventive compounds include edema, analgesia and pain, such as neuromuscular pain, headache, pain caused by cancer or surgery, dental pain and arthritis pain. In view of their COX-2 inhibitory activity, the inventive compounds also may be used to treat cancer including without limitation epithelial cancer and adenocarcinoma.

In addition, IKK (+/−) mice when fed a high fat diet have reduced insulin levels and reduced blood glucose levels. Accordingly compound of this invention are useful in the treatment of Type II diabetes (also known as non-insulin dependant diabetes).

Additionally, the compounds of this invention are useful to treat ischemia, including ischemia resulting from vascular occlusion, cerebral infarction, stroke, and related cerebral vascular diseases (including cerebrovascular accident and transient ischemic attack). Accordingly, the compounds may be used to treat myocardial infarction, coronary artery disease, non-Q wave MI, congestive heart failure, ventricular hypertrophy, cardiac arrhythmias, unstable angina, chronic stable angina, Prinzmetal's angina, high blood pressure, intermittent claudication, silent ischemia, cardiac hypertrophy, and peripheral occlusive arterial disease (e.g., peripheral arterial disease, critical leg ischemia, prevention of amputation, and prevention of cardiovascular morbidity such as MI, stroke or death).

Additionally, in view of their activity in treating ischemia, the compounds of the invention may be useful to treat symptoms or consequences occurring from thrombosis, atherosclerosis, peripheral arterial disease, and thrombotic or thromboembolic symptoms or consequences associated with and/or caused by one or more of the following: thromboembolic stroke (including that resulting from atrial fibrillation or from ventricular or aortic mural thrombus), venous thrombosis (including deep vein thrombosis), arterial thrombosis, cerebral thrombosis, pulmonary embolism, cerebral embolism, thrombophilia (e.g., Factor V Leiden, and homocystinenimia), coagulation syndromes and coagulopathies (e.g., disseminated intravascular coagulation), restenosis (e.g., following arterial injury induced endogenously or exogenously), atrial fibrillation, and ventricular enlargement (including dilated cardiac myopathy and heart failure). The compounds of the invention also may be used to treat symptoms or consequences of atherosclerotic diseases and disorders, such as atherosclerotic vascular disease, atherosclerotic plaque rupture, atherosclerotic plaque formation, transplant atherosclerosis, and vascular remodeling atherosclerosis. The compounds of the invention further may be used to treat symptoms or consequences of thrombotic or thromboembolic conditions associated with cancer, surgery, inflammation, systematic infection, artificial surfaces (such as stents, blood oxygenators, shunts, vascular access ports, vascular grafts, artificial valves, etc.), interventional cardiology such as percutaneous transluminal coronary angioplasty (PTCA), immobility, medication (such as oral contraceptives, hormome replacement therapy, and heparin), pregnancy and fetal loss, and diabetic complications including retinopathy, nephropathy, and neuropathy.

The compounds of the present invention may be used for the preservation of tissue, for example, the preservation of tissue as relates to organ transplantation and surgical manipulation. The compounds may be used to treat diseases or disorders in other tissues or muscles that are associated with ischemic conditions and/or to enhance the strength or stability of tissue and muscles. For example, the compounds may be used to treat muscle cell damage and necrosis and/or to enhance athletes' performance.

Additional diseases and disorders that may be treated with the inventive compounds include irritable bowel syndrome, leukemia, CNS disorders associated with cerebral ischemia, such as cerebral infarction, cerebral edema and the like, and diseases associated with proliferation of smooth muscle cells, mesangial cells, and fibroblasts. Such diseases include renal fibrosis, hepatic fibrosis, prostate hypertrophy, and pulmonary fibrosis.

The inventive compounds also may be used to treat veterinary viral infections, such as lentivirus infections, including, but not limited to, equine infectious anemia virus; or retro virus infections, including feline immunodeficiency virus, bovine immunodeficiency virus, and canine immunodeficiency virus.

The inventive compounds are also effective in treating oncological diseases, in treating cancer and tumors, such as solid tumors, lymphomas and leukemia, and in particular, breast cancer, prostate cancer, and Hodgkin's lymphoma.

Additionally this invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid or liquid tumors which are associated with IKK, especially those tumors which are significantly dependent on IKK for their growth and spread, including for example, hematopoietic tumors, cancers of the bladder, squamous cell, head, colorectal, oesophageal, gynecological (such as ovarian), pancreas, breast, prostate, lung, vulva, skin, brain, genitourinary tract, lymphatic system (such as thyroid), stomach, larynx and lung.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of the skin, including melanoma;

hematopoietic tumors including those of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

hematopoietic tumors including those of plasma cell lineage such as multiple myeloma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Additionally, the compounds of formula I are useful in the treatment of the following cancers.

Breast and other cancers: Hu, M C-T, and Hung, M C. "Role of IkB kinase in tumorigenesis" Future Oncology (2005) 1(1), 67-78.

Colon, lung, and other cancers: Jun-Li Luo, Hideaki Kamata, and Michael Karin. "IKK/NF-κB signaling: balancing life and death—a new approach to cancer therapy" J Clin Invest. 2005 115(10): 2625-2632.

Colon, lung, stomach, oesophagus, ovarian and other cancers: Michael Karin1 & Florian R. Greten2 "NF-κB: LINKING INFLAMMATION AND IMMUNITY TO CANCER DEVELOPMENT AND PROGRESSION" Nature Reviews Immunology 5, 749-759 (2005).

Lung, pancreatic, colon and other cancers: Greten F R, Karin M. "The IKK/NF-kappaB activation pathway—a target for prevention and treatment of cancer." Cancer Lett. 2004; 206(2):193-9.

Multiple Myeloma: Hideshima T, Chauhan D, Richardson P, Mitsiades C, Mitsiades N, Hayashi T, Munshi N, Dang L, Castro A, Palombella V, Adams J, Anderson K C. "NF-kappa B as a therapeutic target in multiple myeloma." J Biol. Chem. 2002; 277(19):16639-47.

Lymphoma: Lam L T, Davis R E, Pierce J, Hepperle M, Xu Y, Hottelet M, Nong Y, Wen D, Adams J, Dang L, Staudt L M. "Small molecule inhibitors of IkappaB kinase are selectively toxic for subgroups of diffuse large B-cell lymphoma defined by gene expression profiling." Clin Cancer Res. 2005; 11(1): 28-40.

Melanoma: Burke J R. "Targeting I kappa B kinase for the treatment of inflammatory and other disorders." Curr Opin Drug Discov Devel. 2003; 6(5):720-8. and a paper in press: Jinming Yang, Katayoun I. Amiri, James R. Burke, Johannes A. Schmid, and Ann Richmond. "BMS-345541 Targets IkappaB Kinase to Induce Apoptosis in Melanoma: Involvement of Nuclear Factor-kappaB and Mitochondria Pathways." Clin. Cancer Res., in press. The above references are hereby incorporated by reference.

Compounds of formula I may induce or inhibit apoptosis. The apoptotic response is aberrant in a variety of human diseases. Compounds of formula I, as modulators of apoptosis, will be useful in the treatment of cancer (including but not limited to those types mentioned hereinabove), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of formula I are especially useful in treatment of tumors having a high incidence of IKK kinase activity, such as melanomas, and multiple myeloma. By the administration of a composition (or a combination) of the compounds of this invention, development of tumors in a mammalian host is reduced.

The invention also provides a pharmaceutical composition comprising a compound of formula I in combination with pharmaceutically acceptable carrier and an anti-cancer or cytotoxic agent. In a preferred embodiment said anti-cancer or cytotoxic agent is selected from the group consisting of linomide; inhibitors of integrin αvβ3 function; angiostatin; razoxin; tamoxifen; toremifen; raloxifene; droloxifene; iodoxyfene; megestrol acetate; anastrozole; letrazole; borazole; exemestane; flutamide; nilutamide; bicalutamide; cyproterone acetate; gosereline acetate; luprolide; finasteride; metalloproteinase inhibitors; inhibitors of urokinase plasminogen activator receptor function; growth factor antibodies; growth factor receptor antibodies such as Avastin® and Erbitux®; tyrosine kinase inhibitors; serine/threonine kinase inhibitors); methotrexate; 5-fluorouracil; purine; adenosine analogues; cytosine arabinoside; doxorubicin; daunomycin; epirubicin; idarubicin; mitomycin-C; dactinomycin; mithramycin); cisplatin; carboplatin; nitrogen mustard; melphalan; chlorambucil; busulphan; cyclophosphamide; ifosfamide nitrosoureas; thiotephan; vincristine; Taxol®; Taxotere®; epothilone analogs; discodermolide analogs; eleutherobin analogs; etoposide; teniposide; amsacrine; topotecan; and flavopyridols.

In the field of medical oncology it is normal practice to use a combination of different forms of treatment to treat each patient with cancer. In medical oncology the other component(s) of such conjoint treatment in addition to the antiproliferative, antiangiogenic and/or vascular permeability reducing treatment defined herein before may be: surgery, radiotherapy or chemotherapy. Such chemotherapy may cover three main categories of therapeutic agent:

1: antiangiogenic agents such as inhibitors of VEGF or related kinases (such as FLT, or KDR), linomide, antibodies which block angiogenesis, inhibitors of integrin αvβ3 function, angiostatin, razoxin;

2: cytostatic agents such as antiestrogens (for example tamoxifen, toremifen, raloxifene, droloxifene, iodoxyfene), progestogens (for example megestrol acetate), aromatase inhibitors (for example anastrozole, letrazole, borazole, exemestane), antiharmones, antiprogestogens, antiandrogens (for example flutamide, nilutamide, bicalutamide, cyproterone acetate), LHRH agonists and antagonists (for example gosereline acetate, luprolide), inhibitors of testosterone 5α-dihydroreductase (for example finasteride), farnesyltransferase inhibitors, anti-invasion agents (for example metalloproteinase inhibitors like marimastat and inhibitors of urokinase plasminogen activator receptor function) and inhibitors of growth factor function, (such growth factors include for example EGF, FGF, platelet derived growth factor and hepatocyte growth factor such inhibitors include growth factor antibodies, growth factor receptor antibodies such as Avastin® and Erbitux®, tyrosine kinase inhibitors and serine/threonine kinase inhibitors);

3: antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); Intercalating antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide nitrosoureas, thiotephan); antimitotic agents (for example vinca alkaloids like vincristine and taxoids like Taxol®, Taxotere® and newer microbtubule agents such as epothilone analogs, discodermolide analogs, and eleutherobin analogs); topoisomerase inhibitors (for example epipodophyllotoxins like etoposide and teniposide, amsacrine, topotecan); cell cycle inhibitors (for example flavopyridols).

The present invention thus provides methods for treating such conditions, comprising administering to a subject in need thereof an effective amount of at least one compound of formula I or a salt thereof. Other therapeutic agents such as those described herein may be employed in combination with compounds of formula I. In the methods of the present invention, such other therapeutic agent(s) may be administered prior to, simultaneously with, or following administration of the inventive compound(s).

When the terms "IKK associated condition" or "IKK associated disease or disorder" are used herein, each is intended to encompass all of the conditions identified above as if repeated at length, as well as any other condition that is modulated by IKK kinase activity.

The present invention thus provides methods for treating such conditions, comprising administering to a subject in need thereof an effective amount of at least one compound of Formula (I), or a pharmaceutically-acceptable salt, hydrate, or prodrug thereof. The methods of treating IKK kinase-associated conditions may comprise administering compounds of Formula (I) alone or in combination with each other and/or other suitable therapeutic agents such as anti-inflammatory drugs, antibiotics, anti-viral agents, anti-oxidants, cholesterol/lipid lowering agents, anti-tumor agents including antiproliferative agents, and agents used to treat ischemia.

Examples of suitable other anti-inflammatory agents with which the inventive compounds may be used include aspirin, cromolyn, nedocromil, theophylline, zileuton, zafirlukast, monteleukast, pranleukast, indomethacin, and lipoxygenase inhibitors; non-steroidal antiinflammatory drugs (NSAIDs) (such as ibuprofen and naproxin); TNF-α inhibitors (such as tenidap and rapamycin or derivatives thereof), or TNF-α antagonists (e.g., infliximab, enbrel, D2E7, OR1384), cytokine modulators (e.g. TNF-alpha converting enzyme [TACE] inhibitors, Interleukin-1 converting enzyme (ICE) inhibitors, Interleukin-1 receptor antagonists), prednisone, dexamethasone, Enbrel®, cyclooxygenase inhibitors (i.e., COX-1 and/or COX-2 inhibitors such as Naproxen®, Celebrex®, or Vioxx®), CTLA4-Ig agonists/antagonists (LEA29Y), CD40 ligand antagonists, IMPDH inhibitors (such as mycophenolate [CellCept®] and VX-497), integrin antagonists, alpha-4 beta-7 integrin antagonists, cell adhesion inhibitors, interferon gamma antagonists, ICAM-1, prostaglandin synthesis inhibitors, budesonide, clofazimine, CNI-1493, CD4 antagonists (e.g. priliximab), other p38 mitogen-activated protein kinase inhibitors, protein tyrosine kinase (PTK) inhibitors, therapies for the treatment of irritable bowel syndrome (e.g., Zelmac®, Zelnorm®, and Maxi-K® openers such as those disclosed in U.S. Pat. No. 6,184,231 B1), corticosteroids (such as beclomethasone, triamcinolone, budesonide, fluticasone, flunisolide, dexamethasone, prednisone, and dexamethasone); disassociated steroids; chemokine receptor modulators (including CCR1, CCR2, CCR3, CCR4, and CXCR2 receptor antagonists); secretory and cytosolic phospholipase A2 inhibitors, VLA4 antagonists, glucocorticoids, salicylates, nitric oxide, and other immunosuppressants; and nuclear translocation inhibitors, such as deoxyspergualin (DSG).

To treat pain, the inventive compounds may be used in combination with aspirin, NSAIDs, or with 5-HT 1 receptor agonists such as buspirone, sumitriptan, eletriptan or rizatriptan, or with opioids (e.g. morphine, codeine, hydomorphone).

Examples of suitable diabetic agents with which the inventive compounds may be used include insulin (of porcine or recombinant human origin including, short acting insulins such as Humalog®, Regular, intermediate acting insulins such NPH, lente, and long acting insulins such as ultralente or glarginine (Lantus®)); sulfonylureas such as glyburide and glipizide; secretegogues such as repaginide, and nateglinide; Peroisome proliferators-activated receptor (PPAR) agonists such as rosiglitazole and pioglitazone, and mixed PPAR alpha/gamma dual agonists agonists such as muriglitazar; biquamides such as metformin, and glucosidase inhibitors such as acarbose and miglitol, PPAR-alpha agonists, SGLT2 inhibitors, inhibitors of fatty acid binding protein (aP2) such as those disclosed in U.S. Ser. No. 09/519,079 filed Mar. 6, 2000 and assigned to the present assignee, glucagon-like peptide-1 (GLP-1), glucagon phosphorylase, and dipeptidyl peptidase IV (DP4) inhibitors.

Examples of suitable antibiotics with which the inventive compounds may be used include β-lactams (e.g., penicillins, cephalosporins and carbopenams); β-lactam and lactamase inhibitors (e.g., augamentin); aminoglycosides (e.g., tobramycin and streptomycin); macrolides (e.g., erythromycin and azithromycin); quinolones (e.g., cipro and tequin); peptides and deptopeptides (e.g. vancomycin, synercid and daptomycin) metabolite-based anti-biotics (e.g., sulfonamides and trimethoprim); polyring systems (e.g., tetracyclins and rifampins); protein synthesis inhibitors (e.g., zyvox, chlorophenicol, clindamycin, etc.); and nitro-class antibiotics (e.g., nitrofurans and nitroimidazoles).

Examples of suitable antiviral agents for use with the inventive compounds include nucleoside-based inhibitors, protease-based inhibitors, and viral-assembly inhibitors.

Examples of suitable anti-osteoporosis agents for use in combination with the compounds of the present invention include alendronate, risedronate, PTH, PTH fragment, raloxifene, calcitonin, RANK ligand antagonists, calcium sensing receptor antagonists, TRAP inhibitors, selective estrogen receptor modulators (SERM) and AP-1 inhibitors.

Examples of suitable anti-oxidants for use in combination with the compounds of the present invention include lipid peroxidation inhibitors such as probucol, BO-653, Vitamin A, Vitamin E, AGI-1067, and α-lipoic acid.

A further use of the compounds of this invention is in combination with steriodal or non-steroidal progesterone receptor agonists ("PRA"), such as levonorgestrel, medroxyprogesterone acetate (MPA).

In addition, the compounds may be used with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLO™ (i.e., cis-4-cyano-4-[3-(cyclopentyloxy)-4-methoxyphenyl]cyclohexane-1-carboxylic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive compounds may also be useful in combination with anticancer strategies and chemotherapies such as taxol and/or cisplatin. The compounds may be used in conjunction with antitumor agents such as paclitaxel, adriamycin, epithilones, cisplatin, and carboplatin.

In view of their usefulness in treating ischemia, the inventive compounds may be used in combination with agents for inhibiting $F_1F_0$-ATPase, including efrapeptin, oligomycin, autovertin B, azide, and compounds described in U.S. patent application Ser. No. 60/339,108, filed Dec. 10, 2001 and assigned to the present assignee; -alpha- or beta-adrenergic blockers (such as propranolol, nadolol, carvedilol, and prazosin), or -β-adrenergic agonists (such as albuterol, terbutaline, formoterol, salmeterol, bitolterol, pilbuterol, and fenoterol); antianginal agents such as nitrates, for example, sodium nitrates, nitroglycerin, isosorbide mononitrate, isosorbide dinitrate, and nitrovasodilators; antiarrhythmic agents including Class I agents (such as propafenone); Class II agents (propranolol); Class III agents (such as sotalol, dofetilide, amiodarone, azimilide and ibutilide); Class IV agents (such as ditiazem and verapamil); $K^+$ channel modulators such as $I_{Ach}$ inhibitors and inhibitors of the $K_v1$ subfamily of $K^+$ channel openers such as $I_{Kur}$ inhibitors (e.g., compounds disclosed in U.S. application Ser. No. 09/729,731, filed Dec. 5, 2000); and gap-junction modulators such as connexions; anticoagulant or antithrombotic agents including aspirin, warfarin, ximelagtran, low molecular weight heparins (such as lovenox, enoxaparain, and dalteparin), anti-platelet agents such as GPIIb/GPIIIa blockers, (e.g., abciximab, eptifibatide, and tirofiban), thromboxane receptor antagonists (e.g., ifetroban), $P2Y_1$ and $P2Y_{12}$ antagonists (e.g., clopidogrel, ticlopidine, CS-747, and aspirin/clopidogrel combinations), and Factor Xa inhibitors (e.g., fondaprinux); and diuretics such as sodium-hydrogen exchange inhibitors, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, and amiloride.

Additionally, the inventive compounds may be used in combination with lipid profile modulators and antiatherosclerotic agents including HMG-CoA reductase inhibitors (e.g., pravastatin, simvastatin, atorvastatin, fluvastatin, cerivastatin, AZ4522, itavastatin [Nissan/Kowa]), ZD4522 (a.k.a. rosuvastatin, atavastatin or visastatin), pravachol, squalene synthetase inhibitors, fibrates, bile acid sequestrants (such as questran), niacin and niacin/statin combinations, lipooxygenase inhibitors, ileal $Na^+$/bile acid cotransporter inhibitors, ACAT1 inhibitors, ACAT2 inhibitors, dual ACAT1/2 inhibitors, microsomal triglyceride transport protein inhibitors (such as disclosed in U.S. Pat. Nos. 5,739,135, 5,712,279 and 5,760,246), cholesterol absorption inhibitors (such as Zetia®), cholesterol ester transfer protein inhibitors (e.g., CP-529414), PPAR-delta agonists, PPAR-alpha agonists, dual PPAR-alpha/delta agonists, LXR-alpha agonists, LXR-beta agonists, LXR dual alpha/beta agonists, and SCAP modulators.

The combination of the inventive compounds with other therapeutic agents may prove to have additive and synergistic effects. The combination may be advantageous to increase the efficacy of the administration or decrease the dosage to reduce possible side-effects.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of IKK enzyme activity.

The inventive compounds have been tested and have shown activity as inhibitors of IKK, IkB, NF-κB and/or TNF-α. For example, THP-1 (human monocytic cell line) obtained from ATCC was cultured in RPMI-1640 supplemented with 10% FBS, sodium pyruvate, HEPES, 5-mercaptoethanol, Penicillin/Streptomycin. To a 96-well plate containing THP-1 cells ($1.4 \times 10^6$/mL, $2.5 \times 10^5$ cells/well) in 180 μL RPMI-1640 was added 10 μL of the test compound in 10% DMSO. Typically, test compound concentrations of 0.1-100 μM were used in the assay. After one hour at 37° C., 10 μL of 1000 ng/mL lipopolysaccharide (LPS from *Salmonella typhosa*, Sigma) was added to each well. After an additional 6 hours at 37° C., the supernatants were collected following a 5 minute centrifugation of the plate to pellet the cells. The amount of TNFα in these supernatants was then measured using a TNFα-specific ELISA (Pharmingen). After subtracting out the amount of TNFα in a control that had not been treated with LPS, the percent inhibition was calculated versus a control that was treated with LPS but with no test compound added. The compounds of this invention are active in vivo in the LPS-induced TNFα secretion model. Likewise, assays known in the field are applied to establish the activity of the compounds as inhibitors of IKK, IkB, and/or the NF-κB pathway.

TNFα Secretion Assay

The ability of compounds to inhibit the production and secretion of TNFα from leukocytes was performed using either PBMC (obtained as described above) or the THP-1 cell line as a source of monocytes. Compounds were diluted in RPMI 1640 supplemented with 10% FBS and DMSO at a final concentration of 0.2%. Cells ($2 \times 10^5$/well in U-bottom 96 well plates) were pre-incubated with compounds for 30 min at 37 C prior to addition of lipopolysaccharide (LPS) at a final concentration of 6.25 ng/ml in a total volume of 200 μL. After 4 h at 37° C., 50 μL of supernatant was carefully aspirated for detection of soluble TNFα. Soluble TNFα was detected by ELISA developed by R&D Systems (Minneapolis, Minn.) according to the manufacturer's instructions.

We claim:

1. A compound of formula (I),

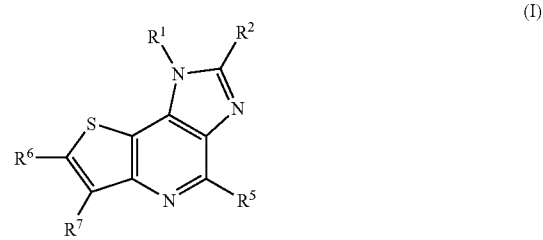

or pharmaceutically acceptable salt thereof, wherein
$R^1$ is selected from $C_{1-3}$ alkyl;
$R^2$ is hydrogen;
$R^5$ is $-NR^3R^4$;
$R^3$ and $R^4$ are independently selected from
  (a) hydrogen, or
  (b) alkyl;
$R^6$ is
  aryl, which may be optionally independently substituted as valence allows with one or more $Z^{1d}$, $Z^{2d}$ and $Z^{3d}$;
$R^7$ is
  (a) hydrogen, or halo,
$Z^{1d}$, $Z^{2d}$ and $Z^{3d}$ are independently
  (1) H
  (7) $-U^1$-halo,
  (10) $-U^1-NY^2Y^3$,
  (11) $-U^1-N(Y^4)-C(O)-Y^1$, $Y^1, Y^2, Y^3, Y^4$ and $Y^5$
(1) are each independently hydrogen, alkyl, (alkoxy)alkyl, cycloalkyl, (cycloalkyl)alkyl, aryl, (aryl)alkyl, piperidinyl, pyrrolidinyl, thiadiazolyl, pyridinyl, pyradizinyl, pyrazinyl, isoxazolyl, imidazolyl, or (imidazolyl)alkyl, any of which may be optionally independently substituted as valence allows with one or more $Z^4$, $Z^5$ and $Z^6$; or $Z^4$, $Z^5$, and $Z^6$ are optional substituents at each occurrence independently selected from
(1) H
(2) alkyl;
(3) —$U^1$—O—$Y^{5a}$,
(8) —$U^1$-cyano,
(10) —$U^1$—$NY^{2a}Y^{3a}$,
(11) —$U^1$—$N(Y^{4a})$—C(O)—$Y^{1a}$,
(16) —$U^1$—$N(Y^{4a})$—S(O)$_2$—$Y^{1a}$, $Y^{1a}, Y^{2a}, Y^{3a}, Y^{4a}$ and $Y^{5a}$
(1) are each independently hydrogen, or alkyl;
$U^1$ is independently
(1) a single bond,
(2) alkylene.

2. A compound of claim 1 wherein
$R^1$ is methyl, ethyl, propyl, or i-propyl.

3. A compound of claim 1, wherein
$R^6$ is phenyl optionally independently substituted as valence allows with one or more $Z^{1d}, Z^{2d}$ and $Z^{3d}$.

4. A compound of claim 3, wherein
$R^1$ is methyl, ethyl, propyl, or i-propyl.

5. A compound of claim 3, wherein
$R^6$ is

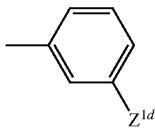

which may be further substituted with one or more $Z^{1d}$, $Z^{2d}$ and $Z^{3d}$.

6. A pharmaceutical composition comprising (a) at least one compound according to claim 1, or a pharmaceutically acceptable salt thereof, and (b) a pharmaceutically-acceptable carrier or diluent.

7. A pharmaceutical composition comprising (a) at least one compound according to claim 5, or a pharmaceutically acceptable salt thereof, and (b) a pharmaceutically-acceptable carrier or diluent.

8. A compound of claim 1, wherein the compound of formula is

N,1-Dimethyl-7-phenyl-1H-imidazo[4,5-d]thieno[3,2-b]pyridin-4-amine;
N-Ethyl-1-methyl-7-phenyl-1H-imidazo[4,5-d]thieno[3,2-b]pyridin-4-amine;
1-methyl-7-phenyl-1H-imidazo[4,5-d]thieno[3,2-b]pyridin-4-amine;
7-(3-Fluorophenyl)-1-methyl-1H-imidazo[4,5-d]thieno[3,2-b]pyridin-4-amine;
6-Bromo-7-(3-fluorophenyl)-N,1-dimethyl-1H-imidazo[4,5-d]thieno[3,2-b]pyridin-4-amine;
7-(3-fluorophenyl)-N,1-dimethyl-1H-imidazo[4,5-d]thieno[3,2-b]pyridin-4-amine;
7-(3,5-difluorophenyl)-N,1-dimethyl-1H-imidazo[4,5-d]thieno[3,2-b]pyridin-4-amine;
7-[3-(aminomethyl)phenyl]-1-methyl-1H-imidazo[4,5-d]thieno[3,2-b]pyridin-4-amine;
N-[[3-(4-amino-1-methyl-1H-imidazo[4,5-d]thieno[3,2-b]pyridin-7-yl)phenyl]methyl]-1-methyl-4-piperidinecarboxamide;
N-[[3-(4-amino-1-methyl-1H-imidazo[4,5-d]thieno[3,2-b]pyridin-7-yl)phenyl]methyl]acetamide;
2-amino-N-[[3-(4-amino-1-methyl-1H-imidazo[4,5-d]thieno[3,2-b]pyridin-7-yl)phenyl]methyl]-(2S)-propanamide;
N-[[3-(4-amino-1-methyl-1H-imidazo[4,5-d]thieno[3,2-b]pyridin-7-yl)phenyl]methyl]-, (2S)-2-pyrrolidinecarboxamide;
alpha-amino-N-[[3-(4-amino-1-methyl-1H-imidazo[4,5-d]thieno[3,2-b]pyridin-1-yl)phenyl]methyl]-, (alphaR)-benzenepropanamide;
N-[[3-(4-amino-1-methyl-1H-imidazo[4,5-d]thieno[3,2-b]pyridin-7-yl)phenyl]methyl]-1,2,3-thiadiazole-4-carboxamide;
N-[[3-(4-amino-1-methyl-1H-imidazo[4,5-d]thieno[3,2-b]pyridin-7-yl)phenyl]methyl]-2,2-dimethylpropanamide;
N-[[3-(4-amino-1-methyl-1H-imidazo[4,5-d]thieno[3,2-b]pyridin-7-yl)phenyl]methyl]cyclopropanecarboxamide;
N-[[3-(4-amino-1-methyl-1H-imidazo[4,5-d]thieno[3,2-b]pyridin-7-yl)phenyl]methyl]-3-pyridinecarboxamide;
N-[[3-(4-amino-1-methyl-1H-imidazo[4,5-d]thieno[3,2-b]pyridin-7-yl)phenyl]methyl]-4-pyridinecarboxamide;
N-[[3-(4-amino-1-methyl-1H-imidazo[4,5-d]thieno[3,2-b]pyridin-7-yl)phenyl]methyl]-4-pyridazinecarboxamide;
N-[[3-(4-amino-1-methyl-1H-imidazo[4,5-d]thieno[3,2-b]pyridin-7-yl)phenyl]methyl]-2-(2-methoxyethoxy)acetamide;
2-(acetylamino)-N-[[3-(4-amino-1-methyl-1H-imidazo[4,5-d]thieno[3,2-b]pyridin-7-yl)phenyl]methyl]acetamide;
N-[[3-(4-amino-1-methyl-1H-imidazo[4,5-d]thieno[3,2-b]pyridin-7-yl)phenyl]methyl]-1-methyl-1H-imidazole-4-acetamide;
N-[[3-(4-amino-1-methyl-1H-imidazo[4,5-d]thieno[3,2-b]pyridin-7-yl)phenyl]methyl]-5-methyl-3-isoxazolecarboxamide;
N-[[3-(4-amino-1-methyl-1H-imidazo[4,5-d]thieno[3,2-b]pyridin-7-yl)phenyl]methyl]-2-methyl propanamide;
N-[[3-(4-amino-1-methyl-1H-imidazo[4,5-d]thieno[3,2-b]pyridin-7-yl)phenyl]methyl]-1-methyl-cyclopropanecarboxamide;
N-[[3-(4-amino-1-methyl-1H-imidazo[4,5-d]thieno[3,2-b]pyridin-7-yl)phenyl]methyl]-4-(methylsulfonyl)benzamide;
N-[[3-(4-amino-1-methyl-1H-imidazo[4,5-d]thieno[3,2-b]pyridin-7-yl)phenyl]methyl]-3-(methylsulfonyl)benzamide;
N-[[3-(4-amino-1-methyl-1H-imidazo[4,5-d]thieno[3,2-b]pyridin-1-yl)phenyl]methyl]-2-(methylsulfonyl)benzamide;
2-amino-N-[[3-(4-amino-1-methyl-1H-imidazo[4,5-d]thieno[3,2-b]pyridin-7-yl)phenyl]methyl]acetamide;
2-amino-N-[[3-(4-amino-1-methyl-1H-imidazo[4,5-d]thieno[3,2-b]pyridin-7-yl)phenyl]methyl]-(2R)-propanamide;
7-[3-(Aminomethyl)phenyl]-N,1-dimethyl-1H-imidazo[4,5-d]thieno[3,2-b]pyridin-4-amine;

N-[[3-[1-methyl-4-(methylamino)-1H-imidazo[4,5-d]
thieno[3,2-b]pyridin-7-yl]phenyl]methyl]acetamide;

N-[[3-[1-methyl-4-(methylamino)-1H-imidazo[4,5-d]
thieno[3,2-b]pyridin-7-yl]phenyl]methyl]-1,2,3-thiadiazole-4-carboxamide;

N-[[3-[1-methyl-4-(methylamino)-1H-imidazo[4,5-d]
thieno[3,2-b]pyridin-7-yl]phenyl]methyl]-2-pyridinecarboxamide;

N-[[3-[1-methyl-4-(methylamino)-1H-imidazo[4,5-d]
thieno[3,2-b]pyridin-7-yl]phenyl]methyl]-2,2-dimethylpropanamide;

N-[[3-[1-methyl-4-(methylamino)-1H-imidazo[4,5-d]
thieno[3,2-b]pyridin-1-yl]phenyl]methyl]-cyclopropanecarboxamide;

N-[[3-[1-methyl-4-(methylamino)-1H-imidazo[4,5-d]
thieno[3,2-b]pyridin-7-yl]phenyl]methyl]-3-pyridinecarboxamide;

N-[[3-[1-methyl-4-(methylamino)-1H-imidazo[4,5-d]
thieno[3,2-b]pyridin-7-yl]phenyl]methyl]-4-pyridinecarboxamide;

N-[[3-[1-methyl-4-(methylamino)-1H-imidazo[4,5-d]
thieno[3,2-b]pyridin-7-yl]phenyl]methyl]-4-pyridazinecarboxamide;

N-[[3-[1-methyl-4-(methylamino)-1H-imidazo[4,5-d]
thieno[3,2-b]pyridin-7-yl]-phenyl]methyl]-2-pyrazinecarboxamide;

2-cyano-N-[[3-[1-methyl-4-(methylamino)-1H-imidazo
[4,5-d]thieno[3,2-b]pyridin-7-yl]phenyl]methyl]acetamide;

N-[[-[1-methyl-4-(methylamino)-1H-imidazo[4,5-d]
thieno[3,2-b]pyridin-7-yl]phenyl]methyl]-2-(2-methoxyethoxy)acetamide;

N-[[3-[1-methyl-4-(methylamino)-1H-imidazo[4,5-d]
thieno[3,2-b]pyridin-1-yl]phenyl]methyl]-2-(acetylamino)acetamide;

1-methyl-N-[[3-[1-methyl-4-(methylamino)-1H-imidazo
[4,5-d]thieno[3,2-b]pyridin-7-yl]phenyl]methyl]-1H-imidazole-4-acetamide;

N-[[3-[1-methyl-4-(methylamino)-1H-imidazo[4,5-d]
thieno[3,2-b]pyridin-7-yl]phenyl]methyl]-5-methyl-3-isoxazolecarboxamide;

N-[[3-[1-methyl-4-(methylamino)-1H-imidazo[4,5-d]
thieno[3,2-b]pyridin-7-yl]phenyl]methyl]-5-methyl-4-isoxazolecarboxamide;

N-[[3-[1-methyl-4-(methylamino)-1H-imidazo[4,5-d]
thieno[3,2-b]pyridin-7-yl]phenyl]methyl]-2-methyl-propanamide;

N-[[3-[1-methyl-4-(methylamino)-1H-imidazo[4,5-d]
thieno[3,2-b]pyridin-7-yl]phenyl]methyl]-1-methylcyclopropanecarboxamide;

N-[[3-[1-methyl-4-(methylamino)-1H-imidazo[4,5-d]
thieno[3,2-b]pyridin-7-yl]phenyl]methyl]-alpha,alpha-dimethyl benzeneacetamide;

N-[[3-[1-methyl-4-(methylamino)-1H-imidazo[4,5-d]
thieno[3,2-b]pyridin-7-yl]phenyl]methyl]-4-(methylsulfonyl)benzamide;

N-[[3-[1-methyl-4-(methylamino)-1H-imidazo[4,5-d]
thieno[3,2-b]pyridin-7-yl]phenyl]methyl]-3-(methylsulfonyl)benzamide;

N-[[3-[1-methyl-4-(methylamino)-1H-imidazo[4,5-d]
thieno[3,2-b]pyridin-7-yl]phenyl]methyl]-2-(methylsulfonyl)benzamide;

1-methyl-N-[[3-[1-methyl-4-(methylamino)-1H-imidazo
[4,5-d]thieno[3,2-b]pyridin-7-yl]phenyl]methyl]-4-piperidinecarboxamide;

N-[[3-[1-methyl-4-(methylamino)-1H-imidazo[4,5-d]
thieno[3,2-b]pyridin-7-yl]phenyl]methyl]-(2S)-2-aminopropanamide;

2-amino-N-[[3-[1-methyl-4-(methylamino)-1H-imidazo
[4,5-d]thieno[3,2-b]pyridin-7-yl]phenyl]methyl]-(2R)-propanamide;

N-[[3-[1-methyl-4-(methylamino)-1H-imidazo[4,5-d]
thieno[3,2-b]pyridin-7-yl]phenyl]methyl]-(2S)-2-pyrrolidinecarboxamide;

N-[[3-[1-methyl-4-(methylamino)-1H-imidazo[4,5-d]
thieno[3,2-b]pyridin-7-yl]phenyl]methyl]-alpha-amino-(alphaR)benzenepropanamide; or N-[[3-[1-methyl-4-(methylamino)-1H-imidazo[4,5-d]
thieno[3,2-b]pyridin-7-yl]phenyl]methyl]-2-amino-acetamide;

or pharmaceutically acceptable salt thereof.

9. A pharmaceutical composition comprising (a) at least one compound according to claim 8, or a pharmaceutically acceptable salt thereof, and (b) a pharmaceutically-acceptable carrier or diluent.

\* \* \* \* \*